US011467168B2

(12) United States Patent
Liman et al.

(10) Patent No.: US 11,467,168 B2
(45) Date of Patent: Oct. 11, 2022

(54) METHODS OF IDENTIFYING A MOLDULATOR OF OTOPETRIN-MEDIATED PROTON TRANSLOCATION ACTIVITY

(71) Applicant: UNIVERSITY OF SOUTHERN CALIFORNIA, Los Angeles, CA (US)

(72) Inventors: Emily Liman, Santa Monica, CA (US); Yu-Hsiang Tu, Pasadena, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 111 days.

(21) Appl. No.: 16/634,566

(22) PCT Filed: Jul. 27, 2018

(86) PCT No.: PCT/US2018/044058
§ 371 (c)(1),
(2) Date: Jan. 27, 2020

(87) PCT Pub. No.: WO2019/023559
PCT Pub. Date: Jan. 31, 2019

(65) Prior Publication Data
US 2020/0271664 A1 Aug. 27, 2020

Related U.S. Application Data

(60) Provisional application No. 62/537,900, filed on Jul. 27, 2017.

(51) Int. Cl.
G01N 33/68 (2006.01)
C07K 14/47 (2006.01)
G01N 33/84 (2006.01)

(52) U.S. Cl.
CPC ......... *G01N 33/6872* (2013.01); *C07K 14/47* (2013.01); *G01N 33/84* (2013.01); *G01N 2500/02* (2013.01); *G01N 2500/10* (2013.01)

(58) Field of Classification Search
CPC .............. G01N 33/6872; G01N 33/84; G01N 2500/02; G01N 2500/10; C07K 14/47
See application file for complete search history.

(56) References Cited

U.S. PATENT DOCUMENTS

2009/0208946 A1 8/2009 Moyer et al.
2012/0270236 A1 10/2012 Ramsey et al.

OTHER PUBLICATIONS

Hille, B., Ionic channels of excitable membranes, 2001, pp. 1-22, Chapter 1, Sinauer Associates Inc., Sunderland, MA.
Casey, J. R., Grinstein, S. & Orlowski, J., Sensors and regulators of intracellular pH, Nat Rev Mol Cell Biol, Jan. 2010, pp. 50-61, vol. 11.
Decoursey, T. E., Voltage-gated proton channels and other proton transfer pathways, Physiol Rev, 2003, pp. 475-579, vol. 83.
Pinto, L. H., Holsinger, L. J. & Lamb, R. A., Influenza virus M2 protein has ion channel activity, Cell, May 1, 1992, pp. 517-528, vol. 69.
Mould, J. A. et al., Permeation and activation of the M2 ion channel of influenza A virus, J Biol Chem, Oct. 6, 2000, pp. 31038-21050, vol. 275(40).
Takeda, M., Pekosz, A., Shuck, K., Pinto, L. H. & Lamb, R. A., Influenza a virus M2 ion channel activity is essential for efficient replication in tissue culture, J Virol, Feb. 2002, pp. 1391-1399, vol. 76(3).
Ramsey, I. S., Moran, M. M., Chong, J. A. & Clapham, D. E., A voltage-gated proton-selective channel lacking the pore domain, Nature, Apr. 27, 2006, pp. 1213-1216, vol. 440.
Sasaki, M., Takagi, M. & Okamura, Y., A voltage sensor-domain protein is a voltage-gated proton channel, Science, Apr. 28, 2006, pp. 589-592, vol. 312.
Thomas, R. C. & Meech, R. W., Hydrogen ion currents and intracellular pH in depolarized voltage-clamped snail neurones, Nature, Oct. 1982, pp. 826-828, vol. 299.
Byerly, L., Meech, R. & Moody, W., Jr., Rapidly activating hydrogen ion currents in perfused neurones of the snail, *Lymnaea stagnalis*, J Physiol, (1984), pp. 199-216, vol. 351.
DeCoursey, T. E., Hydrogen ion currents in rat alveolar epithelial cells, Biophys J, Nov. 1991, pp. 1243-1253, vol. 60.
Capasso, M., DeCoursey, T. E. & Dyer, M. J., pH regulation and beyond: unanticipated functions for the voltage-gated proton channel, HVCN1, Trends Cell Biol, Jan. 2011, pp. 20-28, vol. 21(1).
Morgan, D. et al., Voltage-gated proton channels maintain pH in human neutrophils during phagocytosis, PNAS, Oct. 20, 2009, pp. 18022-10827, vol. 106.
Lishko, P. V., Botchkina, I. L., Fedorenko, A. & Kirichok, Y., Acid extrusion from human spermatozoa is mediated by flagellar voltage-gated proton channel, Cell, Feb. 5, 2010, pp. 327-337, vol. 140.
Wu, L. J. et al., The voltage-gated proton channel Hv1 enhances brain damage from ischemic stroke, Nat Neurosci, Oct. 1, 2012, pp. 565-573, vol. 15(4).
DeCoursey, T. E., Voltage-gated proton channels: molecular biology, physiology, and pathophysiology of the H(V) family, Physiol Rev, 2013, pp. 599-652, vol. 93.
Ramsey, I. S., Ruchti, E., Kaczmarek, J. S. & Clapham, D. E., Hv1 proton channels are required for high-level NADPH oxidase-dependent superoxide production during the phagocyte respiratory burst, PNAS, May 5, 2009, pp. 7642-7647, vol. 106(18).
DeCoursey, T. E. & Hosler, J., Philosophy of voltage-gated proton channels, J R Soc Interface, 2014, pp. 1-22, vol. 11, 20130799.
Smith, S. M. et al., Voltage-gated proton channel in a dinoflagellate, PNAS, Nov. 1, 2011, pp. 18162-18167, vol. 108(44).
Chang, R. B., Waters, H. & Liman, E. R., A proton current drives action potentials in genetically identified sour taste cells, PNAS, Dec. 21, 2010, pp. 22320-22325, vol. 107(51).
Bushman, J. D., Ye, W. & Liman, E. R., A proton current associated with sour taste: distribution and functional properties. FASEB Journal, (2015), pp. 3014-3026, vol. 29.

(Continued)

*Primary Examiner* — Robert S Landsman
(74) *Attorney, Agent, or Firm* — Pillsbury Winthrop Shaw Pittman LLP

(57) ABSTRACT

Presented herein are compositions and devices comprising otopetrin polypeptides and uses thereof for identifying modulators of proton translocation activity through an otopetrin polypeptide, or functional portion thereof.

16 Claims, 40 Drawing Sheets

Specification includes a Sequence Listing.

(56) References Cited

OTHER PUBLICATIONS

Clapp, T. R., Medler, K. F., Damak, S., Margolskee, R. F. & Kinnamon, S. C., Mouse taste cells with G protein-coupled taste receptors lack voltage-gated calcium channels and SNAP-25, BMC Biol, Mar. 30, 2006, pp. 1-9, vol. 4(7).

Zhang, Z., Zhao, Z., Margolskee, R. & Liman, E. The transduction channel TRPM5 is gated by intracellular calcium in taste cells, J Neurosci, May 23, 2007, pp. 5777-5786, vol. 27(21).

Tang, F. et al., RNA-Seq analysis to capture the transcriptome landscape of a single cell. Nature Protoc, Mar. 2010, pp. 516-535, vol. 5(3).

Zhou, T., Chien, M. S., Kaleem, S. & Matsunami, H., Single cell transcriptome analysis of mouse carotid body glomus cells, J Physiol, Mar. 4, 2016, pp. 4225-4251, 594.15.

Chaudhari, N. & Roper, S. D., The cell biology of taste, J Cell Biol, 2010, pp. 285-296, vol. 190(3).

Picelli, S. et al., Full-length RNA-seq from single cells using Smart-seq2, Nature Protocols, 2014, pp. 171-181, vol. 9(1).

Hughes, I. et al. Identification of the Otopetrin Domain, a conserved domain in vertebrate otopetrins and invertebrate otopetrin-like family members, BMC Evol Biol, Feb. 6, 2008, pp. 1-10, vol. 8(41).

Kim, E. et al., Regulation of cellular calcium in vestibular supporting cells by otopetrin 1, J Neurophysiol, Jun. 16, 2010, pp. 3439-3450, vol. 104.

Chizhmakov, I. V. et al., Selective proton permeability and pH regulation of the influenza virus M2 channel expressed in mouse erythroleukaemia cells, J Physiol, 1196, pp. 329-336, vol. 494.2.

Cherny, V. V. & DeCoursey, T. E., pH-dependent inhibition of voltage-gated H(+) currents in rat alveolar epithelial cells by Zn(2+) and other divalent cations, J Gen Physiol, Dec. 1999, pp. 819-838, vol. 114.

Takeshita, K. et al., X-ray crystal structure of voltage-gated proton channel, Nat Struct Mol Biol, Apr. 2014, pp. 352-357, vol. 21(4).

Hurle, B. et al. Non-syndromic vestibular disorder with otoconial agenesis in tilted/mergulhador mice caused by mutations in otopetrin 1, Hum Mol Genet, 2003, pp. 777-789, vol. 12(7).

Kim, E. et al. Missense mutations in Otopetrin 1 affect subcellular localization and inhibition of purinergic signaling in vestibular supporting cells, Mol Cell Neurosci, Mar. 2011, pp. 655-661, vol. 46(3).

Wu, C. et al., BioGPS: an extensible and customizable portal for querying and organizing gene annotation resources, Genome Biol, Nov. 17, 2009, pp. 1-8, vol. 10(1), Article R130.

Wang, G. X. et al., Otopetrin 1 protects mice from obesity-associated metabolic dysfunction through attenuating adipose tissue inflammation, Diabetes, 2014, pp. 1340-1352, vol. 63.

Cichy, A. et al., Extracellular pH regulates excitability of vomeronasal sensory neurons, J Neurosci, Mar. 4, 2015, pp. 4025-4039, vol. 35(9).

Wang, T. M., Holzhausen, L. C. & Kramer, R. H., Imaging an optogenetic pH sensor reveals that protons mediate lateral inhibition in the retina, Nat Neurosci, Feb. 2014, pp. 262-268, vol. 17(2).

Walther, L. E., Blodow, A., Buder, J. & Kniep, R., Principles of calcite dissolution in human and artificial otoconia, PLoS One, Jul. 21, 2014, pp. 1-9, e102516, vol. 9(7).

Lundberg, Y. W., Xu, Y., Thiessen, K. D. & Kramer, K. L., Mechanisms of otoconia and otolith development, Dev Dyn, Mar. 1, 2016, pp. 239-253, vol. 244(3).

Graze, R. M. et al., Allelic imbalance in *Drosophila* hybrid heads: exons, isoforms, and evolution, Mol Biol Evol, Jan. 7, 2012, pp. 1521-1532, vol. 29(6).

Liman, E. R., Tytgat, J. & Hess, P., Subunit stoichiometry of a mammalian K+ channel determined by construction of multimeric cDNAs, Neuron, Nov. 1992, pp. 861-871, vol. 9.

Faria, D. et al., The calcium-activated chloride channel Anoctamin 1 contributes to the regulation of renal function, Kidney Int, Jan. 29, 2014, pp. 1369-1381, vol. 85.

European Patent Office, Extended European Search Report issued in European Patent Application No. 18837315.3, dated Mar. 26, 2021, pp. 1-9.

Hughes et al., "Otopetrin 1 activation 12-15 by purinergic nucleotides regulates intracellular calcium" Proceedings of the National Academy of Sciences, Jul. 17, 2007, pp. 12023-12028 and supplemental information 1-10, vol. 104(29).

Suzuki et al., "Microtechnologies for membrane protein studies", Analytical and Bioanalvtical Chemistry, Mar. 12, 2008, pp. 2695-2702, vol. 391(8).

Tu et al. "An evolutionarily conserved gene family encodes proton-selective ion channels", Science, Mar. 2, 2018, pp. 1047-1050, vol. 359(6379).

Zhu, G., Zhang, Y., Xu, H. & Jiang, C., Identification of endogenous outward currents in the human embryonic kidney (HEK 293) cell line, J Neurosci Methods, 1998, pp. 73-83, vol. 81.

Neher, E., Correction for liquid junction potentials in patch clamp experiments, Methods Enzymol, 1992, pp. 123-131, vol. 207.

Ye, W. et al., The K+ channel KIR2.1 functions in tandem with proton influx to mediate sour taste transduction, PNAS, Dec. 1, 2015, E229-238.

Perriere, G. & Gouy, M., WWW-query: an on-line retrieval system for biological sequence banks, Biochimie, 1996, pp. 364-369, vol. 78.

Wang, Y. Y., Chang, R. B., Waters, H. N., McKemy, D. D. & Liman, E. R., The nociceptor ion channel An Otopetrin Polypeptide is potentiated and inactivated by permeating calcium ions, J Biol Chem, Nov. 21, 2008, pp. 32691-32703, vol. 283(47).

Schroeder, B. C., Cheng, T., Jan, Y. N. & Jan, L. Y., Expression cloning of TMEM16A as acalcium-activated chloride channel subunit, Cell, Sep. 19, 2008, pp. 1019-1039, vol. 134(6).

Patent Cooperation Treaty, International Search Report for PCT/US2018/044058, dated Nov. 29, 2018, pp. 1-5.

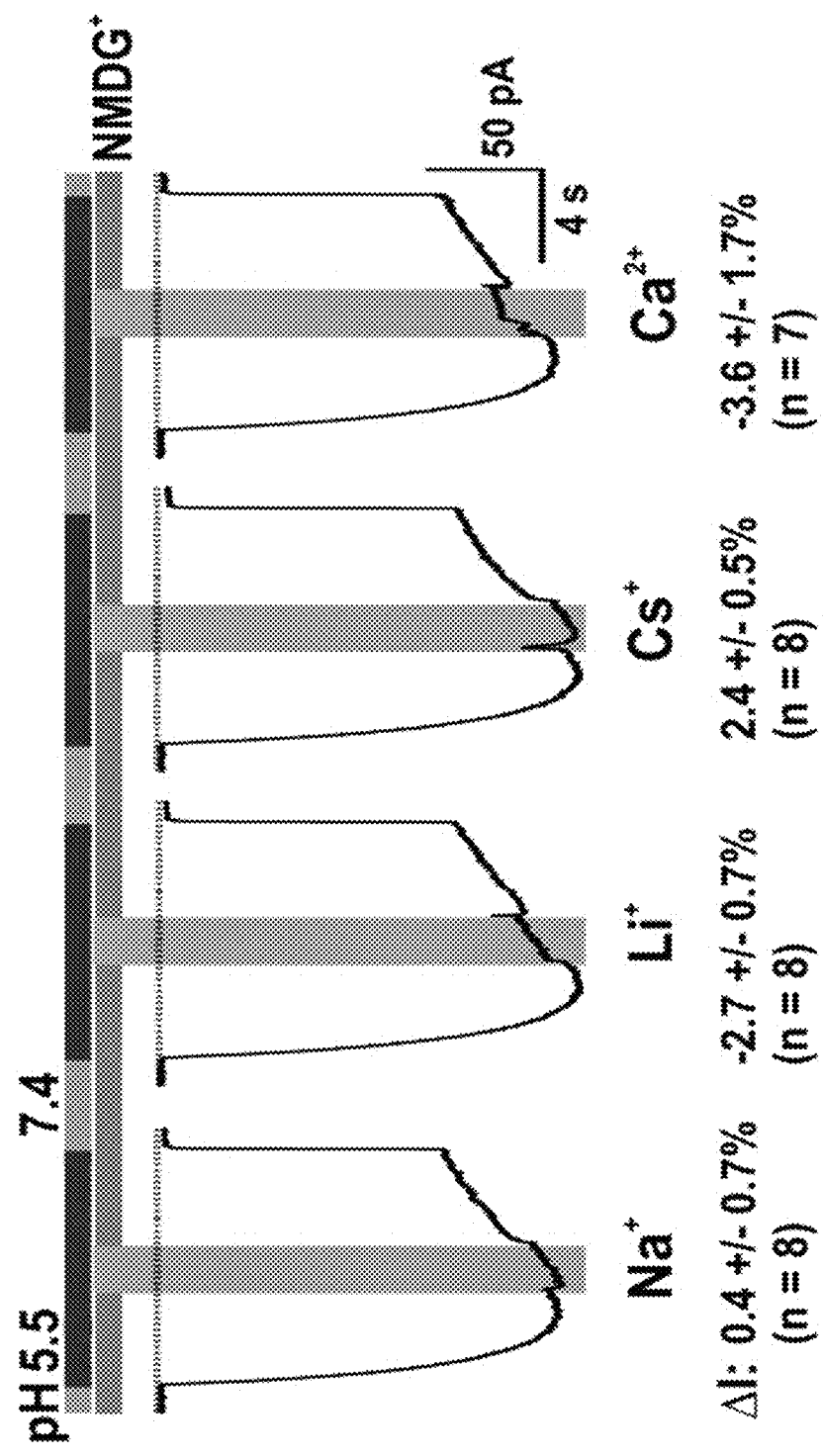

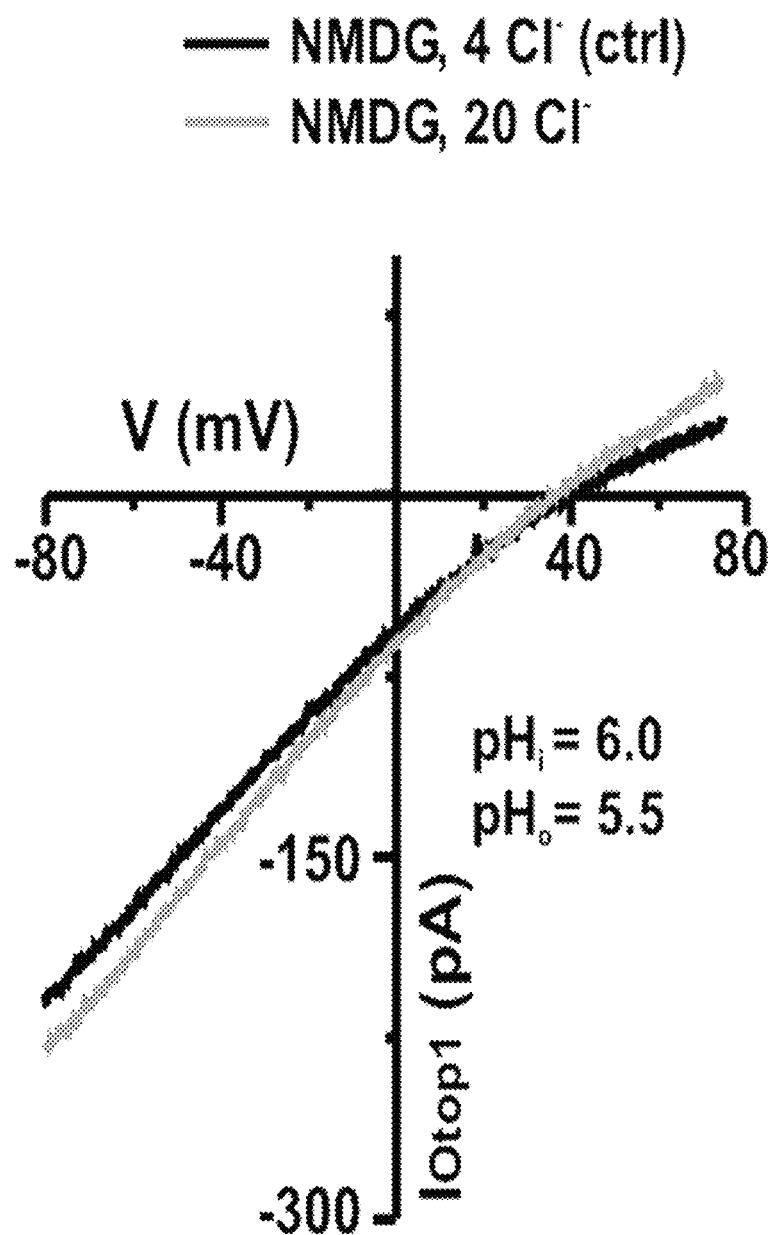

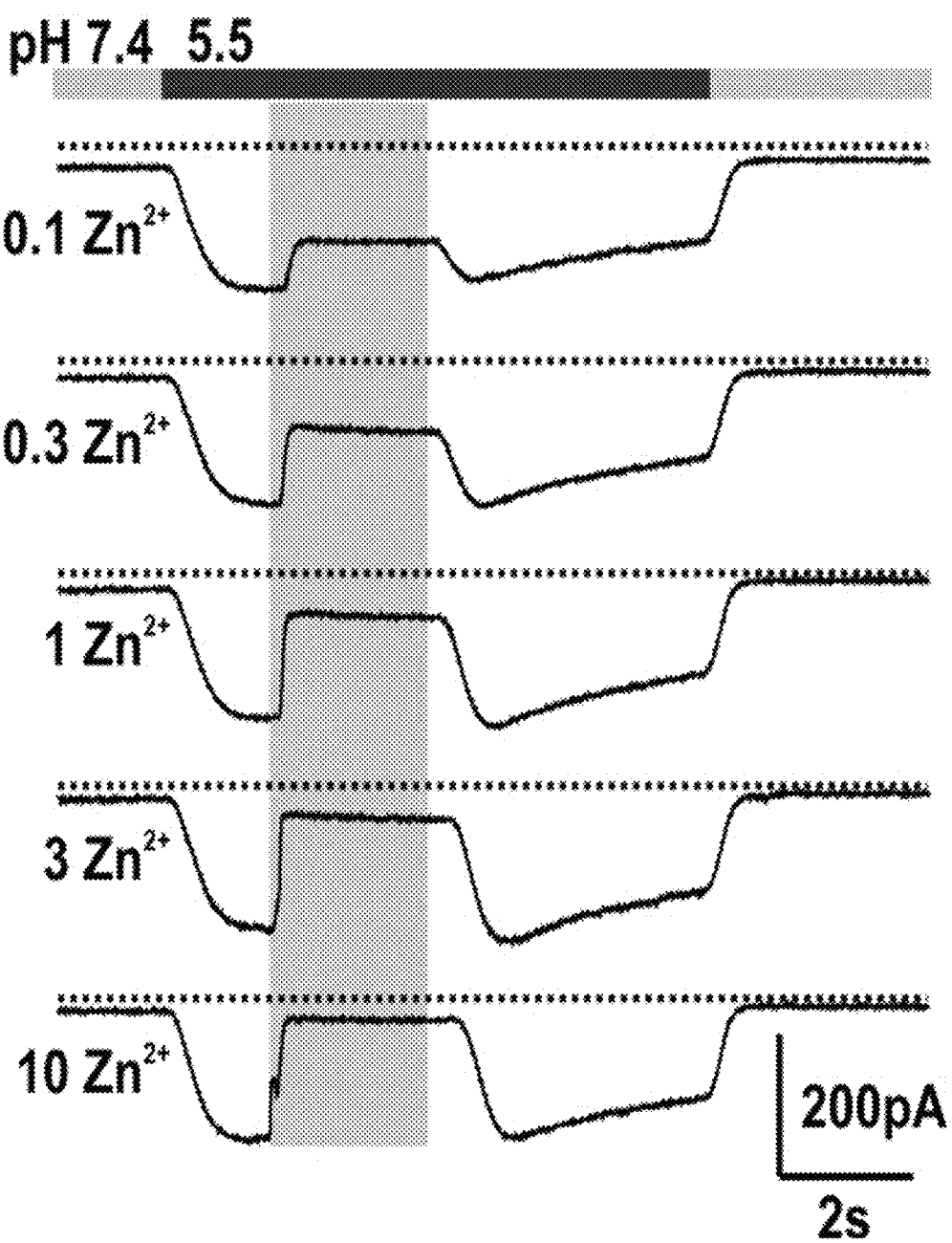

SEQUENCE LISTING

```
<160> NUMBER OF SEQ ID NOS: 9

<210> SEQ ID NO 1
<211> LENGTH: 612
<212> TYPE: PRT
<213> ORGANISM: Homo sapiens

<400> SEQUENCE: 1

Met Leu Glu Gly Leu Gly Ser Pro Ala Ser Pro Arg Ala Ala Ala Ser
1               5                   10                  15

Ala Ser Val Ala Gly Ser Ser Gly Pro Ala Ala Cys Ser Pro Pro Ser
            20                  25                  30

Ser Ser Ala Pro Arg Ser Pro Glu Ser Pro Ala Pro Arg Arg Gly Gly
        35                  40                  45

Val Arg Ala Ser Val Pro Gln Lys Leu Ala Glu Met Leu Ser Ser Gln
    50                  55                  60

Tyr Gly Leu Ile Val Phe Val Ala Gly Leu Leu Leu Leu Leu Ala Trp
65                  70                  75                  80

Ala Val His Ala Ala Gly Val Ser Lys Ser Asp Leu Leu Cys Phe Leu
                85                  90                  95

Thr Ala Leu Met Leu Leu Gln Leu Leu Trp Met Leu Trp Tyr Val Gly
                100                 105                 110

Arg Ser Ser Ala His Arg Arg Leu Phe Arg Leu Lys Asp Thr His Ala
            115                 120                 125

Gly Ala Gly Trp Leu Arg Gly Ser Ile Thr Leu Phe Ala Val Ile Thr
        130                 135                 140

Val Ile Leu Gly Cys Leu Lys Ile Gly Tyr Phe Ile Gly Phe Ser Glu
145                 150                 155                 160

Cys Leu Ser Ala Thr Glu Gly Val Phe Pro Val Thr His Ser Val His
                165                 170                 175

Thr Leu Leu Gln Val Tyr Phe Leu Trp Gly His Ala Lys Asp Ile Ile
            180                 185                 190

Gln Ser Phe Lys Thr Leu Glu Arg Phe Gly Val Ile His Ser Val Phe
        195                 200                 205

Thr Asn Leu Leu Leu Trp Ala Asn Gly Val Leu Asn Glu Ser Lys His
    210                 215                 220

Gln Leu Asn Glu His Lys Glu Arg Leu Ile Thr Leu Gly Phe Gly Asn
225                 230                 235                 240

Ile Thr Thr Val Leu Asp Asp His Thr Pro Gln Cys Asn Cys Thr Pro
                245                 250                 255
```

```
Pro Thr Leu Cys Thr Ala Ile Ser His Gly Ile Tyr Tyr Leu Tyr Pro
            260                 265                 270
Phe Asn Ile Glu Tyr Gln Ile Leu Ala Ser Thr Met Leu Tyr Val Leu
        275                 280                 285
Trp Lys Asn Ile Gly Arg Lys Val Asp Ser His Gln His Gln Lys Met
290                 295                 300
Gln Phe Lys Ser Asp Gly Val Met Val Gly Ala Val Leu Gly Leu Thr
305                 310                 315                 320
Val Leu Ala Ala Thr Ile Ala Val Val Val Tyr Leu Ile His Ile
                325                 330                 335
Gly Arg Ser Lys Thr Lys Ser Glu Ser Ala Leu Ile Met Phe Tyr Leu
            340                 345                 350
Tyr Ala Ile Thr Leu Leu Met Leu Met Gly Ala Ala Gly Leu Ala Gly
            355                 360                 365
Ile Arg Ile Tyr Arg Ile Asp Glu Lys Ser Leu Asp Glu Ser Lys Asn
        370                 375                 380
Pro Ala Arg Lys Leu Asp Ser Asp Leu Leu Val Gly Thr Ala Ser Gly
385                 390                 395                 400
Ser Trp Leu Ile Ser Trp Gly Ser Ile Leu Ala Ile Leu Cys Ala Glu
                405                 410                 415
Gly His Pro Arg Tyr Thr Trp Tyr Asn Leu Pro Tyr Ser Ile Leu Ala
                420                 425                 430
Ile Val Glu Lys Tyr Ile Gln Asn Leu Phe Ile Phe Glu Ser Ile His
            435                 440                 445
Arg Glu Pro Glu Lys Leu Ser Glu Asp Ile Gln Thr Leu Arg Val Val
        450                 455                 460
Thr Val Cys Asn Gly Asn Thr Met Pro Leu Ala Ser Ser Cys Pro Lys
465                 470                 475                 480
Ser Gly Gly Val Ala Arg Asp Val Ala Pro Gln Gly Lys Asp Met Pro
                485                 490                 495
Pro Ala Ala Asn Gly Asn Val Cys Met Arg Glu Ser His Asp Lys Glu
                500                 505                 510
Glu Glu Lys Gln Glu Glu Ser Ser Trp Gly Gly Ser Pro Ser Pro Val
            515                 520                 525
Arg Leu Pro Arg Phe Leu Gln Gly Asn Ala Lys Arg Lys Val Leu Arg
        530                 535                 540
Asn Ile Ala Ala Phe Leu Phe Leu Cys Asn Ile Ser Leu Trp Ile Pro
545                 550                 555                 560
Pro Ala Phe Gly Cys Arg Pro Glu Tyr Asp Asn Gly Leu Glu Glu Ile
                565                 570                 575
Val Phe Gly Phe Glu Pro Trp Ile Ile Val Val Asn Leu Ala Met Pro
            580                 585                 590
Phe Ser Ile Phe Tyr Arg Met His Ala Ala Ala Ser Leu Phe Glu Val
            595                 600                 605
Tyr Cys Lys Ile
    610

<210> SEQ ID NO 2
<211> LENGTH: 562
<212> TYPE: PRT
<213> ORGANISM: Homo sapiens

<400> SEQUENCE: 2

Met Ser Glu Glu Leu Ala Gln Gly Pro Lys Glu Ser Pro Pro Ala Pro
```

```
1               5                   10                  15
Arg Ala Gly Pro Arg Glu Val Trp Lys Lys Gly Arg Leu Leu Ser
                20                  25                  30

Val Leu Leu Ala Val Asn Val Leu Leu Ala Cys Thr Leu Ile Ser
                35                  40                  45

Gly Gly Ala Phe Asn Lys Val Ala Val Tyr Asp Thr Asp Val Phe Ala
    50                  55                  60

Leu Leu Thr Ala Met Met Leu Leu Ala Thr Leu Trp Ile Leu Phe Tyr
65                  70                  75                  80

Leu Leu Arg Thr Val Arg Cys Pro Cys Ala Val Pro Tyr Arg Asp Ala
                85                  90                  95

His Ala Gly Pro Ile Trp Leu Arg Gly Leu Val Leu Phe Gly Ile
                100                 105                 110

Cys Thr Leu Ile Met Asp Val Phe Lys Thr Gly Tyr Tyr Ser Ser Phe
    115                 120                 125

Phe Glu Cys Gln Ser Ala Ile Lys Ile Leu His Pro Leu Ile Gln Ala
    130                 135                 140

Val Phe Val Ile Ile Gln Thr Tyr Phe Leu Trp Val Ser Ala Lys Asp
145                 150                 155                 160

Cys Val His Val His Leu Asp Leu Thr Trp Cys Gly Leu Met Phe Thr
                165                 170                 175

Leu Thr Thr Asn Leu Ala Ile Trp Met Ala Ala Val Val Asp Glu Ser
                180                 185                 190

Val His Gln Ser His Ser Tyr Ser Ser Ser His Ser Asn Ala Ser His
                195                 200                 205

Ala Arg Leu Ile Ser Asp Gln His Ala Asp Asn Pro Val Gly Gly Asp
                210                 215                 220

Ser Cys Leu Cys Ser Thr Ala Val Cys Gln Ile Phe Gln Gln Gly Tyr
225                 230                 235                 240

Phe Tyr Leu Tyr Pro Phe Asn Ile Glu Tyr Ser Leu Phe Ala Ser Thr
                245                 250                 255

Met Leu Tyr Val Met Trp Lys Asn Val Gly Arg Phe Leu Ala Ser Thr
                260                 265                 270

Pro Gly His Ser His Thr Pro Thr Pro Val Ser Leu Phe Arg Glu Thr
                275                 280                 285

Phe Phe Ala Gly Pro Val Leu Gly Leu Leu Phe Val Val Gly Leu
                290                 295                 300

Ala Val Phe Ile Ile Tyr Glu Val Gln Val Ser Gly Asp Gly Ser Arg
305                 310                 315                 320

Thr Arg Gln Ala Leu Val Ile Tyr Tyr Ser Phe Asn Ile Val Cys Leu
                325                 330                 335

Gly Leu Thr Thr Leu Val Ser Leu Ser Gly Ser Ile Ile Tyr Arg Phe
                340                 345                 350

Asp Arg Arg Ala Met Asp His His Lys Asn Pro Thr Arg Thr Leu Asp
                355                 360                 365

Val Ala Leu Leu Met Gly Ala Ala Leu Gly Gln Tyr Ala Ile Ser Tyr
                370                 375                 380

Tyr Ser Ile Val Ala Val Val Ala Gly Thr Pro Gln Asp Leu Leu Ala
385                 390                 395                 400

Gly Leu Asn Leu Thr His Ala Leu Leu Met Ile Ala Gln His Thr Phe
                405                 410                 415

Gln Asn Met Phe Ile Ile Glu Ser Leu His Arg Gly Pro Pro Gly Ala
                420                 425                 430
```

Glu Pro His Ser Thr His Pro Lys Glu Pro Cys Gln Asp Leu Thr Phe
    435                 440                 445

Thr Asn Leu Asp Ala Leu His Thr Leu Ser Ala Cys Pro Pro Asn Pro
450                 455                 460

Gly Leu Val Ser Pro Ser Pro Ser Asp Gln Arg Glu Ala Val Ala Ile
465                 470                 475                 480

Val Ser Thr Pro Arg Ser Gln Trp Arg Gln Cys Leu Lys Asp Ile
                485                 490                 495

Ser Leu Phe Leu Leu Leu Cys Asn Val Ile Leu Trp Ile Met Pro Ala
            500                 505                 510

Phe Gly Ala Arg Pro His Phe Ser Asn Thr Val Glu Val Asp Phe Tyr
            515                 520                 525

Gly Tyr Ser Leu Trp Ala Val Ile Val Asn Ile Cys Leu Pro Phe Gly
            530                 535                 540

Ile Phe Tyr Arg Met His Ala Val Ser Ser Leu Leu Glu Val Tyr Val
545                 550                 555                 560

Leu Ser

<210> SEQ ID NO 3
<211> LENGTH: 596
<212> TYPE: PRT
<213> ORGANISM: Homo sapiens

<400> SEQUENCE: 3

Met Gly Arg Gly Ala Arg Ala Ala Ala Gln Ser Arg Trp Gly Arg
1               5                   10                  15

Ala Ser Arg Ala Ser Val Ser Pro Gly Arg Thr Ile Arg Ser Ala Pro
                20                  25                  30

Ala Val Gly Glu Ala Gln Glu Thr Glu Ala Ala Pro Glu Lys Glu Asn
            35                  40                  45

Arg Val Asp Val Gly Ala Glu Glu Arg Ala Ala Thr Arg Pro Arg
50                  55                  60

Gln Lys Ser Trp Leu Val Arg His Phe Ser Leu Leu Arg Arg Asp
65                  70                  75                  80

Arg Gln Ala Gln Lys Ala Gly Gln Leu Phe Ser Gly Leu Leu Ala Leu
                85                  90                  95

Asn Val Val Phe Leu Gly Gly Ala Phe Ile Cys Ser Met Ile Phe Asn
            100                 105                 110

Lys Val Ala Val Thr Leu Gly Asp Val Trp Ile Leu Leu Ala Thr Leu
            115                 120                 125

Lys Val Leu Ser Leu Leu Trp Leu Leu Tyr Tyr Val Ala Ser Thr Thr
130                 135                 140

Arg Arg Pro His Ala Val Leu Tyr Gln Asp Pro His Ala Gly Pro Leu
145                 150                 155                 160

Trp Val Arg Gly Ser Leu Val Leu Phe Gly Ser Cys Thr Phe Cys Leu
                165                 170                 175

Asn Ile Phe Arg Val Gly Tyr Asp Val Ser His Ile Arg Cys Lys Ser
            180                 185                 190

Gln Leu Asp Leu Val Phe Ser Val Ile Glu Met Val Phe Ile Gly Val
            195                 200                 205

Gln Thr Trp Val Leu Trp Lys His Cys Lys Asp Cys Val Arg Val Gln
            210                 215                 220

Thr Asn Phe Thr Arg Cys Gly Leu Met Leu Thr Leu Ala Thr Asn Leu
225                 230                 235                 240

```
Leu Leu Trp Val Leu Ala Val Thr Asn Asp Ser Met His Arg Glu Ile
            245                 250                 255

Glu Ala Glu Leu Gly Ile Leu Met Glu Lys Ser Thr Gly Asn Glu Thr
            260                 265                 270

Asn Thr Cys Leu Cys Leu Asn Ala Thr Ala Cys Glu Ala Phe Arg Arg
            275                 280                 285

Gly Phe Leu Met Leu Tyr Pro Phe Ser Thr Glu Tyr Cys Leu Ile Cys
            290                 295                 300

Cys Ala Val Leu Phe Val Met Trp Lys Asn Val Gly Arg His Val Ala
305                 310                 315                 320

Pro His Met Gly Ala His Pro Ala Thr Ala Pro Phe His Leu His Gly
            325                 330                 335

Ala Ile Phe Gly Pro Leu Leu Gly Leu Leu Val Leu Leu Ala Gly Val
            340                 345                 350

Cys Val Phe Val Leu Phe Gln Ile Glu Ala Ser Gly Pro Ala Ile Ala
            355                 360                 365

Cys Gln Tyr Phe Thr Leu Tyr Tyr Ala Phe Tyr Val Ala Val Leu Pro
            370                 375                 380

Thr Met Ser Leu Ala Cys Leu Ala Gly Thr Ala Ile His Gly Leu Glu
385                 390                 395                 400

Glu Arg Glu Leu Asp Thr Val Lys Asn Pro Thr Arg Ser Leu Asp Val
            405                 410                 415

Val Leu Leu Met Gly Ala Ala Leu Gly Gln Met Gly Ile Ala Tyr Phe
            420                 425                 430

Ser Ile Val Ala Ile Val Ala Lys Arg Pro His Glu Leu Asn Arg
            435                 440                 445

Leu Ile Leu Ala Tyr Ser Leu Leu Ile Leu Gln His Ile Ala Gln
            450                 455                 460

Asn Leu Phe Ile Ile Glu Gly Leu His Arg Arg Pro Leu Trp Glu Thr
465                 470                 475                 480

Val Pro Glu Gly Leu Ala Gly Lys Gln Glu Ala Pro Pro Arg Arg
            485                 490                 495

Gly Ser Leu Leu Glu Leu Gly Gln Gly Leu Gln Arg Ala Ser Leu Ala
            500                 505                 510

Tyr Ile His Ser Tyr Ser His Leu Asn Trp Lys Arg Arg Ala Leu Lys
            515                 520                 525

Glu Ile Ser Leu Phe Leu Ile Leu Cys Asn Ile Thr Leu Trp Met Met
            530                 535                 540

Pro Ala Phe Gly Ile His Pro Glu Phe Glu Asn Gly Leu Glu Lys Asp
545                 550                 555                 560

Phe Tyr Gly Tyr Gln Ile Trp Phe Ala Ile Val Asn Phe Gly Leu Pro
            565                 570                 575

Leu Gly Val Phe Tyr Arg Met His Ser Val Gly Gly Leu Val Glu Val
            580                 585                 590

Tyr Leu Gly Ala
            595

<210> SEQ ID NO 4
<211> LENGTH: 600
<212> TYPE: PRT
<213> ORGANISM: Mus musculus

<400> SEQUENCE: 4

Met Pro Gly Gly Pro Gly Ala Pro Ser Ser Pro Ala Ala Ser Ser Gly
```

-continued

```
1               5               10              15
Ser Ser Arg Ala Ala Pro Ser Gly Ile Ala Ala Cys Pro Leu Ser Pro
                20              25              30

Pro Pro Leu Ala Arg Gly Ser Pro Gln Ala Ser Gly Pro Arg Arg Gly
                35              40              45

Ala Ser Val Pro Gln Lys Leu Ala Glu Thr Leu Ser Ser Gln Tyr Gly
                50              55              60

Leu Asn Val Phe Val Ala Gly Leu Leu Phe Leu Leu Ala Trp Ala Val
65              70              75              80

His Ala Thr Gly Val Gly Lys Ser Asp Leu Leu Cys Val Leu Thr Ala
                85              90              95

Leu Met Leu Leu Gln Leu Leu Trp Met Leu Trp Tyr Val Gly Arg Ser
                100             105             110

Tyr Met Gln Arg Arg Leu Ile Arg Pro Lys Asp Thr His Ala Gly Ala
                115             120             125

Arg Trp Leu Arg Gly Ser Ile Thr Leu Phe Ala Phe Ile Thr Val Val
                130             135             140

Leu Gly Cys Leu Lys Val Ala Tyr Phe Ile Gly Phe Ser Glu Cys Leu
145             150             155             160

Ser Ala Thr Glu Gly Val Phe Pro Val Thr His Ala Val His Thr Leu
                165             170             175

Leu Gln Val Tyr Phe Leu Trp Gly His Ala Lys Asp Ile Ile Met Ser
                180             185             190

Phe Lys Thr Leu Glu Arg Phe Gly Val Ile His Ser Val Phe Thr Asn
                195             200             205

Leu Leu Leu Trp Ala Asn Ser Val Leu Asn Glu Ser Lys His Gln Leu
                210             215             220

Asn Glu His Lys Glu Arg Leu Ile Thr Leu Gly Phe Gly Asn Ile Thr
225             230             235             240

Ile Val Leu Asp Asp His Thr Pro Gln Cys Asn Cys Thr Pro Pro Ala
                245             250             255

Leu Cys Ser Ala Leu Ser His Gly Ile Tyr Tyr Leu Tyr Pro Phe Asn
                260             265             270

Ile Glu Tyr Gln Ile Leu Ala Ser Thr Met Leu Tyr Val Leu Trp Lys
                275             280             285

Asn Ile Gly Arg Arg Val Asp Ser Ser Gln His Gln Lys Met Gln Cys
                290             295             300

Arg Phe Asp Gly Val Leu Val Gly Ser Val Leu Gly Leu Thr Val Leu
305             310             315             320

Ala Ala Thr Ile Ala Val Val Val Tyr Met Ile His Ile Gly Arg
                325             330             335

Ser Lys Ser Lys Ser Glu Ser Ala Leu Ile Met Phe Tyr Leu Tyr Ala
                340             345             350

Ile Thr Val Leu Leu Leu Met Gly Ala Ala Gly Leu Val Gly Ser Trp
                355             360             365

Ile Tyr Arg Val Asp Glu Lys Ser Leu Asp Glu Ser Lys Asn Pro Ala
                370             375             380

Arg Lys Leu Asp Val Asp Leu Leu Val Ala Thr Ala Ser Gly Ser Trp
385             390             395             400

Leu Leu Ser Trp Gly Ser Ile Leu Ala Ile Ala Cys Ala Glu Thr Arg
                405             410             415

Pro Pro Tyr Thr Trp Tyr Asn Leu Pro Tyr Ser Val Leu Val Ile Val
                420             425             430
```

-continued

Glu Lys Tyr Val Gln Asn Ile Phe Ile Ile Glu Ser Val His Leu Glu
        435                 440                 445

Pro Glu Gly Val Pro Glu Asp Val Arg Thr Leu Arg Val Val Thr Val
450                 455                 460

Cys Ser Ser Glu Ala Ala Ala Leu Ala Ala Ser Thr Leu Gly Ser Gln
465                 470                 475                 480

Gly Met Ala Gln Asp Gly Ser Pro Ala Val Asn Gly Asn Leu Cys Leu
                485                 490                 495

Gln Gln Arg Cys Gly Lys Glu Asp Gln Glu Ser Gly Trp Glu Gly Ala
            500                 505                 510

Thr Gly Thr Thr Arg Cys Leu Asp Phe Leu Gln Gly Gly Met Lys Arg
        515                 520                 525

Arg Leu Leu Arg Asn Ile Thr Ala Phe Leu Phe Leu Cys Asn Ile Ser
    530                 535                 540

Leu Trp Ile Pro Pro Ala Phe Gly Cys Arg Pro Glu Tyr Asp Asn Gly
545                 550                 555                 560

Leu Glu Glu Ile Val Phe Gly Phe Glu Pro Trp Ile Ile Val Val Asn
                565                 570                 575

Leu Ala Met Pro Phe Ser Ile Phe Tyr Arg Met His Ala Ala Ala Ala
                580                 585                 590

Leu Phe Glu Val Tyr Cys Lys Ile
            595                 600

<210> SEQ ID NO 5
<211> LENGTH: 563
<212> TYPE: PRT
<213> ORGANISM: Mus musculus

<400> SEQUENCE: 5

Met Ser Glu Glu Leu Val Pro His Pro Asn Glu Ser Leu Pro Gly Pro
1               5                   10                  15

Arg Ala Ser Pro Arg Glu Val Trp Lys Lys Gly Gly Arg Leu Leu Ser
            20                  25                  30

Val Leu Leu Ala Val Asn Val Leu Leu Leu Ala Cys Thr Leu Ile Ser
        35                  40                  45

Gly Gly Ala Phe Asn Lys Val Ala Val Tyr Asp Thr Asp Val Phe Ala
    50                  55                  60

Leu Leu Thr Thr Met Met Leu Leu Ala Ala Leu Trp Ile Val Phe Tyr
65                  70                  75                  80

Leu Leu Arg Thr Ala Arg Cys Pro Asp Ala Val Pro Tyr Arg Asp Ala
                85                  90                  95

His Ala Gly Pro Ile Trp Leu Arg Gly Gly Leu Val Leu Phe Gly Ile
            100                 105                 110

Cys Thr Leu Val Met Asp Val Phe Lys Thr Gly Tyr Tyr Ser Ser Phe
        115                 120                 125

Phe Glu Cys Gln Ser Ala Ile Lys Ile Leu His Pro Ile Ile Gln Ala
    130                 135                 140

Val Phe Val Ile Val Gln Thr Tyr Phe Leu Trp Ile Ser Ala Lys Asp
145                 150                 155                 160

Cys Ile His Thr His Leu Asp Leu Thr Arg Cys Gly Leu Met Phe Thr
                165                 170                 175

Leu Ala Thr Asn Leu Ala Ile Trp Met Ala Val Val Asp Glu Ser
            180                 185                 190

Val His Gln Ala His Ser Tyr Ser Gly Ser His Gly Asn Thr Ser His

```
                        195                 200                 205
Thr Arg Leu Asn Pro Asp Ser Lys Arg Ala Gly Gly Ala Ala Glu Glu
210                 215                 220

Asp Pro Cys Leu Cys Ser Thr Ala Ile Cys Gln Ile Phe Gln Gln Gly
225                 230                 235                 240

Tyr Phe Tyr Leu Tyr Pro Phe Asn Ile Glu Tyr Ser Leu Phe Ala Ser
                245                 250                 255

Thr Met Leu Tyr Val Met Trp Lys Asn Val Gly Arg Leu Leu Ala Ser
            260                 265                 270

Thr His Gly His Gly His Thr Pro Ser Arg Val Ser Leu Phe Arg Glu
        275                 280                 285

Thr Phe Phe Ala Gly Pro Val Leu Gly Leu Leu Phe Val Val Gly
290                 295                 300

Leu Ala Val Phe Ile Leu Tyr Glu Val Gln Val Ser Gly Glu Arg Gly
305                 310                 315                 320

His Thr Arg Gln Ala Leu Val Ile Tyr Tyr Ser Phe Asn Ile Val Cys
                325                 330                 335

Leu Gly Leu Met Thr Leu Val Ser Leu Ser Gly Ser Val Ile Tyr Arg
            340                 345                 350

Phe Asp Arg Arg Ala Met Asp His His Lys Asn Pro Thr Arg Thr Leu
        355                 360                 365

Asp Val Ala Leu Leu Met Gly Ala Ala Leu Gly Gln Tyr Ala Ile Ser
370                 375                 380

Tyr Tyr Ser Ile Val Ala Val Val Gly Ser Pro Arg Asp Leu Gln
385                 390                 395                 400

Gly Ala Leu Asn Leu Ser His Ala Leu Leu Met Ile Ala Gln His Thr
                405                 410                 415

Phe Gln Asn Val Phe Ile Ile Glu Ser Leu His Arg Gly Pro Pro Gly
            420                 425                 430

Ala Glu Pro Arg Glu Met Pro Pro Lys Glu Pro Cys Gln Gly Ile Thr
        435                 440                 445

Phe Ala Asn Leu Asp Ala Ile Arg Thr Leu Pro Ser Cys Pro Pro Thr
450                 455                 460

Pro Arg Leu Val Ile Pro Asn Leu Glu Ser Pro Gln Glu Ala Val Ala
465                 470                 475                 480

Ile Ile Ser Ala Pro Arg Cys His Trp Arg Arg Arg Cys Leu Lys Asp
                485                 490                 495

Ile Ser Leu Phe Leu Leu Leu Cys Asn Val Ile Leu Trp Ile Met Pro
            500                 505                 510

Ala Phe Gly Ala Arg Pro His Phe Ser Asn Thr Val Glu Val Asp Phe
        515                 520                 525

Tyr Gly Tyr Ser Leu Trp Ala Ala Ile Val Asn Ile Cys Leu Pro Phe
530                 535                 540

Gly Ile Phe Tyr Arg Met His Ala Val Ser Ser Leu Leu Glu Val Tyr
545                 550                 555                 560

Val Leu Ser

<210> SEQ ID NO 6
<211> LENGTH: 577
<212> TYPE: PRT
<213> ORGANISM: Mus musculus

<400> SEQUENCE: 6

Met Ala Ser Gln Thr Ser Ala Pro Ala Glu Pro Ala Pro Met Pro Ser
```

```
1               5                   10                  15
Pro Glu Ala Lys Thr Thr Glu Gly Ala Ser Ser Tyr Asp Gln Ala Asp
                20                  25                  30

Met Glu Thr Lys His Ala Gly Ser Pro Cys Pro Lys Gln Lys Ser
                35                  40                  45

Trp Leu Ala Arg His Phe Ser Leu Leu Arg Arg Asp Arg Gln Ala
    50                  55                  60

Gln Lys Ala Gly Gln Leu Phe Ser Gly Leu Leu Ala Leu Asn Val Val
65                  70                  75                  80

Phe Leu Gly Gly Ala Phe Ile Cys Ser Met Ile Phe Asn Lys Val Ser
                85                  90                  95

Val Thr Leu Gly Asp Val Trp Ile Leu Leu Ala Ala Leu Lys Val Leu
                100                 105                 110

Ser Leu Leu Trp Leu Leu Tyr Tyr Thr Val Gly Thr Thr Arg Lys Pro
                115                 120                 125

His Ala Val Leu Tyr Arg Asp Pro His Ala Gly Pro Ile Trp Val Arg
                130                 135                 140

Gly Ser Leu Val Leu Phe Gly Ser Cys Thr Val Cys Leu Asn Ile Phe
145                 150                 155                 160

Arg Met Gly Tyr Asp Val Ser His Ile His Cys Lys Ser Glu Val Glu
                165                 170                 175

Leu Ile Phe Pro Ala Ile Glu Ile Val Phe Met Ile Ile Gln Thr Trp
                180                 185                 190

Val Leu Trp Arg His Cys Lys Asp Cys Val Gln Val Gln Thr Asn Phe
                195                 200                 205

Thr Arg Cys Gly Leu Met Leu Thr Leu Ala Thr Asn Leu Leu Met Trp
                210                 215                 220

Val Leu Ala Val Thr Asn Asp Ser Met His Arg Glu Ile Glu Ala Glu
225                 230                 235                 240

Leu Asp Ala Leu Met Glu Lys Phe Ser Gly Asn Gly Thr Asn Thr Cys
                245                 250                 255

Met Cys Leu Asn Thr Thr Val Cys Glu Val Phe Arg Lys Gly Tyr Leu
                260                 265                 270

Met Leu Tyr Pro Phe Ser Thr Glu Tyr Cys Leu Ile Cys Cys Ala Val
                275                 280                 285

Leu Phe Val Met Trp Lys Asn Val Ser Arg Ser Leu Ala Ala His Thr
                290                 295                 300

Gly Ala His Pro Asn Arg Ser Pro Phe Arg Leu His Gly Thr Ile Phe
305                 310                 315                 320

Gly Pro Leu Leu Gly Leu Leu Ala Leu Val Ala Gly Val Cys Val Phe
                325                 330                 335

Val Leu Phe Gln Ile Glu Ala Ser Gly Pro Asp Ile Ala Arg Gln Tyr
                340                 345                 350

Phe Thr Leu Tyr Tyr Ala Phe Tyr Val Ala Val Leu Pro Thr Met Ser
                355                 360                 365

Leu Ala Cys Leu Ala Gly Thr Ala Ile His Gly Leu Glu Glu Arg Glu
                370                 375                 380

Leu Asp Thr Leu Lys Asn Pro Thr Arg Ser Leu Asp Val Val Leu Leu
385                 390                 395                 400

Met Gly Ala Ala Leu Gly Gln Met Gly Ile Ala Tyr Phe Ser Ile Val
                405                 410                 415

Ala Ile Val Ala Thr Gln Pro His Glu Leu Leu Asn Gln Leu Ile Leu
                420                 425                 430
```

```
Ala Tyr Ser Leu Leu Leu Ile Leu Gln His Ile Thr Gln Asn Leu Phe
            435                 440                 445

Ile Ile Glu Gly Leu His Arg Arg Pro Leu Trp Glu Pro Ala Val Ser
450                 455                 460

Gly Val Met Glu Lys Gln Asp Val Glu Leu Pro Arg Arg Gly Ser Leu
465                 470                 475                 480

Arg Glu Leu Gly Gln Asp Leu Arg Arg Ala Ser Arg Ala Tyr Ile His
                485                 490                 495

Ser Phe Ser His Leu Asn Trp Lys Arg Arg Met Leu Lys Glu Ile Ser
                500                 505                 510

Leu Phe Leu Ile Leu Cys Asn Ile Thr Leu Trp Met Met Pro Ala Phe
            515                 520                 525

Gly Ile His Pro Glu Phe Glu Asn Gly Leu Glu Lys Asp Phe Tyr Gly
            530                 535                 540

Tyr Arg Thr Trp Phe Thr Ile Val Asn Phe Gly Leu Pro Leu Gly Val
545                 550                 555                 560

Phe Tyr Arg Met His Ser Val Gly Gly Leu Val Glu Val Tyr Leu Gly
                565                 570                 575

Ala

<210> SEQ ID NO 7
<211> LENGTH: 977
<212> TYPE: PRT
<213> ORGANISM: Drosophila

<400> SEQUENCE: 7

Met Gln Arg Cys Pro Tyr Ile His Glu Met Arg Glu Arg Leu Leu Asp
1               5                   10                  15

Gln Pro Arg Glu Thr Leu Gln Leu Glu Asn Met Glu Arg Ala Asn Leu
            20                  25                  30

Leu Asp Asn Arg Gln Ser Ala Ser Glu Ser Asn Gln Leu Gln Gly Asp
        35                  40                  45

Gly Tyr His Thr Ser Pro Ala His Gln Arg Thr Pro Leu Val Pro His
    50                  55                  60

Asp Leu Gly Glu Asp Phe Asn Leu Asp Phe Asp Asp Phe Pro Ile
65                  70                  75                  80

Asp Ala Arg Arg Pro Lys Asn Ala Asn Asp Ile His Pro Ala Val Leu
                85                  90                  95

Thr Arg Pro Gln Gln Arg Thr Ser Leu Phe Ile Val Thr Ser Leu Val
            100                 105                 110

Tyr Ala Ile Leu Leu Ile Val Val Cys Ile Ala Tyr Val Ile Ser Asp
        115                 120                 125

Val Thr Thr His Arg Leu Pro Val Leu Tyr Tyr Glu Thr Phe Thr
    130                 135                 140

Tyr Leu Tyr Gly Val Ser Ile Leu Phe Leu Leu Tyr Val Phe Cys Phe
145                 150                 155                 160

Leu Leu Gln Glu Ser Ser Cys Cys Asn Gly Gly Asn Gly Gly Ser Lys
                165                 170                 175

Pro Lys Pro Gln Pro Lys Glu Lys Lys Ser Lys Ala Lys Asn Ala
            180                 185                 190

Asp Pro Ala Asp Ser Lys Asp Ala Lys Gly Ser Lys Asp Ser Gly Lys
        195                 200                 205

Ala Ala Lys Gly Ala Ala Tyr Gln His Thr Leu Ala Lys Phe Leu Glu
    210                 215                 220
```

```
Ala Pro Val Asp Ala Glu Val Ala Val Thr Pro Lys Asn Val Arg Lys
225                 230                 235                 240

Arg Lys Thr Thr His Ser Asp Leu Thr His Gly Ser Phe Phe Leu Arg
            245                 250                 255

Val Gly Ala Ile Ala Phe Gly Leu Gly Ala Met Ile Tyr Ile Gly Leu
        260                 265                 270

Glu Phe Gly Ser Phe Phe Glu Ile Pro Phe Asp Ser Pro Cys His His
    275                 280                 285

Ile Leu Ile Gly Val Asn Pro Leu Leu Gln Met Ile Phe Thr Phe Met
290                 295                 300

Gln Met Tyr Phe Ile Phe Met Asn Ala Arg Thr Arg Pro Pro Phe Gln
305                 310                 315                 320

Leu Asn Ile His Arg Phe Lys Val Ile Ala Arg Phe Gly Leu Met His
                325                 330                 335

Val Val Ala Thr Asn Ile Cys Val Trp Ile Arg Thr Leu Val Lys Glu
            340                 345                 350

Ser Leu Leu Glu Ile Thr Ile Tyr His Gln Lys Asn Glu Pro Glu Ala
        355                 360                 365

Gly Ala Ser Ser Ile Ala His Ser Ile Arg Gln His Ala Leu Arg His
370                 375                 380

Ala Gly Thr Val Leu Arg Thr His Ala Gly Pro Asn Ser Glu Phe Glu
385                 390                 395                 400

Val Leu Asp Gly Glu Asp Ile Leu Pro Lys Asp Val Tyr Lys Ser Asp
                405                 410                 415

Asn Val Leu Ser Lys Leu Val Arg Asn Thr Val Asp Gly Ile Ser Lys
            420                 425                 430

Ser Leu Gly Met Gly Gly Asp Gln Ala Leu Asp Ser Ser Thr Thr Ser
        435                 440                 445

Ser Ser Thr Thr Thr Thr Thr Arg Ala Pro Phe Thr Thr Pro Asn Tyr
450                 455                 460

Gln Trp His Ser Thr Thr Met Ala Arg Lys Leu Lys Lys Phe Ile Thr
465                 470                 475                 480

Ser Ala Thr Thr Ala Ala Thr Ala Ala Gly Ser Ser Ser Thr Ala
                485                 490                 495

Ser Ser Thr Thr Thr Ile Ser Pro Thr Ile Ser Ser Thr Thr Ile Pro
        500                 505                 510

Ser Thr Thr Ile Ser Ser Thr Ile Ser Ser Thr Thr Phe Ser
        515                 520                 525

Pro Phe Ser Pro Ser Thr Thr Thr Thr Thr Thr Thr Ala Ala Ala
530                 535                 540

Leu Asn Leu Glu Thr Ser Gly Ser Glu Ser Pro Phe Gly Gly Leu Gln
545                 550                 555                 560

Arg Ile Leu Ser Ser Ala Ala Pro Pro Ser Leu Ala Pro Val Asp Gly
            565                 570                 575

Phe Gly Ser Ala Ser Ala Ala Thr Pro Thr Ser Gly Ser Gly Ala Gly
        580                 585                 590

Ser Phe Val Asp Ser Phe Leu Ala Ser Thr Leu Ser Pro Ala Ser Ser
    595                 600                 605

Thr Glu Gly Ser Ala Ser Ile Met Asn Asn Leu Phe Gly Gln Gly Pro
    610                 615                 620

Met Glu Asn Ser Phe Gln Thr Tyr Thr Asp Leu Gly His Glu Glu Ala
625                 630                 635                 640
```

```
Thr Gly Leu Val Ser Phe Glu Asn Leu Glu Ser Leu Asp Asn Ile Tyr
             645                 650                 655

Pro Ala Ala Leu Ser Ser Asn Ile Gly Thr Leu Asn Ser Thr Ala Cys
        660                 665                 670

Gly Arg Ile Asp Ile Met Gly Thr Ile Val Tyr Asp Ser Ala Pro Tyr
        675                 680                 685

Leu Tyr Pro Phe Ile Ile Glu Tyr Ser Leu Ile Gly Ala Val Val Leu
        690                 695                 700

Tyr Val Met Trp Lys His Ile Gly Arg Tyr Pro Gly Arg Met Asn Asp
705                 710                 715                 720

Glu Asp Leu Glu His Arg Leu Glu Val Met Leu Ser Arg Arg Ala Val
            725                 730                 735

Ala Met Ala Gln Gln Ala Arg Ser Gly Arg Val Asp Cys Val Gly Ser
        740                 745                 750

Ser Lys Gly Leu Phe Phe Gly Leu Leu Leu Val Gly Ala Leu Ile
        755                 760                 765

Cys Leu Ile Leu Phe Phe Val Leu Val Arg His Gln Gln Phe Ser Leu
770                 775                 780

Leu Ala Ile Tyr Leu Ala Asp Ala Ser His Cys Ile Leu Met Ala Phe
785                 790                 795                 800

Ala Ile Leu Ala Ile Ile Val Gly Phe Ile Arg Val Lys Asn Leu Lys
            805                 810                 815

Phe Arg Cys Glu Glu Gln Ser Asn Leu Asn Asp Ile Leu Leu Arg Ile
        820                 825                 830

Ser Ala Phe Gly Leu Phe Thr Tyr Ser Val Phe Ser Ile Ile Ala Gly
        835                 840                 845

Ser Leu Lys Val Leu Glu Ser Glu Pro Ser Leu Leu Val Thr Thr Thr
850                 855                 860

Gly Gly Val Ala Val Phe Gln Val Ile Leu Gln Leu Leu Phe Ile Ala
865                 870                 875                 880

Asp Val Ser Arg Arg Val His Leu Pro Glu His Asp Arg Ser Lys
            885                 890                 895

Pro Gly Arg Gln Ile Val Thr Phe Leu Leu Ile Cys Asn Val Ala Met
        900                 905                 910

Phe Ala Ile Tyr Thr Phe Glu Ala Gln Lys Val Phe Ala Asn Pro Val
    915                 920                 925

Ser Arg Tyr Val Gln Leu Glu Phe Tyr Gly Phe Val Pro Trp Ser Ile
        930                 935                 940

Ile Gln Arg Ile Thr Leu Pro Leu Cys Ile Phe His Arg Phe His Ser
945                 950                 955                 960

Ala Val Thr Leu Ala Glu Ile Trp Lys Thr Thr Tyr Lys Ala Arg Leu
            965                 970                 975

Glu

<210> SEQ ID NO 8
<211> LENGTH: 797
<212> TYPE: PRT
<213> ORGANISM: Drosophila

<400> SEQUENCE: 8

Met Ser Leu Ile Asn Leu Lys Ser Lys Asp Met Tyr Asp Glu Pro Ile
1               5                   10                  15

Asn Leu Trp Arg Thr Lys Gln Arg Val His Tyr His His Asp Val Ile
            20                  25                  30
```

-continued

```
Ser Lys Gly Asn Asp Ser His Arg Ser Ser Asp Ala Cys Glu Tyr Ile
         35                  40                  45

Thr Ile Ser Ala Pro Lys Lys Ser Gly Ser Phe Ser Arg Ser Pro Pro
 50                  55                  60

Ser Ser Leu Pro Thr Ser Val Pro Gly Thr Pro Arg His Ser Val Ala
 65                  70                  75                  80

Ala Thr Ser Asn Gln Val Ile Arg Tyr Ala Arg Thr Ser Cys Asp His
                 85                  90                  95

Cys Gly His His Ser Ile Pro Val Met Ser Pro His Pro Ile Ser Pro
            100                 105                 110

Leu Ala Lys Ser Gln Thr Asn Leu Asp Leu Val Glu His Gly Ser Gln
        115                 120                 125

Arg Gln Ala Leu Leu Pro Leu Pro Thr Val Gly Met His His Glu Asp
130                 135                 140

Ser Ala Cys Thr Leu Gln Val Ser Arg Arg Pro Ser Leu Leu Leu Gln
145                 150                 155                 160

Glu Ile Leu Thr Gln Arg Pro Pro Leu Phe Gly Arg Arg Asp Gly Asn
                165                 170                 175

Gly Phe Leu Ser Pro Arg Thr Ala Lys Asn Gly Asn Leu Gln Gly Thr
            180                 185                 190

Ala Ser Gly Ser Thr Ala Thr Ile Asn Phe Gln Ser Gly Ala Thr Ser
        195                 200                 205

Ala Arg Asn Gly Ser Thr Ala Phe Phe Asp Asn Gly Ala Lys Ser Phe
210                 215                 220

Gln Ala Lys Gln Gln Lys Asp Lys Asn Arg Arg Thr Gly Asn Asp Ala
225                 230                 235                 240

Ile Ser Ser Ala Leu Ser Ala Thr Tyr Cys Lys Leu Leu Val Leu Leu
                245                 250                 255

Gly Val Cys Leu Pro Ile Thr Glu Val Ile Ser Asp Gln Ile Pro Thr
            260                 265                 270

Tyr Val Tyr Gln Gly Phe Tyr Val Tyr Leu Tyr Val Gly Ser Ile Leu
        275                 280                 285

Phe Val Ile Phe Leu Tyr Ile Ser Ala Phe Arg Asn Arg Ser Leu Phe
290                 295                 300

Asn Ala Leu Lys Asp Tyr His Glu Lys Asn Ser Asn Val His Leu Lys
305                 310                 315                 320

His Lys Val Thr His Phe Gly Ser Phe Tyr Leu Arg Val Gly Ala Ile
                325                 330                 335

Ala Phe Ala Ile Gly Thr Met Val Tyr Ser Gly Leu Glu Phe Gly Gln
            340                 345                 350

Phe Phe Glu Leu Asn Gly His Pro Gly Cys Arg Asp Val Phe Val Ala
        355                 360                 365

Ile Thr Pro Ile Cys Arg Met Val Leu Cys Ile Ala Gln Val Gln Phe
370                 375                 380

Ile Phe Leu Asn Thr Thr Tyr Met Asp Met Ala Arg His Lys Val Thr
385                 390                 395                 400

Ser Arg Phe Gly Leu Met His Met Val Ala Thr Asn Leu Cys Glu Trp
                405                 410                 415

Leu Tyr Val Leu Val Glu Glu Thr Lys His Glu Ile Phe His Ile Ser
            420                 425                 430

Gln His Glu Val Asp Pro Ala His Asp Leu Val Ile His Asn Ser Ser
        435                 440                 445

Met Ser Arg Thr Asp Trp Ala Ala Val Asn Glu Ser Leu His Gln His
```

```
                450             455             460
His His His His Ala Leu Asn Asn Thr Leu Val Ala Asn Val Ser Ser
465                 470                 475                 480

Val Ile Val Asn Met Thr Ile Thr Pro Ser Pro Thr Pro Ala Ala Phe
                485                 490                 495

Ser Gly Cys Ser Arg Thr Thr Ile Met Gly Ala Leu Val Gln Gln Leu
            500                 505                 510

Ser Pro Phe Leu Phe Pro Cys Thr Ile Glu Tyr Ser Leu Ile Cys Ala
        515                 520                 525

Val Ile Leu Phe Glu Met Trp Lys Thr Val Lys Ser Ile Pro Asp Ile
530                 535                 540

Asp Lys Thr Arg Lys Asn Ser Val Lys Pro Ala Ala Lys Pro Ala
545                 550                 555                 560

His His Phe Ser Val Asp Cys Ser Gln Ser His Lys Gly Leu Phe Phe
                565                 570                 575

Gly Ile Leu Ile Ile Val Met Thr Ile Ile Ser Met Ile Met Tyr Phe
            580                 585                 590

Val Leu Tyr Thr Gln Pro Gly Tyr Glu Leu Val Ala Thr Gln Glu Val
        595                 600                 605

Thr Leu Trp Glu Thr Phe Met Tyr Phe Met Cys Ala Ala Ala Val Ile
610                 615                 620

Thr Gly Met Ile Leu Met Arg Asp Leu Arg Tyr Ile Lys Asn Thr Ser
625                 630                 635                 640

Asp Glu His His Ser Met Asp Leu Asp Asn Leu Leu Leu Ile Val Ala
                645                 650                 655

Gln Thr Gly Val Tyr Leu Tyr Gly Met Phe Ser Ile Leu Gly Ser Tyr
            660                 665                 670

Phe Ala Lys Trp Asp Thr Val Pro Asp Arg Val Glu Gly Ile Ile Ala
        675                 680                 685

Glu Val Phe Gly Val Val Gln Thr Ser Leu Gln Thr Met Phe Ile Leu
690                 695                 700

His Ser Ser His Arg Arg Cys Arg Gly Thr Asn Gln Val Arg Arg Lys
705                 710                 715                 720

Pro Gly Arg Glu Ile Ile Thr Phe Leu Leu Val Ala Asn Ile Ala Ile
                725                 730                 735

Trp Phe Val Asn Thr Leu Ile Lys Gly Arg Ala Val Phe Arg Glu Ser
            740                 745                 750

His Leu Glu Phe Phe Gly Val Trp Gly Trp Thr Ile Ile Thr His Ile
        755                 760                 765

Ser Met Pro Leu Ala Ile Phe Tyr Arg Phe His Ser Thr Ile Cys Leu
770                 775                 780

Phe Glu Val Trp Lys Ile Thr Tyr Lys Ala Lys Ala His
785                 790                 795

<210> SEQ ID NO 9
<211> LENGTH: 1576
<212> TYPE: PRT
<213> ORGANISM: Drosophila
<220> FEATURE:
<221> NAME/KEY: misc_feature
<222> LOCATION: (1456)..(1456)
<223> OTHER INFORMATION: Xaa can be any naturally occurring amino acid

<400> SEQUENCE: 9

Met Asp Ser Ser Pro Asp Leu Ser Leu Lys Leu Arg Arg Gly Ser Ser
1               5                   10                  15
```

-continued

```
Asp Ser Arg Asp Asn Phe Tyr Met Asp Phe Ala Gln Gly Ile Asp Ser
                20                  25                  30

Asp Ile Glu Glu Val Asp Asn Thr Ala Asn Asn Gln Glu Ala Gly Glu
            35                  40                  45

Val Pro Pro Pro Leu Pro Thr Val Ser Leu Ala Glu Glu Val Leu
 50                  55                  60

Leu Leu Val Ala Pro Pro Pro Pro Ser Leu Leu Gly Gln Pro
 65                  70                  75                  80

Leu Pro Thr Leu Thr Glu Thr Asp Asp Ile Pro Thr Pro Thr Pro
                85                  90                  95

Pro Pro Gln Gln Lys Asp Asp Glu Gly Asp Glu Asp Glu Arg Glu
            100                 105                 110

Glu Pro Val Pro Glu Gln Asp Gln Gly Ala Pro Ala Ala Pro Ser Pro
            115                 120                 125

Pro Gly Ser Pro Ile Asn Ser Val Leu Glu Leu Glu Leu Ile Pro Pro
 130                 135                 140

Pro Pro Leu Ser Pro Met Asp Asp Ala Gly Leu Arg Thr Asp Asp Asp
 145                 150                 155                 160

Gly Glu Gly Glu Glu Thr Asp Asp Ala Glu Glu Val Ala Ala Ile Pro
                165                 170                 175

Pro Pro His Glu Met Leu Asp Ile Glu Ser Asn Pro Asp Glu Glu
            180                 185                 190

Glu Glu Glu Glu Gln Glu Gln Ala Ser Gln Glu Asp Thr Pro Lys Glu
            195                 200                 205

Glu Asp Glu Glu Glu Asp Asp Asp Lys Ser Thr Pro Pro Pro Leu
 210                 215                 220

Pro Pro Leu Pro Ser Asn Phe Ser Tyr Val Gln Gly His Asn Leu Gly
 225                 230                 235                 240

Gln Val Thr Pro Pro Leu Thr Lys Ser Pro Ser Asn Ser Pro Ser Pro
            245                 250                 255

Pro Val Thr Pro Pro Cys Pro Glu Leu Asn Ile Ser Arg Met Val
            260                 265                 270

Ser Pro Pro Ala Gln His Ile Ser Gln Ile Pro Pro Leu Thr Pro Ser
            275                 280                 285

Asp Glu Ser Glu Gly Glu Ala Glu Ser Gln Pro Asn Ser Pro Pro Leu
 290                 295                 300

Arg Leu Asp Ala Glu Gln Pro Pro Asp Met Asp Gln Pro Glu Pro
 305                 310                 315                 320

Glu Asp Gln Pro Pro Glu Pro Glu Asn Glu Pro Glu Pro Glu Pro Glu
            325                 330                 335

Pro Glu Pro Glu Pro Glu Pro Val Ser Gly Ala Arg Gly Asp Tyr Ser
            340                 345                 350

Arg Ser Leu Asp Asn Glu Asp Glu Ser Thr Thr Ile Thr Thr Pro Pro
            355                 360                 365

Ser Asn Gly Tyr Ser Ala Ser Ser Ile Ile Ala Pro Pro Glu His
            370                 375                 380

Phe Ala Glu Leu Asp Glu Asp Arg Gly Phe Ile Pro Pro Pro Leu
 385                 390                 395                 400

Glu Gln Glu Pro Glu Glu Glu Val Glu Glu Glu Glu Glu Glu Glu
                405                 410                 415

Glu Glu Leu Thr Lys Glu Thr Asp Glu Ile Ser Val Asp Arg Glu Ser
            420                 425                 430
```

-continued

```
Leu Gln Asp Gln Gly Gly Asp Ser Ile Ser Ser Pro Arg Pro Ala Ser
        435                 440                 445
Ile Leu Thr Gly Ser Ile Ser Thr Ser Val Gly Gly Ala Gly Gly
    450                 455                 460
Ser Pro Lys Pro Glu Ser Arg Gly Pro Ser Arg Ser Gly Ser Gln Arg
465                 470                 475                 480
Ser Gln Leu Arg Ser Gly Ser Gln Gly Ser Ile Ala Glu Ser Arg
            485                 490                 495
Gly Gly Ser Arg Ile Gly Ser Arg Thr Gly Ser Val Ala Ser Ala Gln
            500                 505                 510
Ala Ala Gly Val Leu Ser Pro Gln Ala Ser Leu Lys Ser Gln Thr Ser
        515                 520                 525
Ile Arg Ser Gln Gly Gln Ala Gly Val Arg Ser Pro Ala Gly Ser Ile
    530                 535                 540
Lys Ser Gly Ser Gln Arg Met Gln Ser Pro Gln Ala Gly Glu Gly Ala
545                 550                 555                 560
Pro Ala Met Pro Ser Pro Pro Leu Met Arg Ser Pro Pro Glu Leu
            565                 570                 575
Ala Arg Gln Met His Ser Pro Arg Ile Thr Thr Pro Pro Arg Val
        580                 585                 590
Cys Ser Pro Pro Leu Val Ser Ser Pro Pro Lys Leu Ala Glu Ser Ala
    595                 600                 605
Ala Ala Ala Val Gly Val Ala Ala Thr Val Lys Glu Gln Ile Gly Ser
        610                 615                 620
Ser Ser Ser Thr Ala Glu Pro Leu Glu Pro Ser Lys Pro Glu Pro Leu
625                 630                 635                 640
Lys Pro Pro Ile Ala Thr Val Ser Tyr Gln Asp Glu Gln Lys Pro Ser
            645                 650                 655
Pro Pro Pro Thr Ala Ala Ala Pro Ala Val Thr Thr Ala Ala
            660                 665                 670
Thr Thr Ala Val Thr Ser Gln Pro Arg Ser His Phe Thr Ser Ser His
        675                 680                 685
His His Tyr His Leu Pro His Gln Phe Gln His Pro His His Gln Asn
    690                 695                 700
His His Thr His Ser Val Arg Val Pro Thr Pro Thr Val Pro Ser Ser
705                 710                 715                 720
Tyr Ala Pro Pro Pro Pro Asp Ser Gly Ser Ser Ser Pro Val
            725                 730                 735
Asp Arg Arg Arg Leu Phe Met Ala Gly Val Ala Pro Ile Ala Ala
        740                 745                 750
Gly Ala Gly Ser Leu Met Ala Met Pro Ala Glu Pro Ala Val Ala Ile
    755                 760                 765
Ser Pro Gly Arg Val Ser Ala Arg Ser Gly Ser Gln His His Val Thr
770                 775                 780
Ile Asp Glu Ser Ser Leu Pro Ser His Lys Gly Asn Ile Gln Glu Thr
785                 790                 795                 800
Pro Gly Pro Ser Gly Leu Ile Ile Gly Gly Gly Asp Gly Asp Gly Asp
            805                 810                 815
Arg Asp Ile Gly Gly Gly Gly Pro Asp Ser Ser Asp Pro Ser
        820                 825                 830
Ser Pro Gly Gly Ser Ser Gln Pro Ala Leu Ser Gly Ser Gln Ala
        835                 840                 845
Asp Gly Gln Leu Ala Leu Met Tyr His Ser His Gln Leu Thr Asn Tyr
```

-continued

```
            850                 855                 860
Pro Val Leu Pro Ala Ile Lys Arg Thr His Arg Pro Ser Phe Val Tyr
865                 870                 875                 880

Pro Pro Met Pro Arg Val Lys Ala Gly Asp Ala Leu Ala Thr Leu Phe
                885                 890                 895

Ser Ala Leu Tyr Gly Lys Leu Leu Val Val Met Gly Ile Ala Phe Pro
                900                 905                 910

Met Ala Glu Val Ile Ser Thr Tyr Ile Pro Pro Ser Phe Tyr Glu Val
            915                 920                 925

Tyr Tyr Leu Tyr Leu Tyr Ile Gly Ser Met Ile Phe Leu Leu Phe Met
        930                 935                 940

Tyr Ala Thr Leu Ile Trp Gly Arg Pro Lys Leu Pro Val Pro Ile Ala
945                 950                 955                 960

Ser Pro Ser Lys Ser Ala Thr Lys Ala Ser Gly Thr Asp Ser Met Asp
                965                 970                 975

Glu Ser Asp Thr Asp Ser Asn Ser Val His His Arg Leu Pro Pro Pro
                980                 985                 990

Ile Pro Val Arg Arg Pro Ser Leu  Leu Ser Pro Leu Gly  Arg Arg Asp
            995                 1000                1005

Ala His  Tyr Gly Ser Phe Tyr  Leu Arg Met Gly Ala  Val Ala Phe
    1010                1015                1020

Gly Ile  Gly Ser Met Ile Tyr  Ser Gly Leu Glu Phe  Gly Gln Tyr
    1025                1030                1035

Phe Glu  Leu Asn Pro Asp Thr  Lys Cys His Asn Val  Leu Leu Ala
    1040                1045                1050

Leu Thr  Pro Ala Thr Arg Met  Ala Phe Ile Phe Ile  Gln Met Tyr
    1055                1060                1065

Phe Ile  Phe Leu Asn Asn Glu  Gln Ile Lys Val Tyr  Arg Tyr Lys
    1070                1075                1080

Ile Ile  Ala Arg Phe Gly Leu  Met His Met Ile Gly  Thr Asn Leu
    1085                1090                1095

Ala Val  Trp Leu Asn Val Leu  Ile Gln Glu Thr Lys  His Glu Ile
    1100                1105                1110

Leu Thr  Phe Tyr Asn Pro Glu  Asn Arg Thr Leu Arg  Ile Ser His
    1115                1120                1125

Arg Ile  Pro Gly His Ser Arg  Gly His Ala Ile Ile  Gln His Asp
    1130                1135                1140

Pro Thr  Ala His Leu Arg Val  Pro Arg Gly Leu Lys  Gly Pro Tyr
    1145                1150                1155

Gln Ile  Phe Glu Cys Arg Arg  Thr Asn Ile Ile Gly  Thr Leu Val
    1160                1165                1170

Gln Asp  Ala Ser Pro Phe Leu  Phe Pro Cys Thr Ile  Glu Tyr Ser
    1175                1180                1185

Leu Ile  Cys Ala Ala Ile Leu  Tyr Val Met Trp Arg  Ser Ile Ser
    1190                1195                1200

Arg Pro  Gln Thr Pro Thr Pro  Gln Arg Pro Asp Met  Ile Ser Ser
    1205                1210                1215

Pro Met  Lys Arg Ser Pro His  His Tyr Ser Val Asp  Cys Ala Arg
    1220                1225                1230

Ala His  Lys Gly Leu Phe Val  Gly Ile Leu Ile Leu  Val Leu Thr
    1235                1240                1245

Ile Ile  Ser Leu Ile Ile Phe  Phe Val Leu Ile Ser  Arg Pro Glu
    1250                1255                1260
```

-continued

```
Phe Val Ala Met Ala Val Thr Glu Val Thr Ile Cys Glu Leu Leu
1265                1270                1275

Ile Tyr Gly Thr Ala Thr Ile Ala Thr Leu Val Gly Met Ile Gln
1280                1285                1290

Ile Arg His Leu Gln Tyr Asp Ala Tyr Arg Ser Phe Ser Leu Asp
1295                1300                1305

Asp Ile Leu Leu Val Gly Ala Gln Thr Gly Ser Phe Leu Tyr Asn
1310                1315                1320

Ile Phe Thr Val Ile Ala Gly His Phe Thr Leu Arg Ser Asp Asp
1325                1330                1335

Met Leu Val Pro Ile Asn Ala Leu Ala Ser Ile Val Gln Thr Ala
1340                1345                1350

Cys Gln Thr Met Phe Ile Leu Asp Ala Ser Arg Arg Gln Ala Val
1355                1360                1365

Ser Pro Glu His Leu Arg Lys Lys Pro Gly Arg Glu Ile Val Thr
1370                1375                1380

Phe Met Leu Val Val Asn Leu Ala Met Trp Ala Ile Ser Thr Leu
1385                1390                1395

Glu Lys Ser Arg Ala Glu Ser His Pro Ile Gln Leu Asn Phe Tyr
1400                1405                1410

Gly Leu Trp Ala Trp Thr Ile Ile Thr His Val Ser Met Pro Leu
1415                1420                1425

Ala Ile Phe Tyr Arg Phe His Ser Thr Val Cys Leu Cys Glu Ile
1430                1435                1440

Trp Lys Arg Ala Tyr Lys Leu Lys Pro Thr Tyr Met Xaa Glu Phe
1445                1450                1455

Ala Arg Ser Arg Ile Gln Ser Ile Ala Gln Gln Gln Phe Cys
1460                1465                1470

Glu Asp Leu Lys Thr Asn Leu Ser Tyr Cys Tyr Cys Ser Thr Thr
1475                1480                1485

Leu Ala Gly Gly Glu Leu Glu Thr Val Glu Glu Val Asp Ser Gly
1490                1495                1500

Glu Ser Asn Ser Ala Glu Asp Ala Gly Ala Gly Ala Gly Ser Gly
1505                1510                1515

Gly Ser Arg Gly Ser Gly Gly Ala Gly Ala Ala Glu Ala Gly
1520                1525                1530

Glu Ala Gly Glu Glu Gly Gln Gln Gly Gly Asp Ser Ser Cys Gly
1535                1540                1545

Leu Lys Ala Pro Ile Arg Ala Leu Ser Pro Gln Ser Leu Asn Thr
1550                1555                1560

Glu Lys Ala Phe Cys Pro Val Tyr Val Ile Asn Gly Glu
1565                1570                1575
```

METHODS OF IDENTIFYING A MOLDULATOR OF OTOPETRIN-MEDIATED PROTON TRANSLOCATION ACTIVITY

RELATED PATENT APPLICATION

This application is the United States National Stage of International Application No. PCT/US2018/044058, filed Jul. 27, 2018, which claims the benefit of priority of U.S. Provisional Patent Application Ser. No. 62/537,900, filed on Jul. 27, 2017, the contents of which are hereby incorporated by reference in their entireties.

GOVERNMENT SUPPORT

This invention was made, in part, with government support under National Institutes of Health grants R01DC013741 and R21DC012747. The government has certain rights in the invention.

SEQUENCE LISTING

Pursuant to 37 C.F.R 1.821(c), a sequence listing is submitted herewith as an ASCII compliant text file named "USC0509153_ST25.txt", created Jan. 27, 2020, and having a size of 58.3 kilobytes. The content of the aforementioned file is hereby incorporated by reference in its entirety.

FIELD OF THE INVENTION

Embodiments of the invention relate to compositions and methods for identifying modulators of otopetrin-mediated proton translocation.

INTRODUCTION

Lipid bilayers are impermeable to protons, whose movement into and out of cells is tightly regulated by membrane proteins, including ion channels. As presented herein, the transmembrane protein Otopetrin 1 (Otop1) and certain related transmembrane proteins are identified as proton-selective ion channels.

BRIEF DESCRIPTION OF THE FIGURES

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A shows current measured by TEVC in a *Xenopus* oocyte expressing Otop1 in response to Na$^+$-free extracellular solutions of decreasing pH ($V_m$=−80 mV). FIG. 1B shows the I-V relation of the current in FIG. 1A. The voltage was ramped from −80 mV to 80 mV at 1V/s. FIG. 1C shows the average magnitude (mean±SEM) of the evoked currents (ΔI) as a function of pH in *Xenopus* oocytes injected with Otop1 mRNA (n=4) and un-injected oocytes (grey circles; n=4). FIG. 1D shows the current measured by whole-cell patch clamp recording in a HEK-293 cell transfected with Otop1 in Na$^+$-free solution ($V_m$=−80 mV). FIG. 1E shows the I-V relation of the current evoked in an Otop1-transfected HEK-293 cells with pH. as indicated from experiments in which the voltage was ramped (1V/s). FIG. 1F shows the average magnitude (mean±SEM) of the evoked currents (ΔI) as a function of pH in HEK-293 cells transfected with Otop1 (squares; n=5) and untransfected cells (grey squares; n=3). FIG. 1G shows a fusion protein of Otop1 with YFP (YFP-Otop1) co-transfected with the cytosolic protein tag-RFP and imaged with confocal microscopy. Line scan (FIG. 1G, bottom panel) shows that YFP-Otop1 is enriched on the cell surface. FIG. 1H shows Otop1-transfected, but not sham-transfected cells, responded to a change in extracellular pH with a large change in intracellular pH, as measured with pHrodo red (mean±SEM. n=9-11). Similar results were obtained in 3 replicates. Average data (mean±SEM; n=28-29 cells) was analyzed by 2-tailed t-test. ****: p<0.0001. HOAc served as a positive control.

FIGS. 2A-2G—Ion selectivity and biophysical properties of Otop1. FIG. 2A shows that Otop1 currents evoked in response to a low pH solution with Na$^+$, Li$^+$ or Cs$^+$ (160 mM each) or Ca$^{2+}$ (40 mM) replacing NMDG$^+$ in the extracellular solution at the time indicated ($V_m$=−80 mV). Average percentage change in the current is indicated. FIG. 2B shows Otop1 currents evoked in response to voltage ramps (1 V/s) at varying extracellular pH under conditions that minimized ion accumulation and allow isolation of the Otop1 current (pH$_i$=6.0; Zn$^{2+}$-sensitive component is shown). FIG. 2C shows $E_{rev}$ as a function of ΔpH ($p_H$-pH$_o$) from experiments as in FIG. 2b. The line shows the prediction for a purely H$^+$-selective conductance. The data were fit by linear regression with a slope of 53 mV/ΔpH and a Y intercept of 3.6 mV ($R^2$=0.99). FIG. 2d and FIG. 2E show Otop1 current (Zn$^{2+}$-sensitive component) measured in the presence of 140 mM NMDG$^+$, 4 mM Cl$^-$ ($E_{rev}$=34.4±1.0, n=5); 140 mM Na$^+$, 4 mM Cl$^-$ ($E_{rev}$=34.4±1.0, n=5); 140 mM Na$^+$, 20 mM Cl$^-$ ($E_{rev}$=33.8±1.0, n=5); or (d) 140 mM NMDG$^{30}$, 4 mM Cl$^-$ (35.2±1.2, n=5); NMDG$^+$, 20 mM Cl$^-$ (35.5±0.5, n=4). There was no significant difference between any of the conditions, p>0.05 by ANOVA. FIG. 2F shows Otop1 currents in HEK-293 cells are blocked in a dose-dependent manner by Zn$^{2+}$ (pink bar, concentrations indicated are in mM). FIG. 2G shows average data (mean±SEM; n=6-14) was fit with a Hill equation with an IC$_{50}$ of 0.19 mM and a Hill coefficient of 0.89.

FIG. 3A shows the maximum-likelihood phylogenetic tree created from the multi-sequence alignment of 13 otopetrin family proteins. Scale bar is 0.1 subs/site. FIG. 3B shows the sequence Identity in the transmembrane, cytoplasmic and extracellular domains between the 3 mouse homologs (Otop1, Otop2, and Otop3; left) and between mOtop1 and dmOTOPLc (right). TM domain 11 is highly conserved among the mammalian proteins, while TM domain 5 is most highly conserved between vertebrate and invertebrate proteins. TM domain 12 is highly conserved among all. FIG. 3C and FIG. 3E show currents evoked in *Xenopus* oocytes expressing Otop2, Otop3 (FIG. 3C) or dmOTOPLc (FIG. 3E) in response to varying pH$_o$. Representative traces (Vm=−80 mV) and I-V relationship (from voltage ramps at 1 V/s) are shown. As expected for a proton-selective ion channel, $E_{rev}$ shifted to the right as pH$_o$ was lowered for Otop3 and dmOTOPLc. Otop2 showed anomalous behavior. FIG. 3D (top panel, mOtop2; bottom panel, mOtop3)and FIG. 3f show the average current induced (ΔI) as a function of pH for each of the channels (black circle; mean±SEM, n=3-7). Grey triangles show response from un-injected oocytes (n=3, mean±SEM). Note that the relationship between ΔI and pH varied between channels, with mOtop3 showing the steepest relationship.

FIG. 4A shows the voltage and solution exchange protocol designed to stabilize Otop1 currents and reduce changes in $[H^+]_i$. Intracellular solution was adjusted to $pH_i=6.0$ and $V_m$ was held close to $E_H$ (−60 mV for $pH_o=7.0$ and +30 mV for $pH_o=5.5$) and the voltage was ramped 1 V/s from −80 mV to +80 mV. Response of a HEK-293 cell transfected with Otop1 and an untransfected cell to a pH 5.5 solution (NMDG-based) is shown (capacitance artifacts were removed). Note that the current evoked in response to pH 5.5 in the Otop1-expressing cell remained stable throughout the duration of the recording. FIG. 4B shows the I-V curves obtained from experiments as in a. The current elicited in response to pH 5.5 following exposure to $Zn^{2+}$ was subtracted from the current prior to $Zn^{2+}$ exposure to derive a pure Otop1-dependent current (3-4), from which $E_{rev}$ was measured.

FIG. 5 shows Otop1 currents in *Xenopus* oocytes in response to a family of voltage steps (shown) before and during exposure to pH 5.5 solution. Right, Average data (n=4) measured at the times indicated. Only for the most hyperpolarizing voltage step to −80 mV was there any time-dependent change in the current amplitude.

FIGS. 6A and 6B show $E_{rev}$ as a function of pH for Otop2 and Otop3 expressed in *Xenopus* oocytes. Gray line shows a linear fit of the data between pH 5 and 6 with a slope of 20.7 and 46.3 mV/log[$H^+$] for Otop2 and Otop3, respectively. Dotted line shows $E_H$, assuming $pH_i$ is 7.2. FIG. 6B shows response of Otop2(top panel), and Otop3 (bottom panel) to hyperpolarizing voltage steps at neutral and acidic pH in *Xenopus* oocytes shows minimal to mild voltage-dependent gating. Data are representative of n>3 experiments. Note that we consistently observed an outward current in Otop2-expressing oocytes at 0 mV in pH 7.4 solution. This may be due to the outward movement of protons through the channel. FIG. 6C shows the change in intracellular pH of HEK-293 cells transfected with Otop2 (top panel) or Otop3 (bottom panel) or sham transfected, in response to pH 5 solution without and with acetic acid monitored with the pH indicator pHrodo red (mean±SEM). FIG. 6D shows the average data (mean±SEM) from experiments as in c, measured at the peak of the response). Significance determined by 2-tailed t-test. ***: P<0.001. Similar results obtained in 3 replicate experiments.

FIG. 7A shows Otop2 currents measured with whole-cell patch clamp recording of transfected HEK-293 cells. The solution was exchanged and the membrane voltage was ramped, as indicated, from −80 mV to +160 mV (1V/s). FIG. 7B shows I-V relations from the experiment shown in (a). FIG. 7C shows the average (mean±SEM) of $E_{rev}$ from experiment as in FIGS. 7A and 7B. A linear fit of the data between pH 5 and 6 with a slope of 25.3 mV/log [$H^+$] is shown. A corresponding relationship for Otop2 in *Xenopus* oocytes is also shown.

FIGS. 8A-8D shows further evidence that Otop1 forms a proton channel. FIG. 8A shows currents elicited in hOtop1 transfected HEK293 cells in response to varying external pH. FIG. 8B shows the average magnitude of the current from experiments as in FIG. 8A at pH 5.0 in transfected and untransfected cells. FIGS. 8C and 8D show changes in intracellular pH of HEK 293 cells transfected with hOtop2 or sham transfected, as measured with the pH indicator pHrodo red (mean+/−SEM), in response to a pH 5 solution with, and without acetic acid. Error bars represent SEM. Significance is calculated by ANOVA. ****: P<0.0001; Similar results obtained in at least 3 replicate experiments.

FIG. 9 shows intracellular calcium changes in HEK-293 cells transfected with mOtop1 or sham-transfected. Transfected cells were loaded with the calcium indicator Fura2 AM and exposed to a change in extracellular pH from 7.4 to 5.0. FIG. 9 (left panel) shows that only the Otop1 transfected cells responded (n=8 cells). Both cell types responded to HOAc, pH 5, which penetrates cell membranes and causes intracellular acidification, thereby elevating intracellular calcium by liberating it from intracellular buffers. The peak magnitude of the response is shown in the right panel. The difference between Otop1 transfected and sham-transfected cells is significant (student's t-test. *** p<0.001).

FIGS. 10A-10D show that HEK-293 cells transfected with Otop1 (FIG. 10A), Otop2 (FIG. 10B), and Otop3 (FIG. 10C) demonstrate a decrease in intracellular pHluorin fluorescence (which indicated that the intracellular pH was lowered), in response to applying an acidic pH solution to the cells (adjusted by HCl). A decrease in intracellular pH was not observed in the control (FIG. 10D), which was transfected with pHluorin only. However, when applying a basic solution (pH 8.5), only cells with Otop1 and Otop2 showed an increase in pHluorin fluorescence (intracellular alkalization), not Otop3. Applying the acetic acid solution at pH 5.0 (weak acid) induced intracellular acidification, which served as a control to show that pHluorin fluorescence decreased in all cells following the lowering of intracellular pH. Black line: average pHluorin fluorescence intensity. Light gray line: s.e.m. of pHluorin fluorescence intensity. Dark gray bar: different pH solutions applied (blank: pH 7.4). HOAc: Acetic acid.

SUMMARY OF THE INVENTION

Figure 1A:
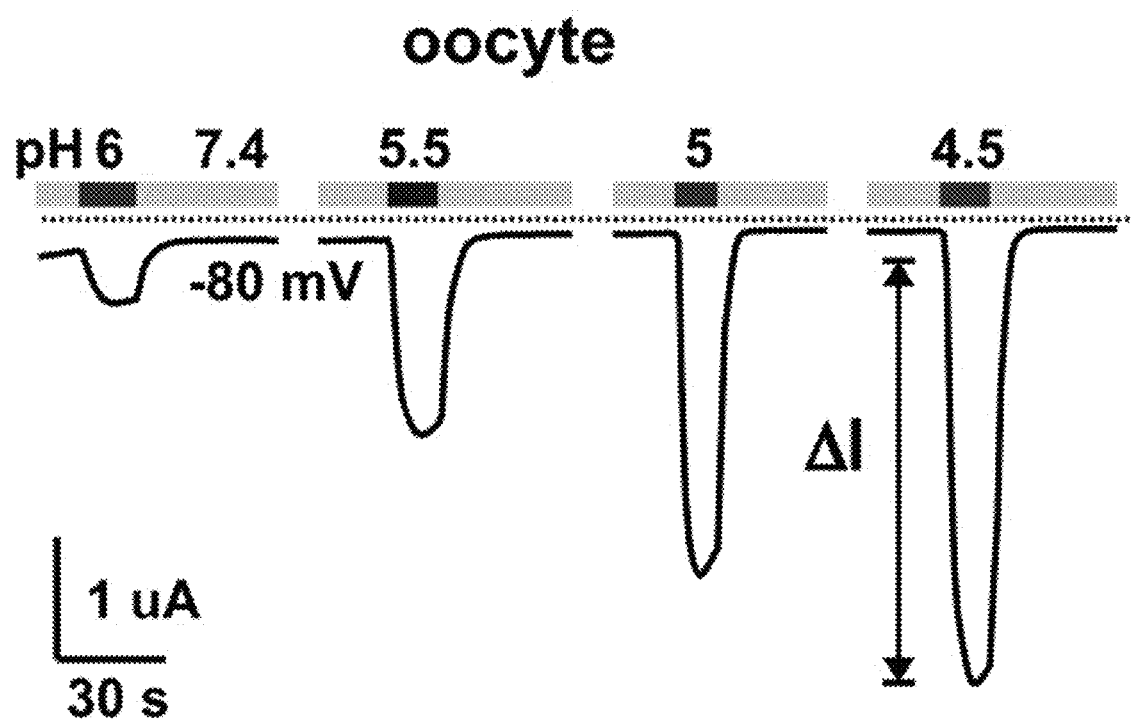
FIGS. 1A-1H—Otop1 generates an acid-induced current in *Xenopus* oocytes and HEK-293 cells.

In some aspects, presented herein is a method of identifying a modulator of otopetrin-mediated proton translocation activity comprising (a) contacting an otopetrin polypeptide, or functional portion thereof, with a test compound and (b) determining a proton translocation activity mediated by the otopetrin polypeptide, or the functional portion thereof, wherein an increase or decrease of at least 1% of the proton translocation activity, compared to a proton translocation activity determined in an absence of the test compound, identifies the test compound as a modulator of proton translocation activity mediated by the otopetrin polypeptide, or the functional portion thereof. In some embodiments, a proton translocation activity mediated by an otopetrin polypeptide is determined in response to a change in pH. A change in pH can be an increase or decrease in pH. In some embodiments a change in pH is a change of at least 0.1 pH units. In some embodiments, a proton translocation activity mediated by an otopetrin polypeptide is determined in response to a change in extracellular pH. In some embodiments, the method comprises inducing a change in pH (e.g., extracellular pH). In some embodiments, an otopetrin polypeptide is integrated into a lipid bilayer and the method comprises, prior to (a) or prior to (b), inducing a change in pH by adding an acid or base to one side (e.g., an extracellular side) of the otopetrin polypeptide.

In some aspects, presented herein is a method of identifying a modulator of otopetrin-mediated proton translocation activity comprising (a) measuring a proton translocation activity mediated by an otopetrin polypeptide, or a functional portion thereof, (i) in the presence of a test compound, and (ii) in the absence of the test compound; and (b) determining a difference between the proton translocation activity measured in (a)(i) compared to the proton translocation activity measured in (a)(ii), thereby identifying the test compound as a modulator of the proton translocation activity mediated by the otopetrin polypeptide, or the functional portion thereof.

In some aspects, presented herein is a cell comprising an extracellular membrane and an otopetrin polypeptide (e.g., a heterologous otopetrin polypeptide) integrated in the extracellular membrane of the cell. In some embodiments, the cell is a *Xenopus* oocyte. In some embodiments, the cell is a mammalian cell. In some embodiments, the cell is a taste receptor cell. In certain embodiments, the otopetrin polypeptide is a heterologous otopetrin polypeptide (e.g., heterologous to a cell that comprises the otopetrin polypeptide). For example, in some embodiments, an otopetrin polypeptide is a human otopetrin polypeptide that is expressed in a heterologous insect, reptilian or non-human mammalian cell. In some embodiments, an otopetrin polypeptide is a human otopetrin polypeptide expressed in an immortalized cell or cell-type that does not naturally express an otopetrin polypeptide.

In some embodiments, the methods described herein comprise introducing a nucleic acid into a mammalian cell or oocyte wherein the nucleic acid directs the expression of an otopetrin polypeptide. In some embodiments, a nucleic acid that directs the expression of an otopetrin polypeptide is a cDNA that encodes an otopetrin polypeptide. For example, in certain embodiments, a mammalian cell or oocyte is transfected with a cDNA encoding an otopetrin polypeptide. Any suitable nucleic acid or cDNA that encodes an otopetrin polypeptide, or functional portion thereof, can be used for a method described herein.

In some embodiments, proton translocation activity is determined, measured, detected or assayed by a method comprising a two-electrode voltage clamping on *Xenopus laevis* oocytes, patch clamping transfected HEK-293 cells, or imaging intracellular pH indicators. For example, in certain embodiments, a nucleic acid encoding an otopetrin polypeptide protein, a functional portion thereof, or a homolog thereof is injected into *Xenopus* oocytes thereby mediating the expression and integration of an otopetrin polypeptide into the oocyte membrane. Proton translocation activity can then be assessed by measuring changes in membrane polarization, (e.g., changes in membrane potential). In certain embodiments, proton translocation activity is determined by measuring pH and/or changes in pH (e.g., changes in intracellular pH) with a suitable pH sensitive indicator. A pH sensitive indicator can by a pH sensitive dye (e.g., pHrodo Red) or pH sensitive protein (e.g., a pH sensitive green fluorescent protein (GFP), or pHluorin). In some embodiments pH and/or changes in pH can be measured with pHrodo Red. In certain embodiments, proton translocation activity is determined by measuring changes in intracellular $Ca^{2+}$ or Zinc levels. For example, calcium levels can be measured by using fluorescent calcium indicator dyes such as Fura-2. In a typical microfluorimetry assay, a dye such as Fura-2, which undergoes a change in fluorescence upon binding a single $Ca^{2+}$ ion, is loaded into the cytosol of Otop-expressing cells. Upon exposure to a test compound, an increase in cytosolic calcium is reflected by a change in fluorescence of Fura-2 that occurs when calcium is bound.

In some embodiments, the proton translocation activity of an otopetrin polypeptide is assessed indirectly using a variety of in vitro and in vivo assays to determine functional, chemical, and physical effects, e.g., measuring the binding of an otopetrin to other molecules (e.g., peptide, signaling molecules, including peptides, small organic molecules, and lipids); and/or measuring increases or decreases in protein expression (e.g., transcription, protein levels, etc.) in response to intracellular pH changes that result from otopetrin-dependent proton translocation. In some embodiments, proton translocation activity is determined by assessing changes in cell growth or viability where such events are mediated by otopetrin-dependent proton translocation. In certain embodiments, proton translocation activity is determined or measured indirectly by detecting changes in amounts, or detecting modifications (e.g., phosphorylation) of intracellular second messengers (e.g., IP3, cGMP or cAMP), where such amounts or modifications are regulated or induced by otopetrin-dependent proton translocation.

In certain embodiment, proton translocation activity is determined using a patch clamp technique on a cell or oocytes comprising a membrane integrated otopetrin polypeptide, or functional portion thereof. In some embodiments, the presence of otopetrin-dependent proton translocation activity is determined as a net change in current of at least 0.1 pA, at least 1 pA, at least 5 pA, at least 10 pA, at least 50 pA, at least 100 pA, at least 500 pA, at least 1000 pA, at least 50 nA, at least 100 nA, at least 500 nA, at least 0.1 µA, at least 0.2 µA, at least 0.5 µA, at least 1.0 µA, or at least 2 µA in response to pH change of at least 0.1 pH units. In some embodiments, a change in current is determined, measured or detected by measuring or detecting a corresponding change in resistance or voltage potential, which parameters are readily converted using a suitable mathematical algorithm. In some embodiments, a modulation of otopetrin-dependent proton translocation activity is a net change (e.g., an increase or decrease of proton translocation activity) in otopetrin-dependent proton translocation activity of at least 10%, at least 25%, at least 50%, at least 75%, at least 2-fold, at least 5-fold or at least 10-fold. A net change can be determined by comparing an otopetrin-mediated proton translocation activity determined in the absence of a test compound to an otopetrin-mediated proton translocation activity determined in the presence of a test compound. In some embodiments, an amount of otopetrin-mediated proton translocation activity determined in the absence of a test compound is referred to as a reference level or control. For example, a decrease in proton translocation activity, in some embodiments, is determined by comparing an amount of proton translocation activity of an otopetrin polypeptide in the presence of a test compound to the proton translocation activity of an otopetrin polypeptide determined in the absence of a test compound (e.g., a reference level). In certain embodiments, an increase in proton translocation activity is determined by comparing an amount of proton translocation activity of an otopetrin polypeptide in the presence of a test compound to the proton translocation activity of an otopetrin polypeptide determined in the absence of a test compound (e.g., a reference level).

DETAILED DESCRIPTION

Proton channels that can transport protons into eukaryotic cells have not been molecularly identified. An unbiased screen based on transcriptome profiling of taste cells was used to identify the transmembrane protein Otopetrin1 (Otop1) as encoding a proton-selective ion channel with novel biophysical properties. The related murine genes, Otop2 and Otop3 as well as the *Drosophila* gene dmO-TOPLc also encode proton channels. It was also determined herein that Otop1 is required for $Zn^{2+}$-sensitive proton conductance.

In some embodiments, presented herein is a method of identifying a modulator of an otopetrin-mediated proton translocation activity. In some embodiments, the method comprises contacting a test compound with an otopetrin polypeptide, or functional portion thereof, and determining a proton translocation activity mediated by an otopetrin polypeptide, or the functional portion thereof. The term "determining" as used herein in the context of "determining a proton translocation activity" means and includes, but is not limited to "measuring", "detecting", and/or "obtaining".

Otopetrin Polypeptides

An otopetrin polypeptide, or functional portion thereof, is a multi-pass integral membrane protein that forms a channel in a lipid bilayer. Accordingly, an otopetrin polypeptide, or functional variant thereof, as referred to herein is an otopetrin polypeptide that is integrated into a lipid bilayer (e.g., a cell membrane, or synthetic lipid bilayer). When integrated into a cell membrane, an otopetrin polypeptide comprises a first side (e.g., an extracellular side) and a second side (e.g., an intracellular side). As shown herein, an otopetrin polypeptide provides translocation of protons from one side of the otopetrin polypeptide (e.g., one side of a membrane) to the other side of the otopetrin polypeptide (e.g., the other side of the membrane), often in response to a pH change (e.g., an increase or decrease in protons) on one side of a membrane. In some embodiments a change in pH is induced on one side of an otopetrin polypeptide (e.g., by addition of a base or an acid) followed by detecting proton translocation through the otopetrin polypeptide.

In some embodiments, an otopetrin polypeptide comprises or consists of an otopetrin polypeptide that is obtained, expressed, or derived from any suitable biological organism, non-limiting examples of which include animals, plants, protists, cnidaria (aquatic freshwater or marine animals), arthropods, fungi, bacteria, annelids, echinoderms, chordates, and mollusks, and the like. An otopetrin polypeptide can be obtained, expressed, or derived from any suitable species. An otopetrin polypeptide, in some embodiments comprises or consists of an insect derived otopetrin polypeptide (e.g., an otopetrin polypeptide, or functional portion thereof, derived from *Drosophila*). In certain embodiments, an otopetrin polypeptide comprises or consists of an otopetrin polypeptide that is obtained, expressed, or derived from a suitable mammal. In some embodiments, an otopetrin polypeptide comprises a mammal otopetrin polypeptide, non-limiting examples of which include Otopetrin-1 (Otop1), Otopetrin-2 (Otop2), and Otopetrin-3 (Otop3). In some embodiments, an otopetrin polypeptide comprises or consists of an otopetrin polypeptide that is obtained, expressed, or derived from a rodent, non-limiting examples of which include mice and rats. In certain embodiments, an otopetrin polypeptide comprises or consists of an otopetrin polypeptide that is obtained, expressed, or derived from a suitable primate. A primate can be a non-human primate or may include humans. In certain embodiments, an otopetrin polypeptide comprises, consists of, is obtained from, or is derived from a human otopetrin polypeptide, non-limiting examples of which include Otopetrin-1 (Otop1; UniProtKB-Q7RTM1; SEQ ID NO:1), Otopetrin-2 (Otop2; UniProtKB-Q7RTS6; SEQ ID NO:2), and Otopetrin-3 (Otop3; UniProtKB-Q7RTS5; SEQ ID NO:3). In certain embodiments, an otopetrin polypeptide comprises a mouse otopetrin polypeptide non-limiting examples of which include Otopetrin-1 (Otop1; UniProtKB-Q80VM9; SEQ ID NO:4), Otopetrin-2 (Otop2; UniProtKB-Q80SX5; SEQ ID NO:5), Otopetrin-3 (Otop3; UniProtKB-Q8OUF9; SEQ ID NO:6), or a functional portion thereof. In certain embodiments, an otopetrin polypeptide comprises or consists of an otopetrin polypeptide that comprises, consists of, a *Drosophila* Otop polypeptide, non-limiting examples of which include *Drosophila* OTOP variant D (NM_001272325.1 (CG42492))(SEQ ID NO: 7), *Drosophila* OTOP variant A (NM_134914.3 (CG332))(SEQ ID NO: 8), and *Drosophila* OTOP variant D (NM 001144688.3 (CG42265))(SEQ ID NO: 9). An otopetrin polypeptide can be expressed in a cell membrane of a cell using a suitable nucleic acid (e.g., a cDNA) that encodes an otopetrin polypeptide. In some embodiments, a suitable cell is transfected with a cDNA encoding an otopetrin polypeptide. Non-limiting examples of a cDNA that encodes a *Drosophila* otopetrin polypeptide are provided in NCBI reference numbers NM_001272325.1 (CG42492), NM_134914.3 (CG332) and NM 001144688.3 (CG42265).

In certain embodiments an otopetrin polypeptide comprises one or more amino acid additions, deletions or substitutions. An otopetrin polypeptide can be at least 80%, at least 85%, at least 90%, at least 95%, at least 96%, at least 97%, at least 98%, at least 99%, or 100% identical to an otopetrin polypeptide described herein. In certain embodiments, an otopetrin polypeptide comprises or consists of an otopetrin polypeptide that is at least 80%, at least 85%, at least 90%, at least 95%, at least 96%, at least 97%, at least 98%, at least 99%, or 100% identical to an otopetrin polypeptide sequence of any one of SEQ ID Nos: 1, 2, 3, 4, 5, or 6. In some embodiments, an otopetrin polypeptide comprises one or more amino acid analogs or one or more modified amino acids. Modified otopetrin polypeptides that comprise amino acid substitutions, amino acid deletions, amino acid additions, or amino acid analogs can be prepared by a suitable method for altering peptide sequences, non-limiting examples of which are described in *Molecular Cloning: A Laboratory Manual*, J. Sambrook, et al., eds., Second Edition, Cold Spring Harbor, or *Current Protocols in Molecular Biology*, F. M. Ausubel, et al., eds., John Wiley & Sons, Inc. New York. An otopetrin polypeptide can also be modified and made using suitable recombinant nucleic acid technology.

The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

In certain embodiments, an otopetrin polypeptide described herein provides any amount of detectable proton translocation activity. In certain embodiments, an otopetrin polypeptide for use in a method described herein is naturally occurring, truncated, mutated, or genetically altered while retaining any amount of detectable proton translocation activity. In some embodiments, an otopetrin polypeptide described herein retains at least 5%, at least 10%, at least 20%, at least 30%, at least 40%, at least 50%, at least 55%, at least 60%, at least 65%, at least 70%, at least 75%, at least 80%, at least 85%, at least 90%, at least 95%, at least 97%, at least 98%, at least 99% or more of the proton translocation activity of a wild-type otopetrin polypeptide peptide sequence. In some embodiments, an otopetrin polypeptide described herein retains at least 5%, at least 10%, at least 20%, at least 30%, at least 40%, at least 50%, at least 55%, at least 60%, at least 65%, at least 70%, at least 75%, at least 80%, at least 85%, at least 90%, at least 95%, at least 97%, at least 98%, at least 99% or more of the proton translocation activity of an otopetrin polypeptide of any one of SEQ ID Nos: 1, 2, 3, 4, 5, 6, 7, 8 or 9.

In certain embodiments, an otopetrin polypeptide comprises a functional portion of an otopetrin polypeptide described herein. A function portion of an otopetrin polypeptide is any portion of an otopetrin polypeptide that, when integrated into a membrane, displays proton translocation activity as measured by a method described herein. A functional portion of an otopetrin polypeptide can be made and/or expressed using a suitable recombinant method known in the arts and can be tested for proton translocation activity by a method described herein. Accordingly, one of skill in the art can readily identify a functional portion of an otopetrin polypeptide using the methods described herein. A functional portion of an otopetrin polypeptide, in certain embodiments, retains at least 5%, at least 10%, at least 20%, at least 30%, at least 40%, at least 50%, at least 60%, at least 70%, at least 80%, at least 90%, at least 95% or 100% of the proton translocation activity of a wild type otopetrin polypeptide (e.g., an otopetrin polypeptide of any one of SEQ ID Nos: 1 to 9).

In some embodiments, an otopetrin polypeptide, or functional portion thereof, is linked, covalently or otherwise to another polypeptide, nucleic acid, carbohydrate, fatty acid or detectable reagent. In certain embodiments, an otopetrin polypeptide, or functional portion thereof, comprises another polypeptide. In certain embodiments, an otopetrin polypeptide or functional portion thereof, may be linked covalently to another polypeptide, or portion thereof, while retaining proton translocation activity. In some embodiments, an otopetrin polypeptide is linked to another transmembrane protein, or portion thereof.

In some embodiments, an otopetrin polypeptide is linked (covalently or non-covalently) to a distinguishable identifier. In some embodiments an otopetrin polypeptide comprises one or more distinguishable identifiers. Any suitable distinguishable identifier can be linked to or associated with an otopetrin polypeptide. In some embodiments, a distinguishable identifier is a detectable label. Non-limiting examples of a distinguishable identifier include a metallic label, a fluorescent label, a fluorescent protein (e.g., green fluorescent protein (GFP)), a pH sensitive protein or pH sensitive GFP (e.g., a pHluorin, or the like), any suitable fluorophore (e.g., mCherry), a chromophore, a chemiluminescent label, an electro-chemiluminescent label (e.g., Origen™), a phosphorescent label, a quencher (e.g., a fluorophore quencher), a fluorescence resonance energy transfer (FRET) pair (e.g., donor and acceptor), a protein (e.g., an enzyme (e.g., horseradish peroxidase, β-galactosidase, luciferase, alkaline phosphatase and the like)), an antigen or part thereof, a linker, a member of a binding pair), an enzyme substrate, a small molecule (e.g., biotin, avidin), a mass tag, quantum dots, nanoparticles, the like or combinations thereof. Any suitable fluorophore or light emitting material can be used as a distinguishable identifier. A light emitting distinguishable identifier can be detected and/or quantitated by a variety of suitable techniques such as, for example, flow cytometry, gel electrophoresis, protein-chip analysis (e.g., any chip methodology), microarray, mass spectrometry, cytofluorimetric analysis, fluorescence microscopy, confocal laser scanning microscopy, laser scanning cytometry, the like and combinations thereof. In some embodiments, an otopetrin polypeptide is fused to GFP. In some embodiments an otopetrin polypeptide is fused to a pHluorin.

In certain embodiments a distinguishable identifier is indirectly associated with (e.g., bound to) an otopetrin polypeptide. In some embodiments a distinguishable identifier is reversibly associated with an otopetrin polypeptide. In certain embodiments a distinguishable identifier that is reversibly associated with an otopetrin polypeptide can be removed from an otopetrin polypeptide using a suitable method (e.g., by increasing salt concentration, denaturing, washing, adding a suitable solvent and/or salt, adding a suitable competitor, and/or by heating).

Proton Translocation Activity

As described herein (e.g., see Examples), an otopetrin polypeptide is a multipass transmembrane protein that when integrated into a lipid bilayer, forms an ion channel or pore that selectively allows translocation of protons from one side of the lipid bilayer to the other side. Accordingly, the phrase "proton translocation activity" refers to translocation of protons through an ion channel or pore formed by an otopetrin polypeptide, or functional portion thereof, from one side of a lipid bilayer to the other side of the lipid bilayer. Proton translocation activity can be an active or passive process. In some embodiments proton translocation activity by an otopetrin polypeptide is a passive process. Proton translocation activity of a membrane-integrated otopetrin polypeptide can be assayed or measured using a suitable in vitro or in vivo method. The translocation of protons across or through a channel or pore formed by an otopetrin polypeptide can be determined, measured, detected or assayed directly (e.g., by directly measuring or detecting changes (e.g., increases or decreases) in intracellular pH, current, resistance or voltage potential), or indirectly (e.g., by measuring or detecting changes (e.g., increases or decreases) in intracellular calcium or zinc (e.g., by imaging, e.g., calcium imaging)), by detecting otopetrin-mediated cell signaling or other otopetrin-mediated events, or by measuring or detecting (e.g., by imaging) light emitted from pH sensitive indicator. Non-limiting examples of a pH sensitive indicator includes pH sensitive fluorophores, pH sensitive dyes, pH sensitive proteins, the like and combinations thereof. In some embodiments a pH sensitive indicator comprises a pHluorin. In some embodiments, a pH sensitive indicator comprises pHrodo Red. The pH sensitive indicator pHrodo Red is weakly fluorescent at neutral pH but becomes increasingly fluorescent as pH decreases. This reagent can be used to quantify cellular cytosolic pH. Any suitable pH indicator can be used for a method described herein to detect changes in pH (intracellular or extracellular), non-limiting examples of which are listed in Invitrogen's Molecular Probes Handbook, *A Guide to fluorescent probes and labeling technologies*, (2010) 11$^{th}$ Edition, Chapter 20.

In some embodiments, proton translocation activity is determined, measured, detected or assayed by a method comprising voltage clamping (e.g., a two-electrode voltage clamping on *Xenopus laevis* oocytes or patch clamping transfected HEK-293 cells), or imaging intracellular pH indicators. For example, in certain embodiments, a nucleic acid encoding an otopetrin polypeptide protein, a functional portion thereof, or a homolog thereof is injected into *Xenopus* oocytes thereby mediating the expression and integration of an otopetrin polypeptide into the oocyte membrane. Proton translocation activity can then be assessed by measuring current or by measuring changes in membrane polarization, (e.g., changes in membrane potential). In certain embodiments, proton translocation activity is determined by measuring changes in intracellular pH by use of a pH indicator such as a pHluorin. In certain embodiments, proton translocation activity is determined by measuring changes in intracellular $Ca^{2+}$ levels. For example, calcium flux can be measured by assessment of the uptake of $Ca^{2+}$ or by using fluorescent dyes such as Fura-2. In a typical microfluorimetry assay, a dye such as Fura-2, which undergoes a change in fluorescence upon binding a single $Ca^{2+}$ ion, is loaded into the cytosol of Otop-expressing cells. Upon exposure to a test compound, an increase in cytosolic calcium is reflected by a change in fluorescence of Fura-2 that occurs when calcium is bound. Other suitable fluorescent calcium indicators can also be used for a method disclosed herein.

In some embodiments, the proton translocation activity of an otopetrin polypeptide is assessed indirectly using a variety of in vitro and in vivo assays to determine functional, chemical, and physical effects, e.g., measuring the binding of an otopetrin to other molecules (e.g., peptide, signaling molecules, including peptides, small organic molecules, and lipids); and/or measuring increases or decreases in protein expression (e.g., transcription, protein levels, etc.) in response to intracellular pH changes that result from otopetrin-dependent proton translocation. In some embodiments, proton translocation activity is determined by assessing changes in cell growth or viability where such events are mediated by otopetrin-dependent proton translocation. In certain embodiments, proton translocation activity is determined or measured indirectly by detecting changes in amounts, or detecting modifications (e.g., phosphorylation) of intracellular second messengers (e.g., IP3, cGMP or cAMP), where such amounts or modifications are regulated or induced by otopetrin-dependent proton translocation.

In some embodiments, proton translocation activity of an otopetrin polypeptide, or functional portion thereof, is determined by measuring or detecting a change in current, resistance or voltage potential across a lipid bilayer. A lipid bilayer can be lipid bilayer of a cell or may be synthetic. In some embodiments, proton translocation activity is determined in response to a change in pH (i.e. proton concentration) on one side of a lipid bilayer. In some embodiments, proton translocation activity is induced by a change in pH (i.e. proton concentration) on one side of a lipid bilayer. A change in pH can be provided by the addition of protons (e.g., an acid) to the fluid on one side of a membrane. A change in pH can be an increase or decrease in pH. In some embodiments, a change in pH is a change of at least 0.01, at least 0.05, at least 0.1, at least 0.5, or at least 1.0 pH unit. In some embodiments a change is pH is a change of at least 0.5 pH units. A change in pH can be provided on either side of a membrane. In certain embodiments, protons are added to the extracellular side of a membrane thereby providing an extracellular change in pH. Non-limiting examples of methods that can be used to determine, assay, or measure proton translocation activity include any suitable version of a patch clamp technique (e.g., cell-attached patch, inside-out patch, whole cell recording, outside-out patch, perforated patch, loose patch, a two-electrode voltage claim and a mammalian cell patch clamp (e.g., using transfected HEK-293 cells)), mammalian cell—pH imaging with a dye (e.g., DFFDA BCECF, pHrodo red or Fura 2-AM (Sigma Aldrich, CA no. 108964-32-5)) or by co-transfection with a pHluorin, for example, and imaging (e.g., calcium imaging), the like and combinations thereof. Additional non-limiting examples of methods that can be used to determine, assay, or measure proton translocation activity can found in Tsien R Y, Biochemistry (1980) 19(11):2396-404; Rink T J, Tsien R Y, Pozzan T., (1982) J. Cell Biol. 95(1):189-96; Grynkiewicz G, Poenie M, Tsien R Y. (1985) J Biol Chem. 260(6):3440-5; Tsien R Y, (1989) Methods Cell Biol. 30:127-56; Cohen-Armon M, Sokolovsky M, Dascal N., (1989) Brain Res. 496(1-2):197-203; Liman E R, Tytgat J, Hess P., (1992) Neuron. 9(5):861-71; Shimbo K, Brassard D L, Lamb R A, Pinto L H., (1996) Biophys J. 70(3):1335-46; and Chang R B, Waters H, Liman E R., (2010) Proc. Natl. Acad. Sci. (USA) 107(51):22320-5. The entire contents of the foregoing references are incorporated herein by reference.

In certain embodiment, proton translocation activity is determined using a voltage clamp technique on a cell or oocytes comprising a membrane integrated otopetrin polypeptide, or functional portion thereof. In some embodiments, the presence of otopetrin-dependent proton translocation activity is determined as a net change in current of at least 50 pA, at least 100 pA, at least 500 pA, at least 1000 pA, at least 50 nA, at least 100 nA, at least 500 nA, at least 0.1 µA, at least 0.2 µA, at least 0.5 µA, at least 1.0 µA, or at least 2 µA in response to pH change of at least 1 pH unit.

In some embodiments, proton translocation activity is determined using a fluorescent-imaging plate reader (FLIPR). The FLIPR was a first-in-class instrument that utilized charge-coupled device imaging of a whole plate to capture fluorescent readouts (Schroeder and Neagle (1996) J. Biomol. Screen. 1:pp. 75-80; also see Chemistry & Biology (2014) 21(9):1162-1170). In certain embodiments, a system comprises a FLIPR. In some embodiments, a system is a high throughput system comprising a FLIPR.

In some embodiments, a change in current is determined, measured or detected directly. In some embodiments, a change in current is determined, measured or detected by measuring or detecting a corresponding change in resistance or voltage potential, which parameters are readily converted using a suitable mathematical algorithm. In some embodiments, a modulation of otopetrin-dependent proton translocation activity is a net change (e.g., an increase or decrease of proton translocation activity) in otopetrin-dependent proton translocation activity of at least 1%, at least 2%, at least 3%, at least 4%, at least 5%, at least 10%, at least 25%, at least 50%, at least 75%, at least 2-fold, at least 5-fold or at least 10-fold. A net change can be determined by comparing an otopetrin-mediated proton translocation activity determined in the absence of a test compound to an otopetrin-mediated proton translocation activity determined in the presence of a test compound. In some embodiments, an amount of otopetrin-mediated proton translocation activity determined in the absence of a test compound is referred to as a reference level or control. For example, a decrease in proton translocation activity, in some embodiments, is determined by comparing an amount of proton translocation activity of an otopetrin polypeptide in the presence of a test compound to the proton translocation activity of an otopetrin polypeptide determined in the absence of a test compound (e.g., a reference level). In certain embodiments, an increase in proton translocation activity is determined by comparing an amount of proton translocation activity of an otopetrin polypeptide in the presence of a test compound to the proton translocation activity of an otopetrin polypeptide determined in the absence of a test compound (e.g., a reference level).

The term "decrease" or "reduced", and grammatical variations thereof, as used herein, means a decrease of at least 1%, at least 2%, at least 3%, at least 4%, at least 5%, at least 10%, at least 25%, at least 50%, at least 75%, at least 2-fold, at least 5-fold or at least 10-fold as compared to a reference level or control. In certain embodiments, a test compound that induces a decrease in the proton translocation activity of an otopetrin polypeptide is identified by a method described herein as a modulator of otopetrin-mediated proton translocation activity. A test compound or modulator that decreases or reduces the otopetrin-mediated proton translocation activity of an otopetrin polypeptide is referred to herein as an antagonist (e.g., an antagonist of an otopetrin polypeptide, an antagonist of otopetrin-mediated proton translocation activity).

The term "increase" or "enhance", and grammatical variations thereof, as used herein, means an increase of at least 1%, at least 2%, at least 3%, at least 4%, at least 5%, at least 10%, at least 25%, at least 50%, at least 75%, at least 2-fold, at least 5-fold or at least 10-fold as compared to a reference level or control. In certain embodiments, a test compound that induces an increase in the proton translocation activity of an otopetrin polypeptide is identified by a method described herein as a modulator of otopetrin-mediated proton translocation activity. A test compound or modulator that increases or enhances the otopetrin-mediated proton translocation activity of an otopetrin polypeptide is referred to herein as an agonist (e.g., an agonist of an otopetrin polypeptide, an agonist of otopetrin-mediated proton translocation activity).

In some embodiments, otopetrin-binding compounds are screened for agonistic or antagonist action in a functional assay that monitors a biological activity associated with otopetrin function such as effects upon intracellular levels of protons in a otopetrin-expressing host cell (e.g., protons, calcium, zinc), pH-activated conductance, cell death (i.e.; receptor-mediated cell death which can be monitored using, e.g., morphological assays, chemical assays, or immunological assays), depolarization of the otopetrin-expressing cells (e.g., using fluorescent voltage-sensitive dyes), second messenger production which can be detected by radioimmunoassay or ELISA), calcium-induced reporter gene expression, or other readily assayable biological activity associated with otopetrin activity or inhibition of otopetrin activity. In certain embodiments, a functional assay is based upon detection of a biological activity of otopetrin that can be assayed using high-throughput screening of multiple samples simultaneously, e.g., a functional assay based upon detection of a change in fluorescence which in turn is associated with a change in otopetrin activity. Such functional assays can be used to screen candidate agents for activity as either otopetrin agonists or antagonists.

In some embodiments, otopetrin-expressing cells (e.g., recombinant otopetrin-expressing cells) are pre-loaded with fluorescently-labeled pH indicators (e.g., pHrod Red). The Otopetrin-expressing cells are then exposed to a candidate otopetrin-binding compound and the effect of exposure to the compound is monitored. Candidate compounds that have otopetrin agonist activity are often those that, when contacted with the otopetrin-expressing cells, elicit a otopetrin-mediated change in intracellular pH or intracellular calcium relative to control cells (e.g., otopetrin-expressing cells in the absence of the candidate compound, host cells without otopetrin-encoding nucleic added). Similarly, functional otopetrin assays can be used to identify candidate compounds that block activity of otopetrins (e.g., block the change in intracellular pH induced by a change in extracellular pH).

In some embodiments, a method of identifying a modulator of otopetrin-mediated proton translocation activity comprises a high-throughput screening process. High-throughput screening (HTS) is a method for scientific discovery that uses robotics, data processing and control software, liquid handling devices, and sensitive detectors to screen thousands to millions of test compounds in a relatively short period of time. Any suitable High-Throughput Screening process can be used for a method described herein, non-limiting examples of which are described in U.S. Pat. Nos. 5,976,813; 6,472,144; 6,692,856; 6,824,982; and 7,091,048, the entire contents of which are herein incorporated by reference.

In some embodiments, a difference in proton translocation activity is determined. A difference in proton translocation activity can be determined by comparing a first proton translocation activity determined in the absence of a test compound, and a second proton translocation activity determined in the presence of a test compound. In certain embodiments, identifying a test compound as a modulator of an otopetrin proton translocation activity comprises determining a difference in proton translocation activity of at least 1%, at least 2%, at least 3%, at least 4%, at least 5%, at least 10%, at least 20%, at least 30%, at least 50%, at least 80%, at least 90%, at least 100%, at least 2-fold, at least 5-fold or at least 10-fold.

Test Compounds

Any suitable test compound can be tested by a method described herein. In some embodiments, a test compound is soluble in an aqueous medium (e.g., a cell culture medium) at a concentration tested. In some embodiments, a test compound is completely soluble in an aqueous medium at a concentration tested. In some embodiments, a test compound is partially soluble in an aqueous medium at a concentration tested. In certain embodiments, a test compound is not toxic to a mammalian cell at a concentration tested. For example, in certain embodiments, a test compound does not (i) inhibit growth, (ii) reduce viability, (iii) induce necrosis or apoptosis, (iv) induce damage of DNA or RNA, (v) damage a cell membrane, or (vi) induce proteolytic cleavage of cellular proteins, at a concentration tested. In some embodiments, a test compound is not a carcinogen or co-carcinogen. In some embodiments, a test compound is not a teratogen.

As used herein, the phrase "test compound" refers to any suitable compound that can be screened for the ability to specifically modulate the proton translocation activity of an otopetrin polypeptide. Non-limiting examples of a test compound include small compounds (e.g., small organic or inorganic molecules), large compounds (e.g., greater than 5000 Da), polysaccharides, carbohydrates, sugars, fatty acids, lipids, biological macromolecules, (e.g., peptides, polypeptides, proteins, peptide analogs and derivatives, peptidomimetics, nucleic acids, nucleotides, nucleotide analogs), naturally occurring or synthetic compounds, binding agents (e.g., antibodies, or binding fragments thereof, including non-naturally occurring and synthetic binding agents (e.g., TandAbs, nanobodies, aptamers, BiTEs, SMIPs, DARPins, DNLs, affibodies, Duocalins, adnectins, fynomers, Kunitz Domains Albu-dabs, DARTs, DVD-IG, Covx-bodies, peptibodies, scFv-Igs, SVD-Igs, dAb-Igs, Knob-in-Holes, triomAbs, and the like), derivatives thereof, polymers thereof, salts thereof, isomers thereof, polymorphs thereof, and combinations thereof. In some embodiments, a test compound is contained within an extract made from biological materials such as extracts of bacteria, plants, fungi, animal cells, or animal tissues. In some embodiments, a test compound is contained within a biological fluid. Accordingly, in some embodiments, a test compound comprises an extract or biological fluid. Small compounds may include molecules having a molecular weight greater than about 40 daltons (Da), but less than 5000 Da, less than 3000 Da, or less than 1000 Da. Small compounds may comprise any suitable chemical moiety or group, non-limiting examples of which include alkanes, alkenes, alkynes, alcohols, halogens, ketones, aldehydes, carboxylic acids, ethers, esters, amines, amides, saturated, partially saturated or unsaturated ring structures, nucleotides, nucleosides, polyatomic nonmetals (e.g., P, S, Se), transition metals, post-transition metals, metalloids, the like, salts thereof, and combinations thereof.

In certain embodiments, test compounds include synthetic or naturally occurring compounds of a suitable library. A multitude of small molecule libraries are known in the art, some of which are commercially available. Commercially available compound libraries can be obtained from, for example, ArQule, Pharmacopia, graffinity, Panvera, Vitas-M Lab, Biomol International and Oxford. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Chemical compound libraries from, for example, NIH Roadmap, Molecular Libraries Screening Centers Network (MLSCN) can also be used. Any suitable method can be used to make a small compound library. A compound library can be screened using a suitable HTS screening method and/or a method described herein to identified test compounds within the library that modulate an otopetrin-mediated proton translocation activity.

In certain embodiments, a test compound comprises a molecular weight of 40 to 500,000 Da, 40 to 200,000 Da, 40 to 100,000 Da, 40 to 50,000 Da, 40 to 25,000 Da, 40 to 10,000 Da, 40 to 5000 Da, or 40 to 1000 Da. In certain embodiments, a test compound comprises a molecular weight of 5000 to 500,000 Da, 10,000 to 500,000 Da, 25,000 to 500,000 Da, or 5000 to 100,000 Da.

A test compound can be tested at any suitable concentration. In some embodiments, a test compound is tested at a concentration of at least 1 pM, at least 10 pM, at least 100 pM, at least 1 nM, at least 10 nM, at least 100 nM, at least 1 µM, at least 10 µM, at least 100 µM or at least 1 mM. In some embodiments, a test compound is tested at a concentration in a range of 1 pM to 100 mM, 1 pM to 10 mM, 1 pM to 1 mM, 10 pM to 100 mM, 10 pM to 10 mM, 10 pM to 1 mM, 100 pM to 100 mM, 100 pM to 10 mM, or 100 pM to 1 mM. In some embodiments, a test compound is tested at a concentration of less than 100 mM, less than 10 mM, less than 1 mM or less than 100 nM. In some embodiments, a test compound is tested or assayed at one or more different concentrations.

In certain embodiments, a test compound comprises or consists of an electrophile. An electrophile is a compound capable of forming a covalent bound with an otopetrin polypeptide. In certain embodiments, a test compound comprises an enzyme (e.g., a protease).

Cells & Membranes

In certain embodiments an otopetrin polypeptide, or functional portion thereof, is associated with a cell membrane or a synthetic membrane. The phrase "associated with a cell membrane or a synthetic membrane" means that the otopetrin polypeptide, or functional portion thereof, is integrated into the membrane, thereby forming a functional proton channel comprising proton translocation activity.

An otopetrin polypeptide can be integrated into a lipid bilayer using a suitable method. An otopetrin polypeptide can be integrated into a lipid bilayer of a suitable cell, non-limiting examples of which include an animal cell, plant cell, a protist cell, a cell of an aquatic freshwater or marine animals, an arthropod cell, a fungi cell, a bacteria cell, an annelid cell, an echinoderm cell, a chordate cell, a mollusk cell, and the like. In certain embodiments, an otopetrin polypeptide is integrated into a lipid bilayer of a mammalian cell, a primate cell, a non-human primate cell or a human cell. In certain embodiments, a cell is a primary cell or an immortal cell (e.g., a tissue culture cell line), non-limiting examples of which include HeLa, HEK293, DU145, H295R, HT29, KBM-7, MCF-7, MDA-MB-468, PC3, THP-1, PC12, A549, CHO, COS, Caco-2, EL4, HEP G2, HL-60, the like, and derivatives thereof. In some embodiments, a cell is a taste receptor cell (e.g., a sour taste cell). In certain embodiments, a cell is an egg cell (e.g., an oocyte, e.g., a *Xenopus* oocyte). In certain embodiments, a cell is a red blood cell, or derivative thereof. In certain embodiments, a cell is a ghost cell, or an anucleated cell. An otopetrin polypeptide can be integrated into a lipid bilayer of a cell using any suitable method. In certain embodiments, an otopetrin polypeptide is integrated into a lipid bilayer of a cell by introducing a nucleic acid into the cell that directs the expression of an otopetrin polypeptide. Accordingly, in some embodiments a method described herein comprises expressing an otopetrin polypeptide, or functional portion thereof, in a cell. In some embodiments, therefore, a cell is a transfected cell, for example a cell transfected with a nucleic acid directing the expression of an otopetrin polypeptide or functional portion thereof. In some embodiments, a cell is a transduced cell, for example a cell transduced with a recombinant virus comprising a nucleic acid that directs the expression of an otopetrin polypeptide or functional portion thereof inside the transduced cell. In certain embodiments, a cell comprises an otopetrin polypeptide or functional portion thereof, integrated into the cell membrane of the cell. In certain embodiments, a cell comprises a heterologous otopetrin polypeptide, or functional portion thereof. The phrase "heterologous otopetrin polypeptide" indicates that the otopetrin polypeptide is derived from a different species than the cell that it is expressed in. In certain embodiments, a cell is *Xenopus* oocyte comprising a heterologous otopetrin polypeptide. In certain embodiments, a cell is taste receptor cell comprising a heterologous otopetrin polypeptide.

In certain embodiments, an otopetrin polypeptide is integrated into a suitable liposome, micelle, nanodisc, bilayer sheet, or bicelle for use in a method described herein. In certain embodiments, an otopetrin polypeptide is integrated into a suitable synthetic membrane for use in a method described herein. In some embodiments, an otopetrin is integrated into a suitable synthetic membrane formed in the aperture of a suitable nanopore device for use in a method described herein.

In certain embodiments, a nanopore device comprises a first fluid filled chamber and a second fluid filled chamber separated by an aperture comprising a synthetic membrane, wherein the membrane comprises one or more otopetrin polypeptides. In certain embodiments, the first fluid filled chamber comprises a first electrode and the second fluid filled chamber comprises a second electrode, where the first and second electrode are operatively linked to a means for measurement or detection of at least voltage potential, current, and/or resistance. In certain embodiments, a means for measurement or detection of voltage potential, current, and/or resistance is a device comprising an ammeter, voltmeter, ohmmeter, oscilloscope, the like or a combination thereof. In certain embodiments, the first and or second chamber comprises one or more photocells for detection of light emitting molecular probes.

In certain embodiments, provided herein, is a system for determining proton translocation activity of an otopetrin polypeptide. In certain embodiments, provided herein, is a system for identifying a modulator of proton translocation activity of an otopetrin polypeptide (i.e., a modulator or otopetrin-mediated proton translocation activity). In certain embodiments, a system comprises one or more otopetrin polypeptides integrated into a membrane, a first fluid-filled chamber and second fluid filled chamber, wherein the first fluid-filled chamber and the second fluid-filled chamber are located on opposing sides of the membrane. In certain embodiments, an aperture comprises the membrane. For example, in some embodiments, the system comprises an aperture and the membrane is housed within the aperture. In some embodiments, the membrane is a synthetic membrane. In some embodiments, the system comprises a nanopore device.

EXAMPLES

Figure 1B:
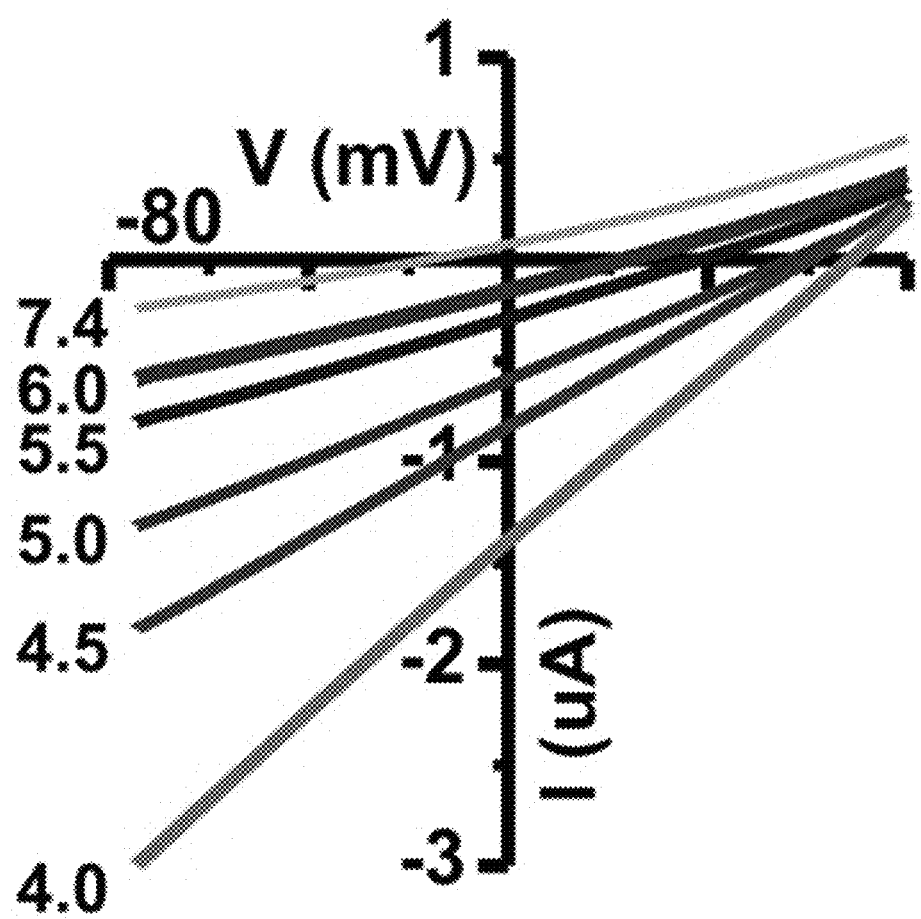

Example 1—Otop1 Forms a Proton-Selective Ion Channel with Unique Biophysical Properties To characterize the function properties of Otop1, we varied $pH_o$, and measured the evoked currents in *Xenopus* oocytes expressing Otop1. Unless otherwise noted, these and all other experiments were conducted with the large cation NMDG±, which is generally impermeable through ion channels, substituting for Na in the extracellular solution. Otop1 currents in *Xenopus* oocytes increased monotonically in magnitude as $pH_o$ was lowered over a range of pH 6-4 (FIGS. 1A-1C) and the reversal potential ($E_{rev}$) of the currents shifted toward more positive voltages. Note that because in these experiments endogenous and leak currents were not subtracted, the Otop1 currents deviate from Nernstian behavior[3,5].

Figure 1C:
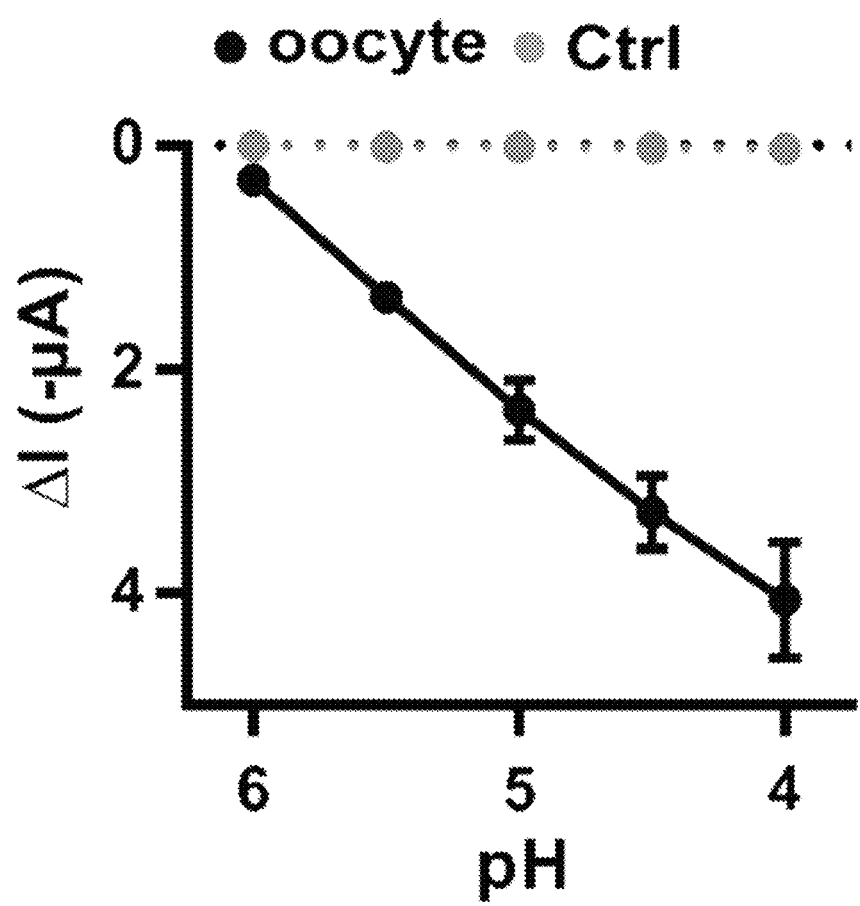
Figure 1D:
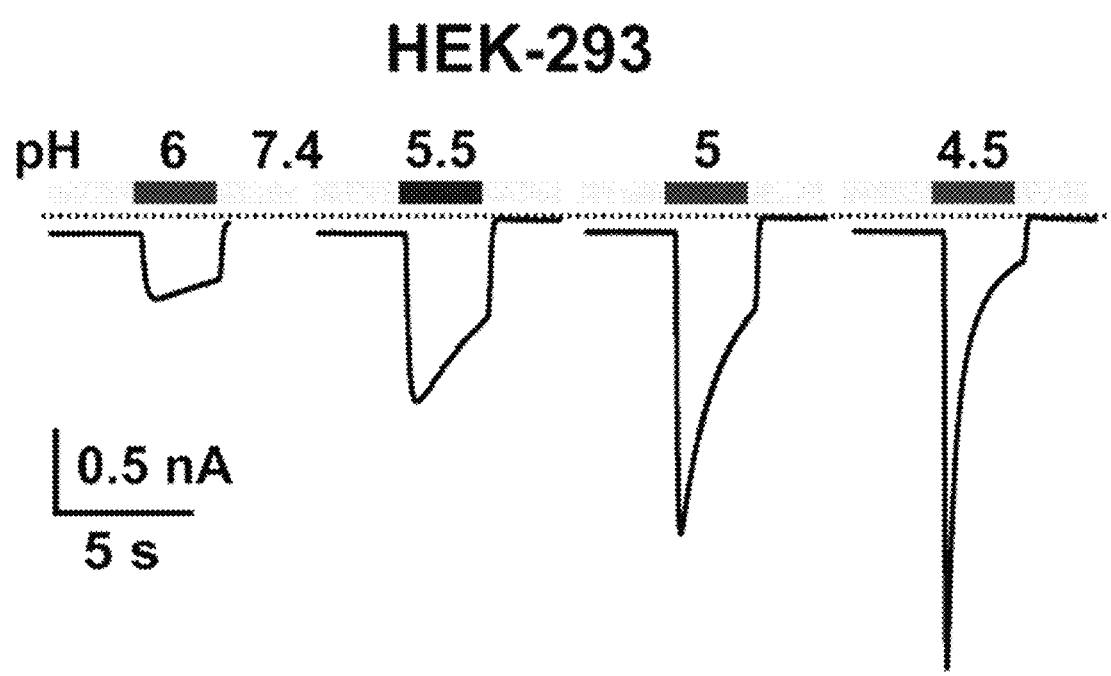
Figure 1E:
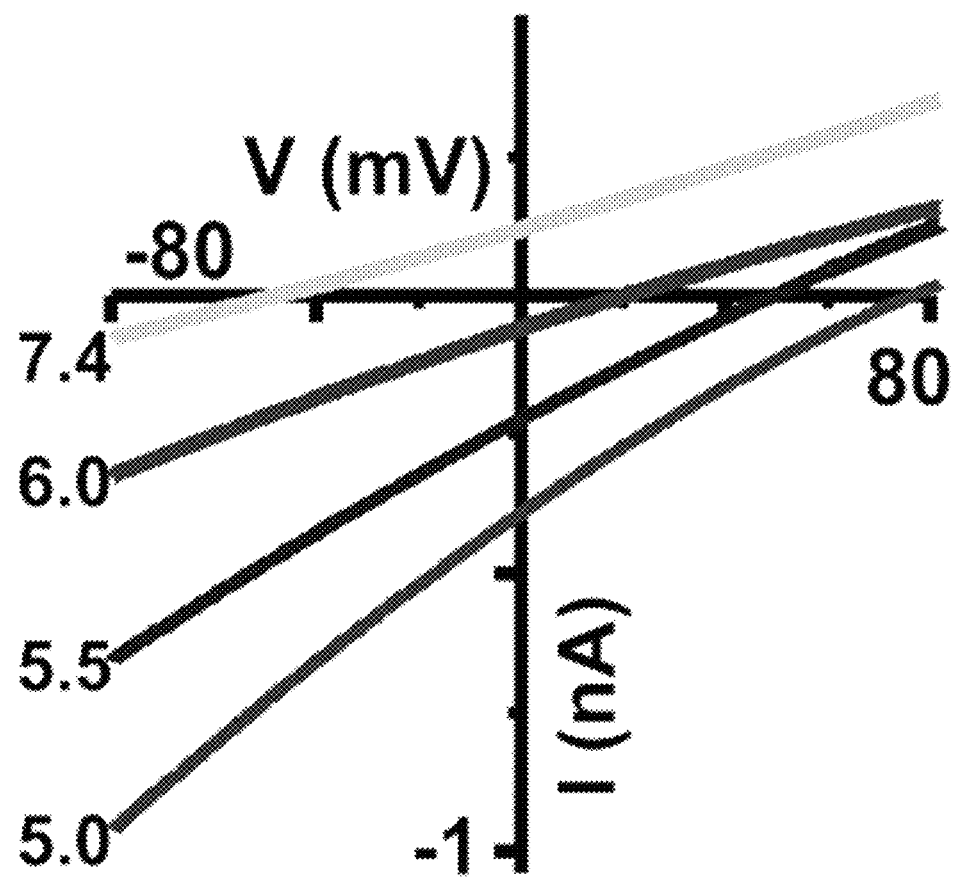
Figure 1F:
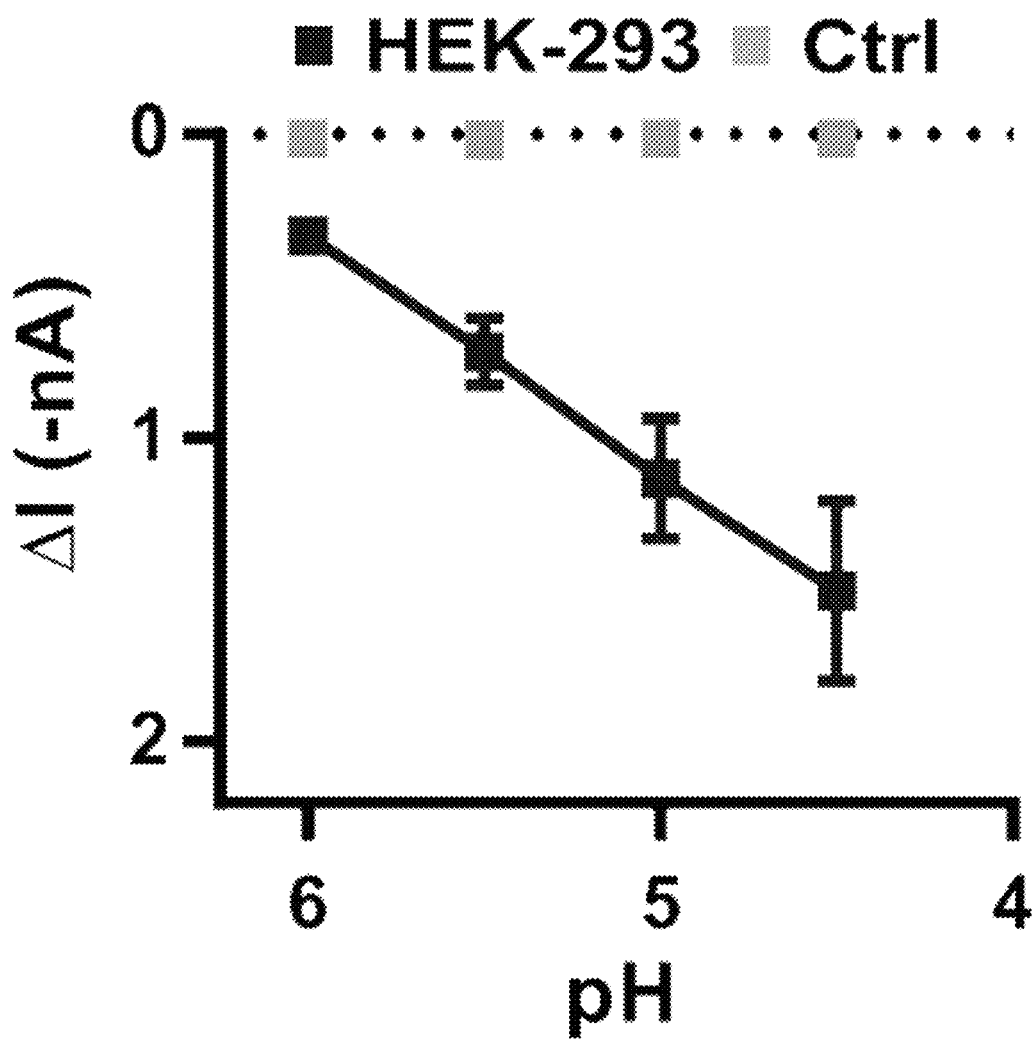
Figure 1G:
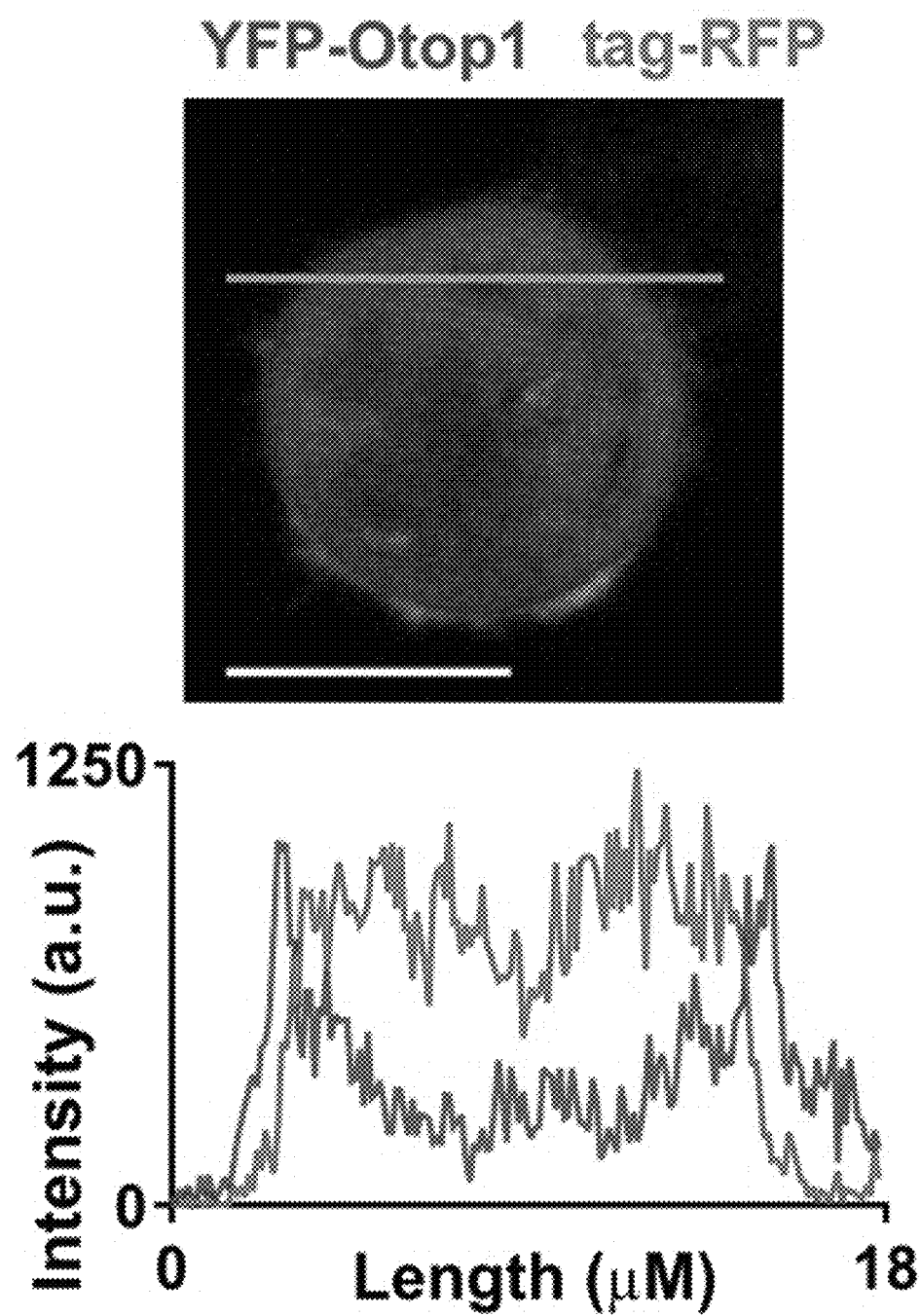
Figure 1H:
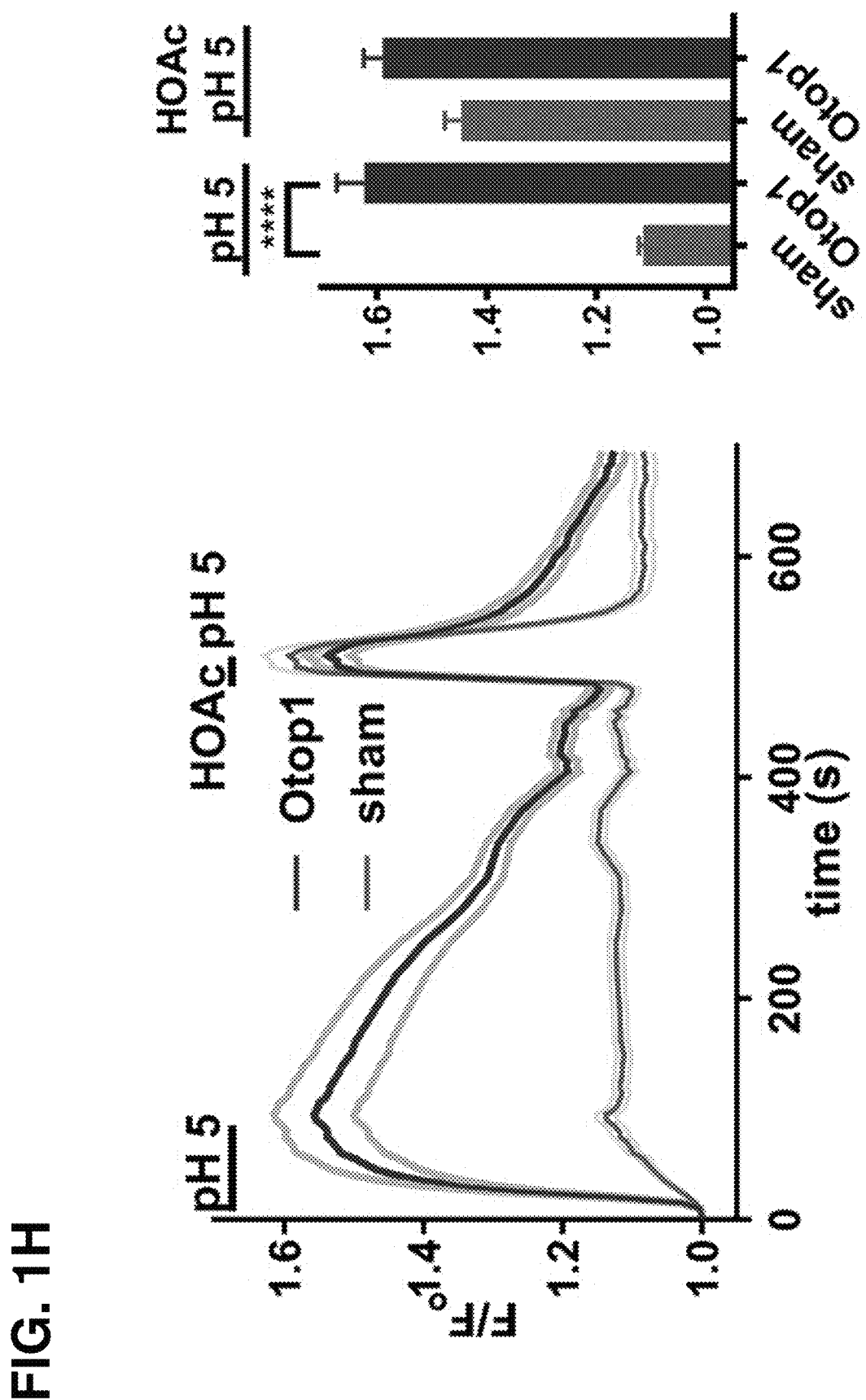

To determine if otop1 can generate the pore-forming subunit of an ion channel, irrespective of cellular context, we expressed it in HEK-293 cells (FIGS. 1D-1F). An N-terminal YFP-tagged channel confirmed expression at the cell surface (FIG. 1G). Large inward currents were elicited in response to lowering $pH_o$ in Otop1-transfected cells (I=1,130±192 pA for $pH_o$ =5.0, compared with 14±4 pA for untransfected cells) and the current magnitude increased monotonically with $pH_o$ (FIG. 1F), as it did in oocytes. Otop1 currents in HEK-293 cells decayed within seconds, with faster kinetics observed in response to more acidic stimuli (FIG. 1C). The decay of the currents may be due to accumulation (or depletion) of protons near the channel, which could the affect the driving force for proton movement or gating of the channels[3,5]. For example, an H⁺ current of 1000 pA, such as we observe, flowing for 1 second in a cell of 10 µm diameter (524 fL volume) can be calculated to increase the total (bound+free) intracellular concentration of H⁺ by up to 20 mM³. Moreover, removal of the excess H⁺ can take 60-90 seconds due to the slow diffusion of H⁺, which is bound to bulky pH buffers³. Indeed, when we imaged intracellular pH using the membrane permeant dye pHrodo Red, we observed a large change in $pH_i$ upon lowering $pH_o$ from 7.4 to 5.0 in Otop1-transfected cells, a response not observed in mock-transfected cells (FIG. 1H).

Figure 2B:
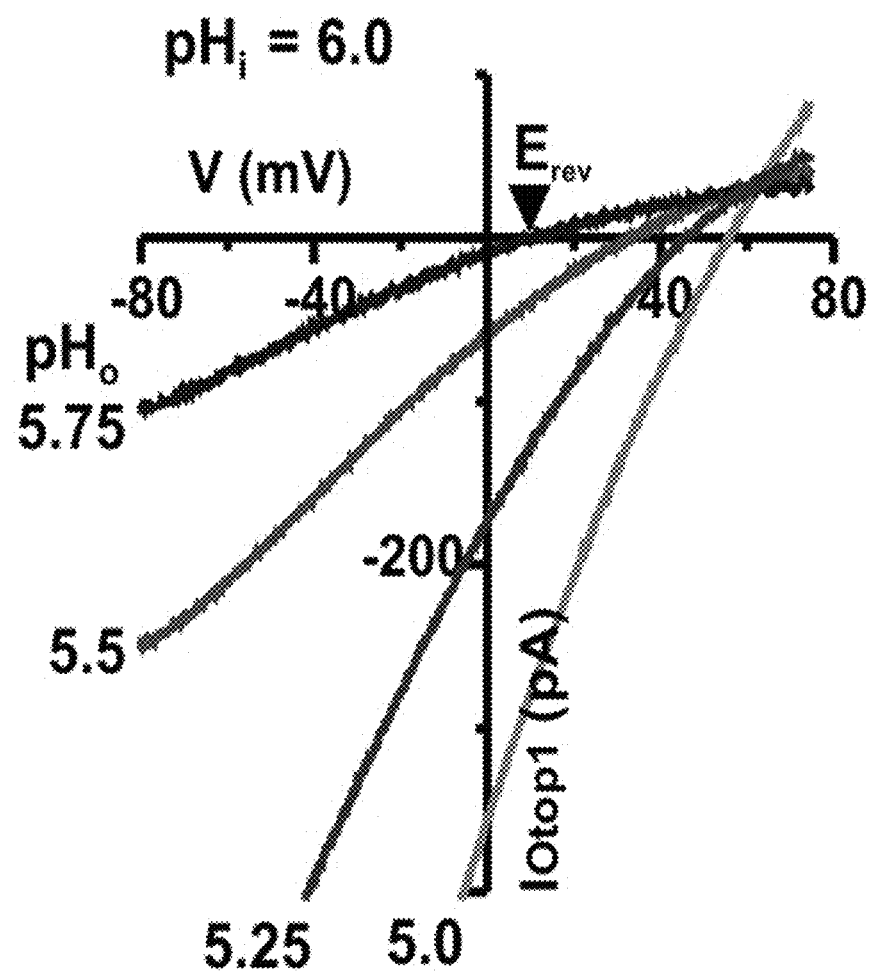
Figure 2C:
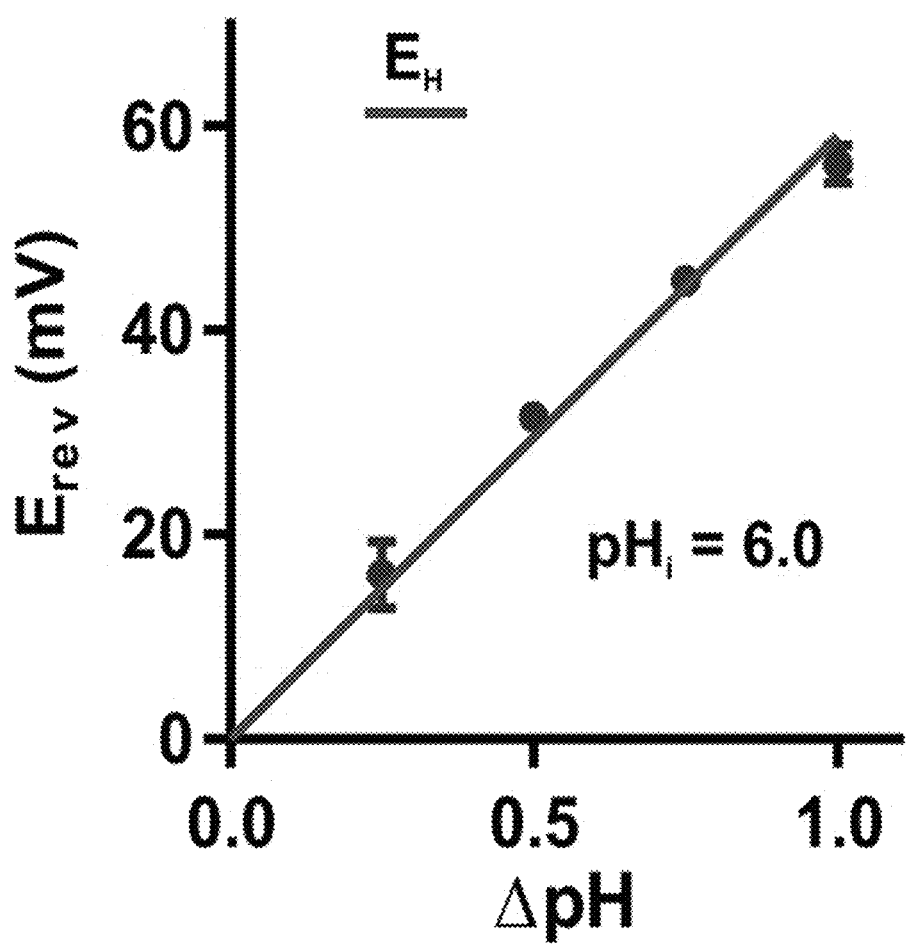

We carried out a detailed biophysical characterization of Otop1 to determine whether it is proton selective. First, we determined whether Otop1 is permeable to other cations by measuring responses to lowering pH while varying ionic conditions. Replacing NMDG⁺ in the extracellular solution with Na⁺ (FIG. 2A) did not change the amplitude of the current elicited in response to pH 5.5 (p>0.05 by paired t-test), indicating that the channel is not measurably permeable to Na⁺. Similarly, substitution of NMDG⁺ with Cs⁺, Li⁺ or Ca²⁺ caused a less than 3% increase in the current magnitude, indicating that Otop1 is also not appreciably permeable to these monovalent and divalent cations (FIG. 2A).

Figure 2D:
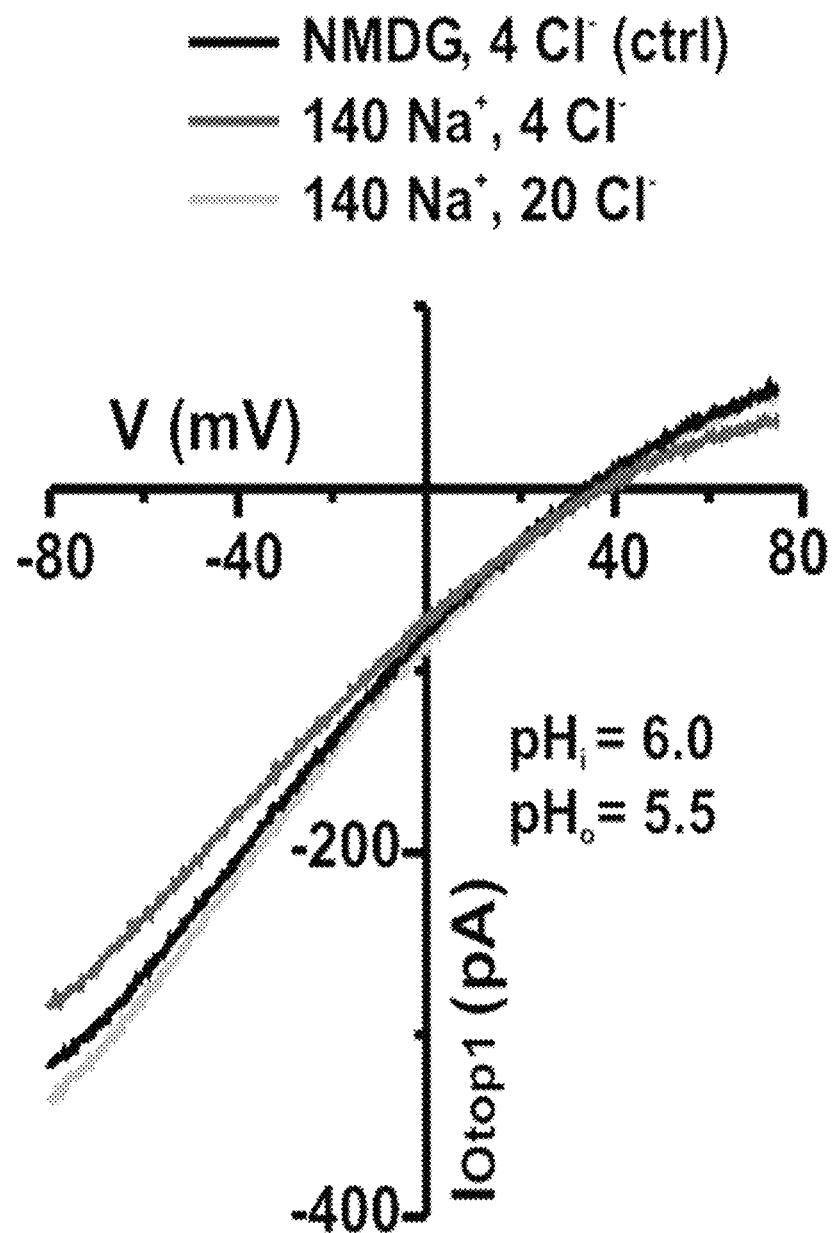

To determine the relative permeability of H⁺ to Na+ and Cl⁻, we measured $E_{rev}$ under conditions where 140 Na⁺ replaced 140 NMDG and where [Cl⁻] was increased, either in the presence or absence of Na⁺. In no case did we observe any change in $E_{rev}$ (FIGS. 2D and 2E). Using the Goldman-Hodgkin-Katz (GHK) equation[30], we calculate that a change of 5 mV, which would have been easily detectable, translates into a selectivity for H⁺ over Na⁺ of >2×10⁵-fold and a selectivity of H⁺ over Cl⁻ of >1×10⁵; as we observed no change in $E_{rev}$, it is possible that the channel is perfectly selective for H⁺ over Cl⁻ and Na⁺, like Hv1³.

Figure 2G:
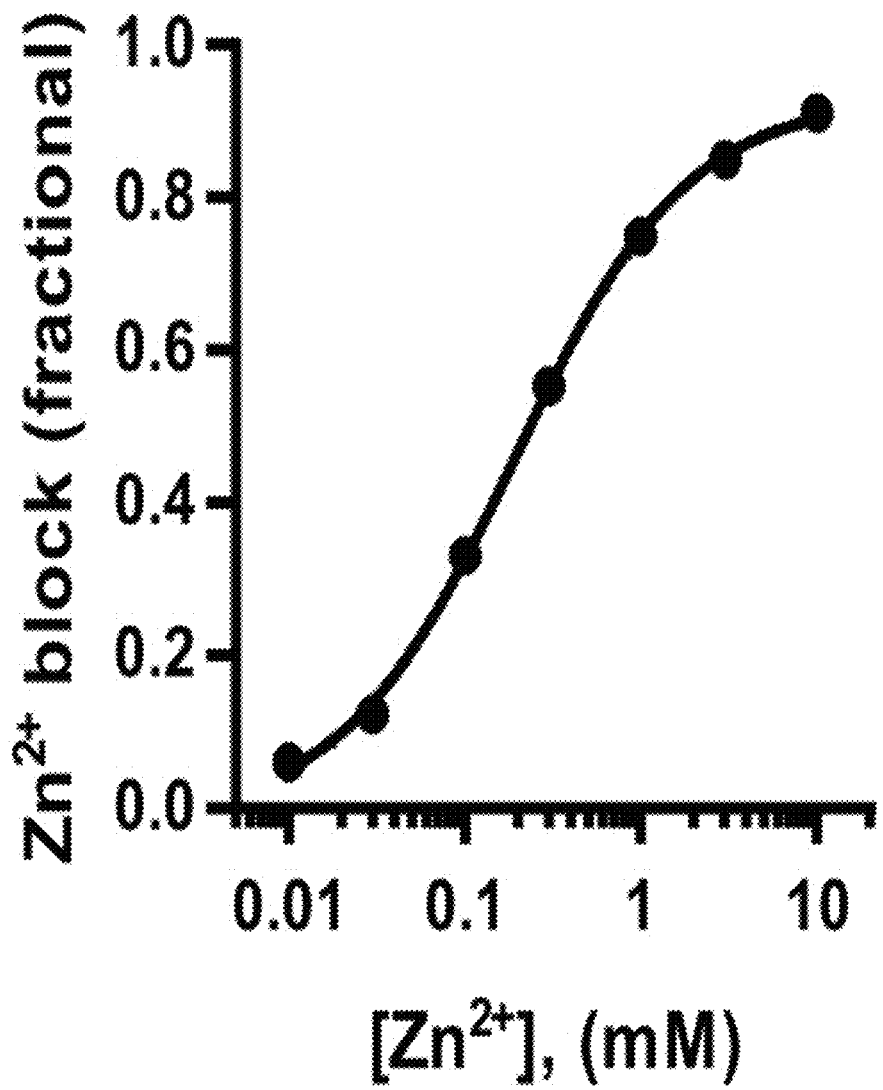

The transition metal Zn²⁺ is a potent inhibitor of Hv1, binding to two external histidine residues that regulate gating[7,31,32]. It also inhibits other molecules involved in proton transport³, including the proton channel in taste cells[20]. To gain insights into structural elements involved in ion permeation by Otop1, we measured its sensitivity to inhibition by Zn²⁺. Otop1 currents in HEK-293 cells evoked in response to pH 5.5 were inhibited by Zn²⁺ in a dose-dependent manner with an $IC_{50}$ of 0.19 mM±0.01 (FIGS. 2F and 2G). The Hill coefficient of close to one (0.89±0.06) indicates that a single Zn²⁺ ion binds to inhibit the channel.

Figure 5:
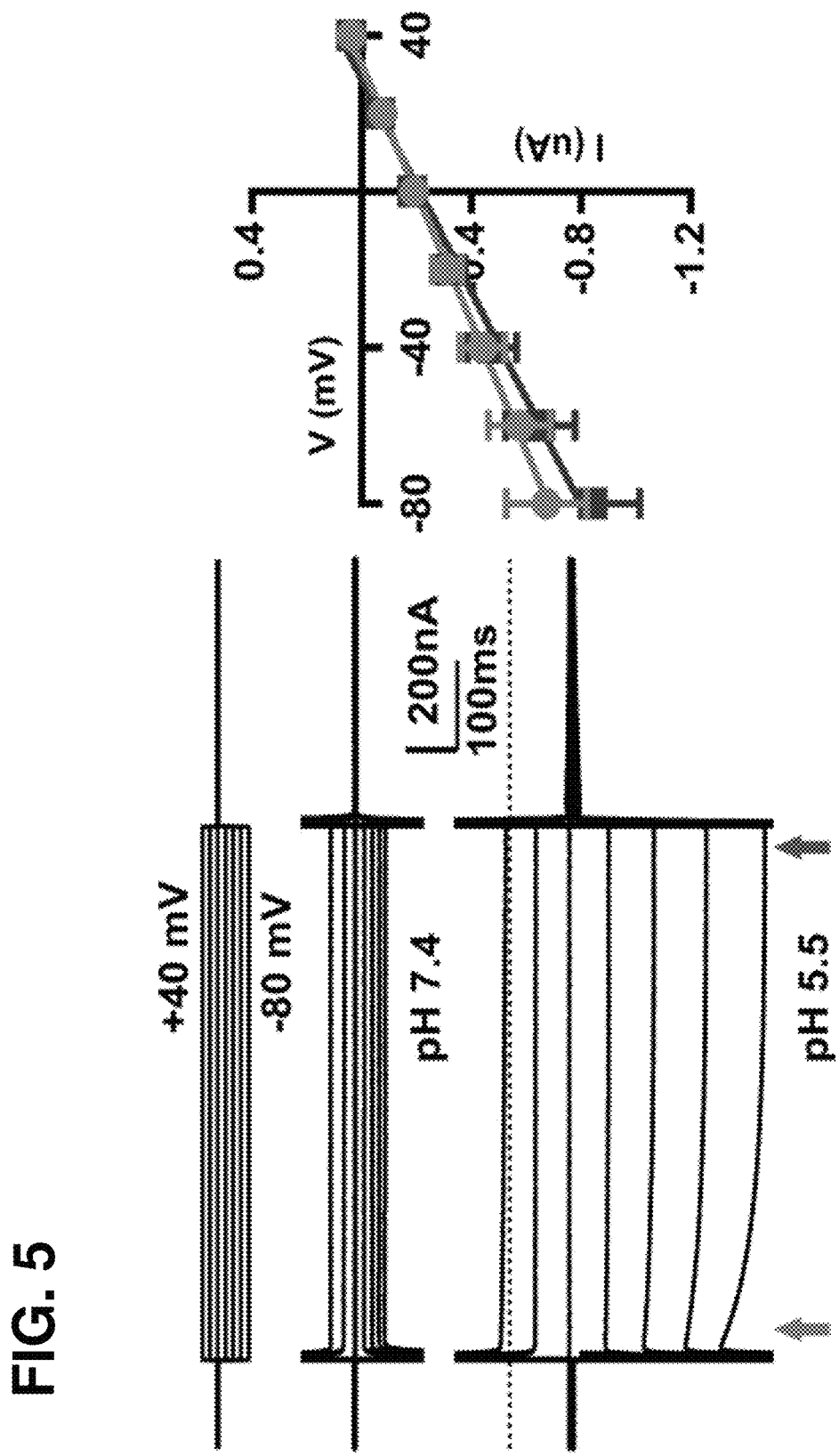
FIG. 5—Otop1 currents show only mild voltage-dependence.

Otop1 was tested to determine if it might be voltage-dependent. The response of Otop1 currents, evoked by pH 5.5 solution, to voltage steps between −80 to +40 mV (from a holding potential of 0 mV) was measured. The currents showed little evidence of a time-dependent change in amplitude, indicating that gating of Otop1 is not appreciably voltage-dependent over a range of physiologically relevant voltages (FIG. 5).

Together these data establish that Otop1 encodes a proton-selective ion channel with unique structural and biophysical properties.

Figure 3A:
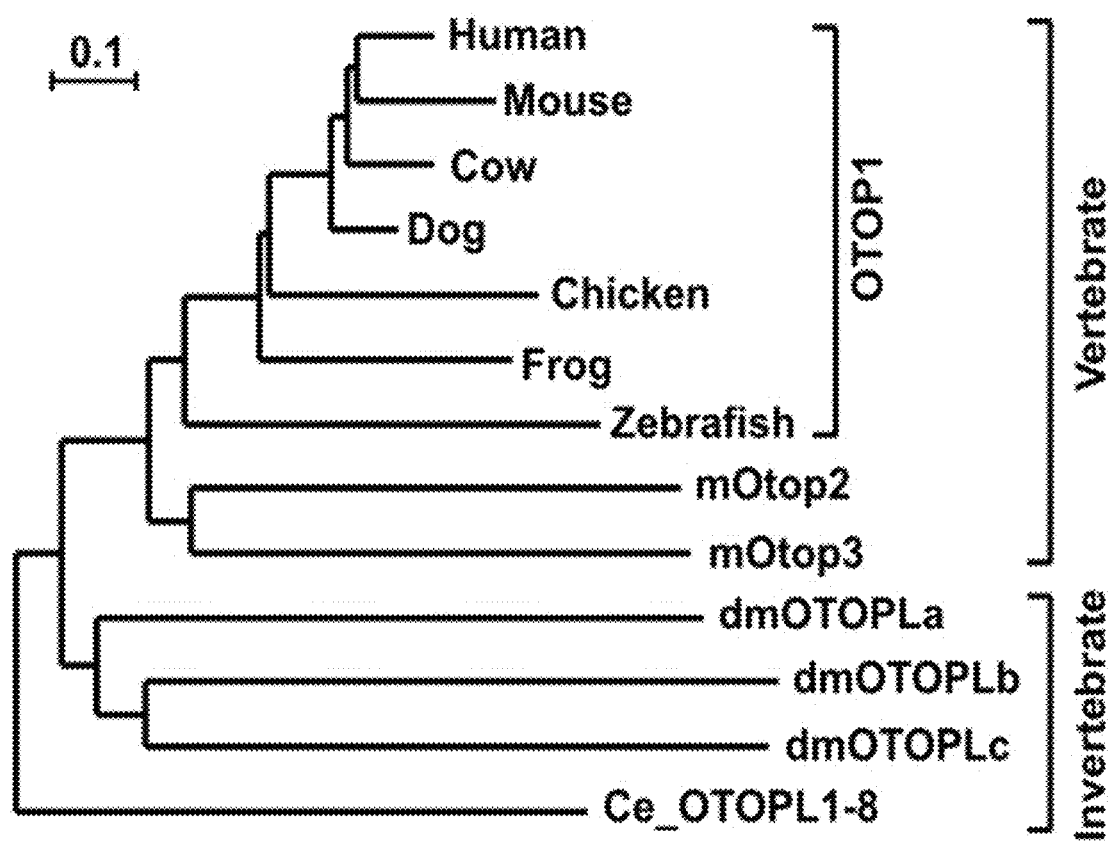
FIGS. 3A-3F—Otopetrins encode proton channels in diverse species.

Example 2—Otopetrins Constitute an Evolutionarily Conserved Family of Proton Channels Otopetrins are evolutionarily conserved from nematodes to humans[28,33] (FIG. 3a). To determine if this family functions generally as proton channels, we examined some of the most distantly related members.

Figure 3B:
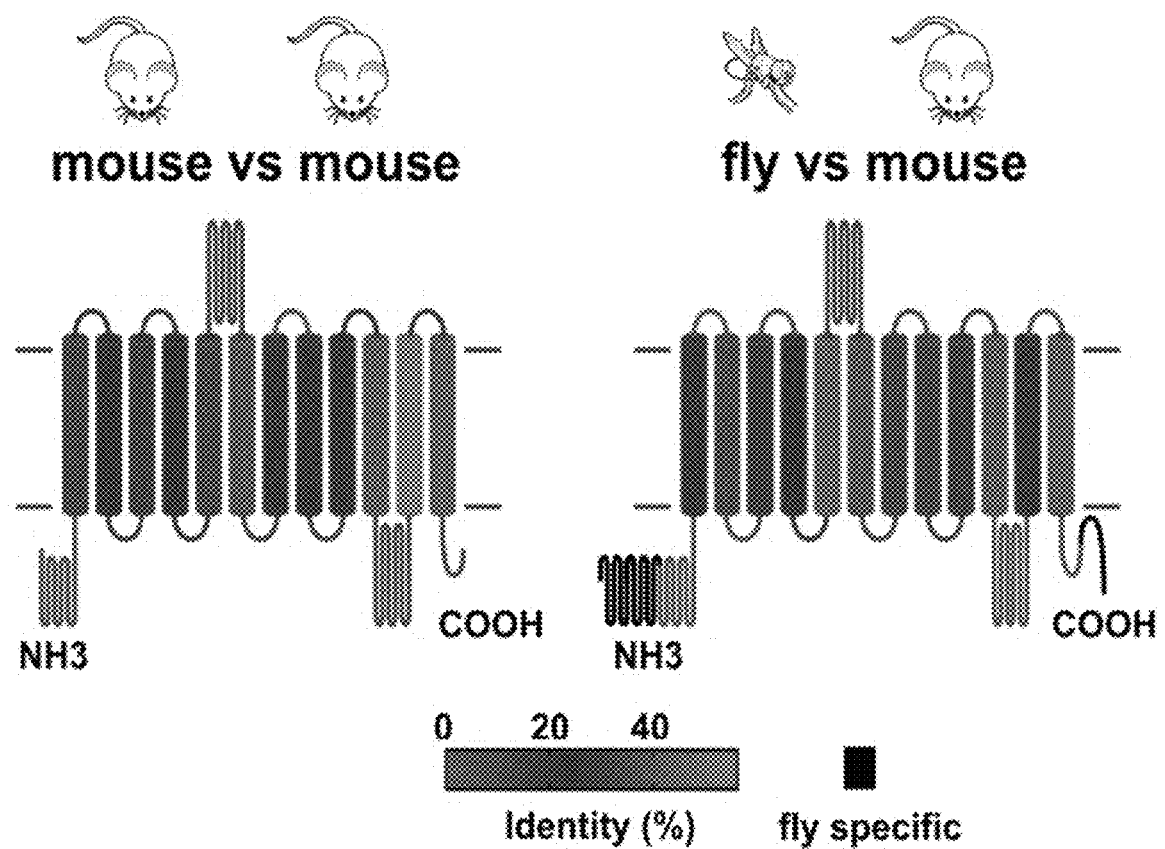
Figure 3C:
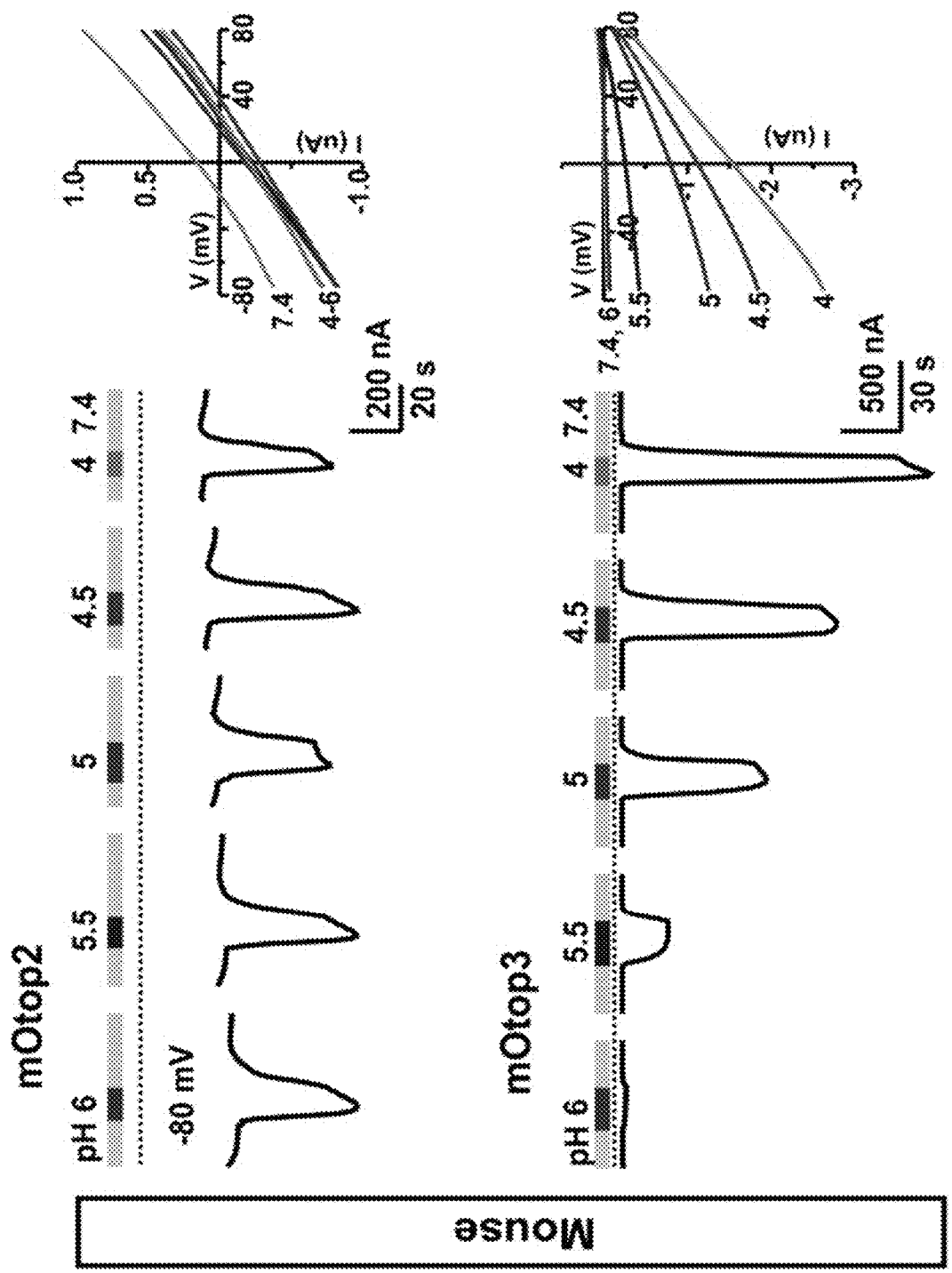
Figure 3D:
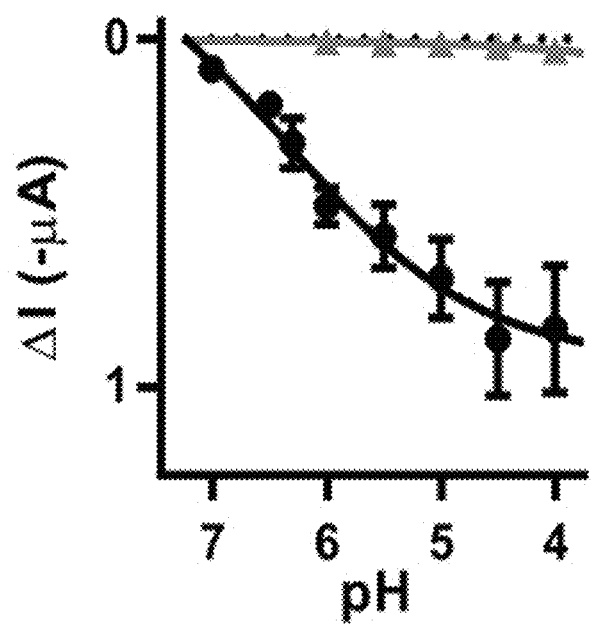
Figure 3D:
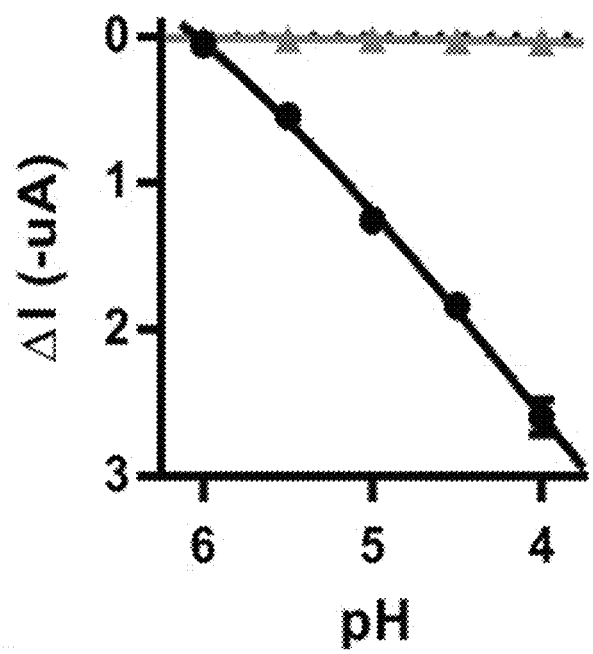
Figure 6A:
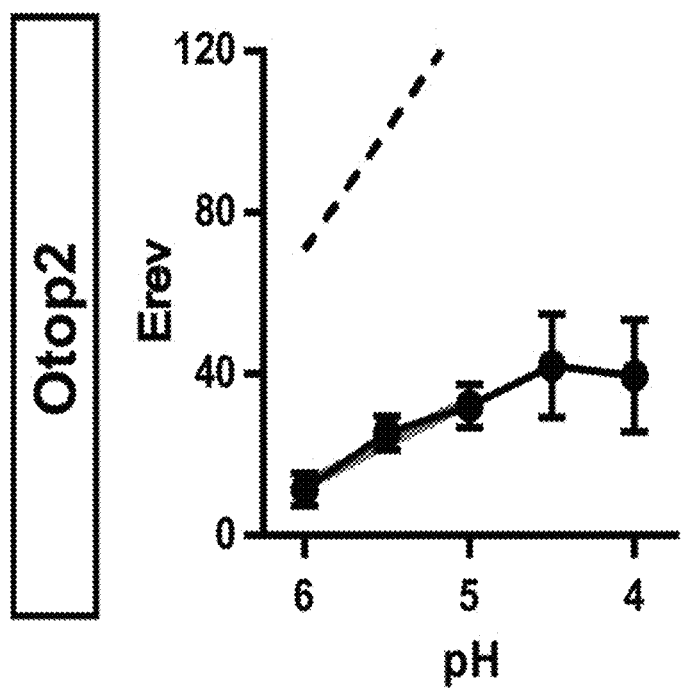
FIGS. 6A-6D—Otop2 and Otop3 form inwardly conducting proton channels.
Figure 6A:
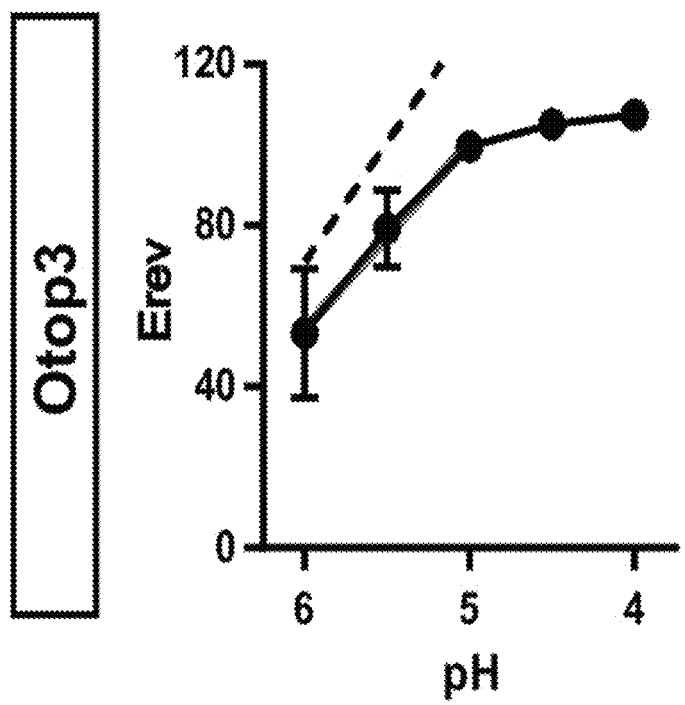
Figure 6B:
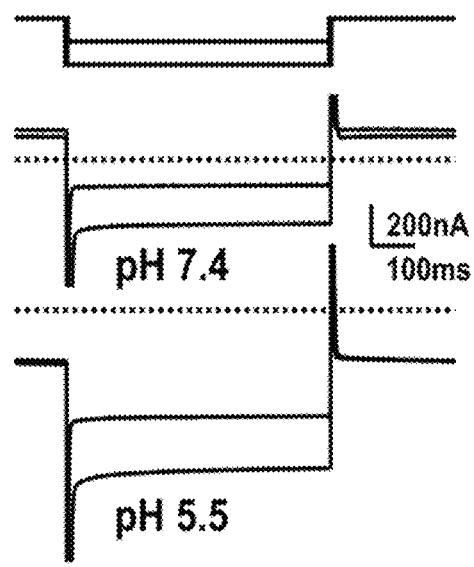
Figure 6B:
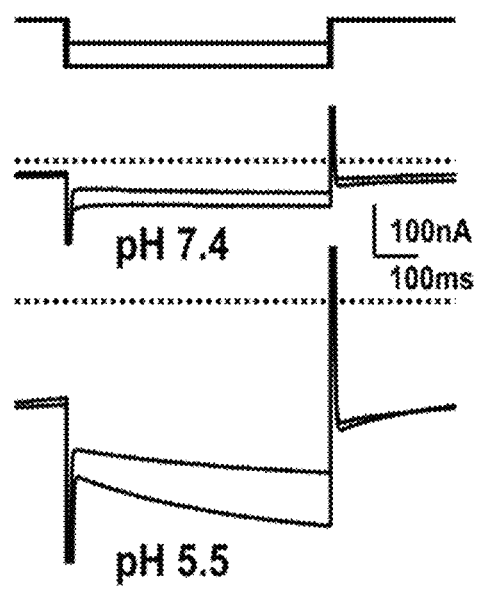
Figure 6C:
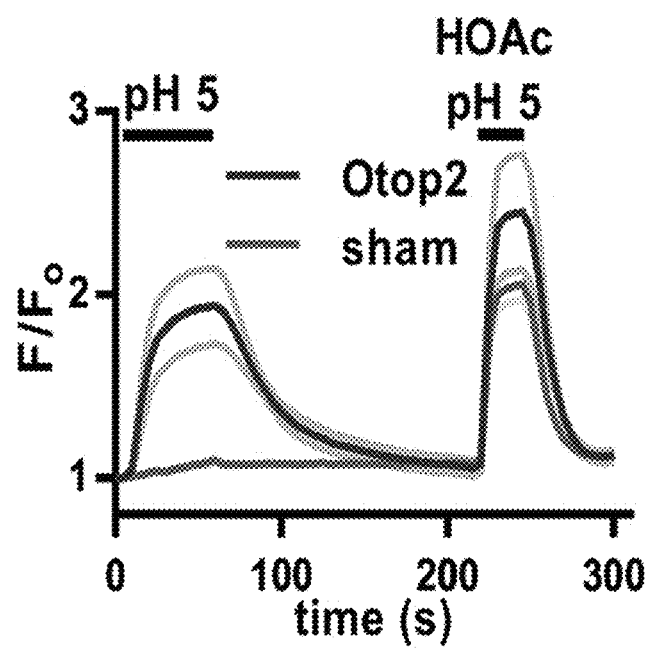
Figure 6C:
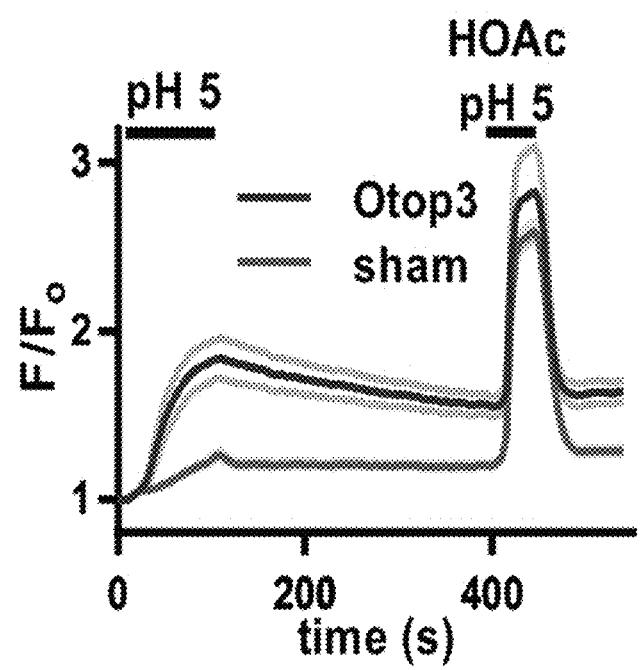
Figure 6D:
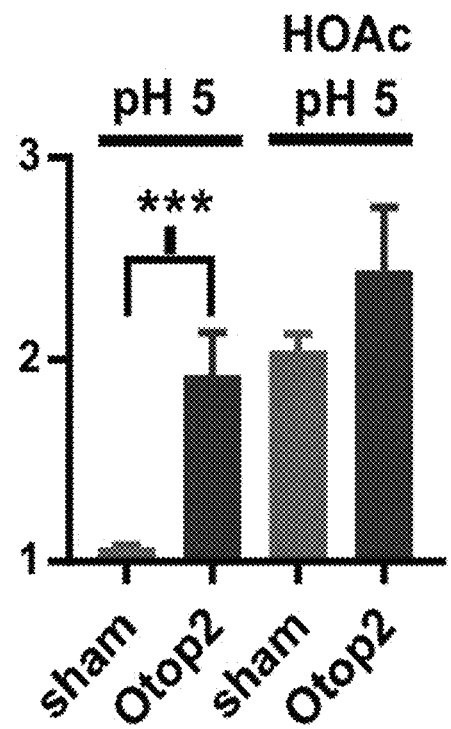
Figure 6D:
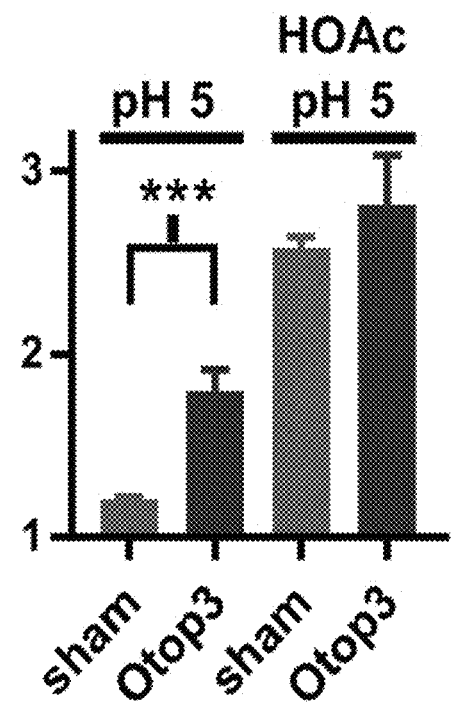
Figure 7A:
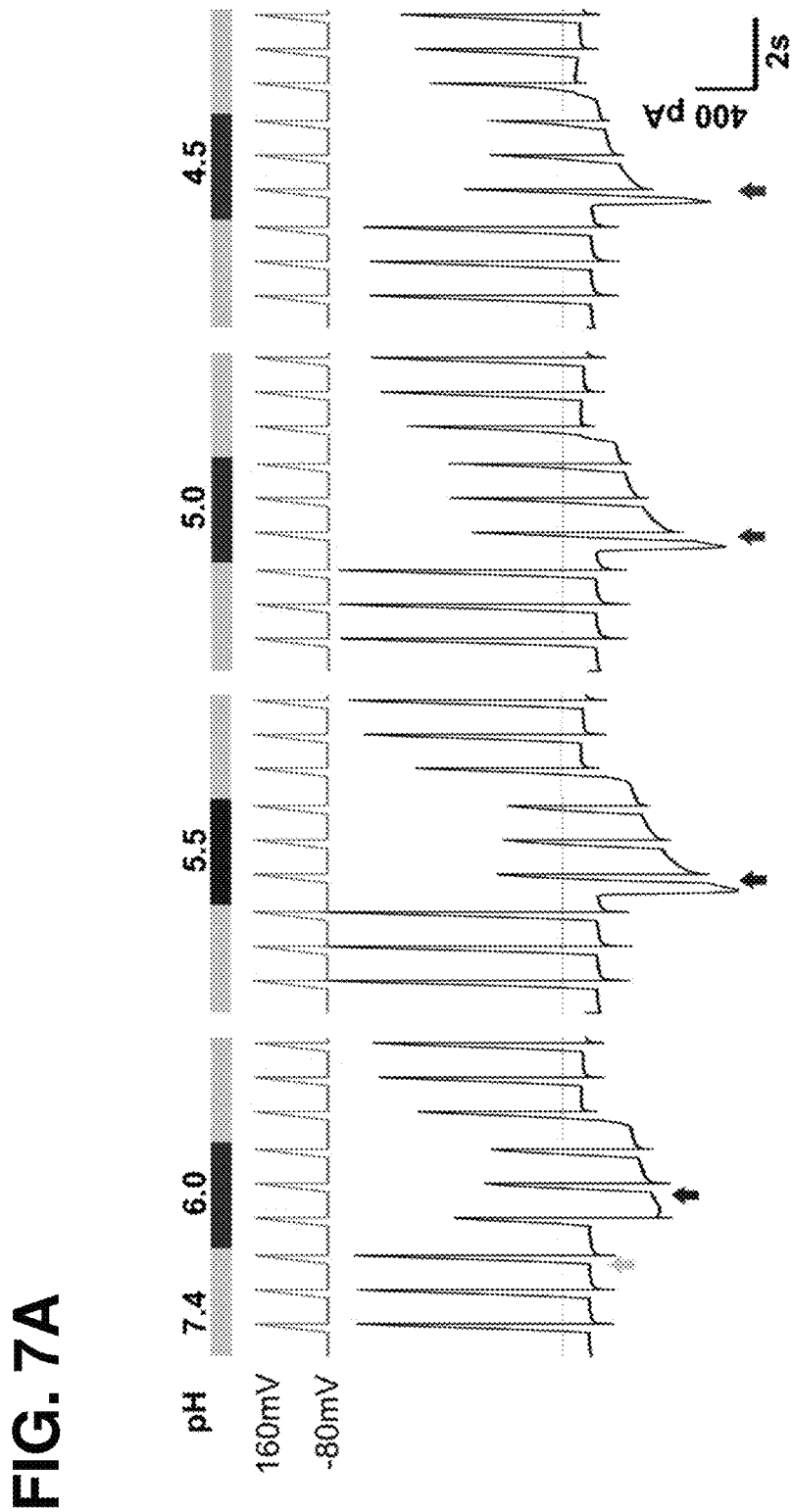
FIGS. 7A-7C—Biophysical properties of Otop2 in HEK-293 cells.
Figure 7B:
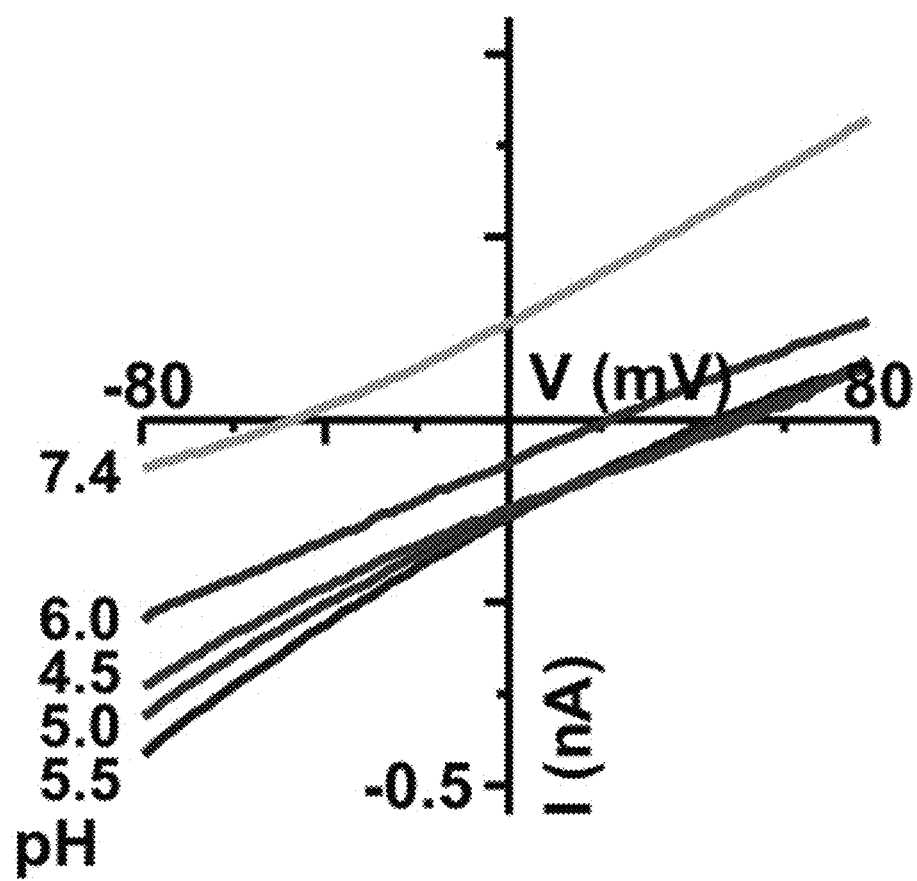
Figure 7C:
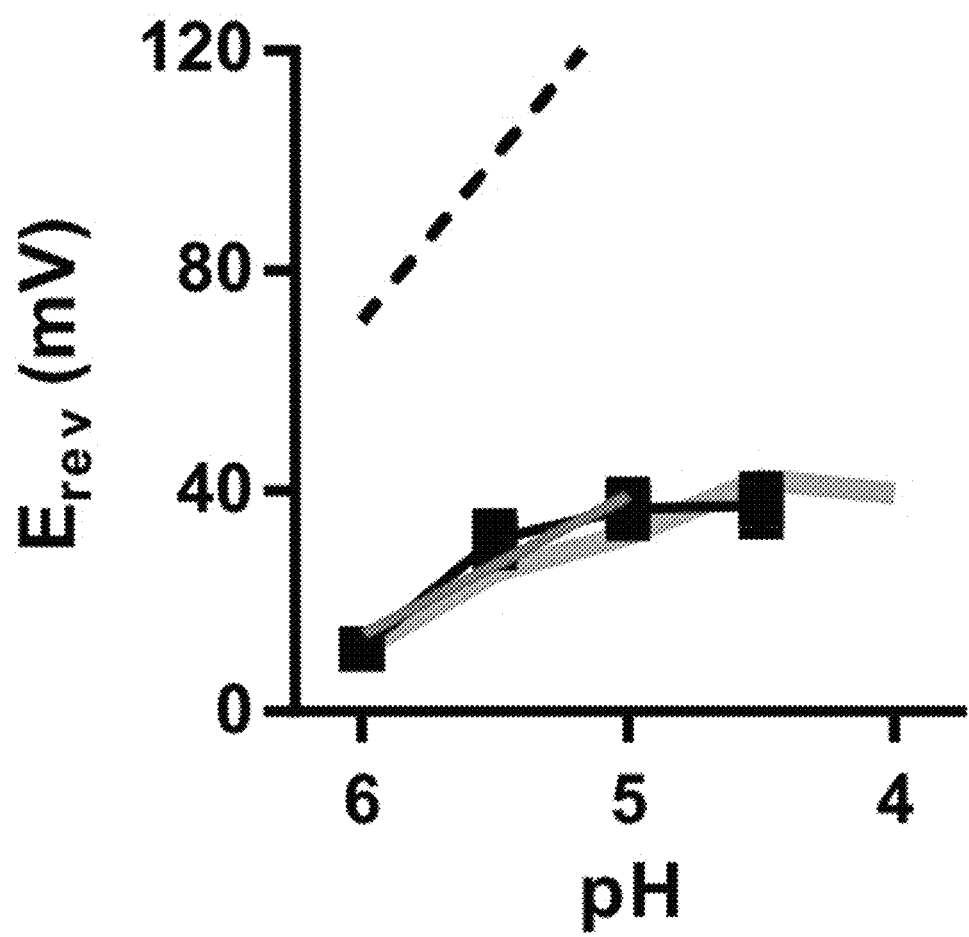

Otop1 has two murine homologs-mOtop2 and mOtop3[28] (FIG. 3A) which share 30%-34% amino acid identity with Otop1 (FIG. 3B). When expressed in *Xenopus* oocytes, both, Otop2 and Otop3 generated large currents upon lowering $pH_o$ in an NMDG-based solution (FIG. 3C). Otop3 showed evidence of high selectivity for $H^+$; the magnitude of Otop3 currents increased linearly as a function of $pH_o$ over the entire pH range tested (pH 4-6; FIGS. 3C and 3D) and $E_{rev}$ shifted 46.3 mV/log[$H^+$](FIG. 6A). In contrast, Otop2 currents behaved anomalously; they saturated at pH 5 (FIGS. 3C and 3D) and $E_{rev}$ shifted little over a range of pH 4-6 (FIG. 6A). These unexpected features of Otop2 are intrinsic to the channel protein as Otop2 currents measured in HEK-293 cells showed very similar properties (FIGS. 7A-7C). Both Otop2 and Otop3 currents showed little evidence of voltage-dependence, like Otop1 (FIG. 6A). When expressed in HEK-293 cells and measured with microfluorimetry, both Otop2 and Otop3 conducted protons into the cell cytosol in response to lowering $pH_o$ (FIGS. 6C and 6D). Interestingly, $pH_i$ in Otop3 transfected cells failed to recover following return to neutral $pH_o$, while Otop2 exhibited faster recovery as compared with Otop1, pointing to differences in $H^+$ conduction by the channels. Thus although Otop2 and Otop3 have distinct properties, both permeate protons.

Figure 3E:
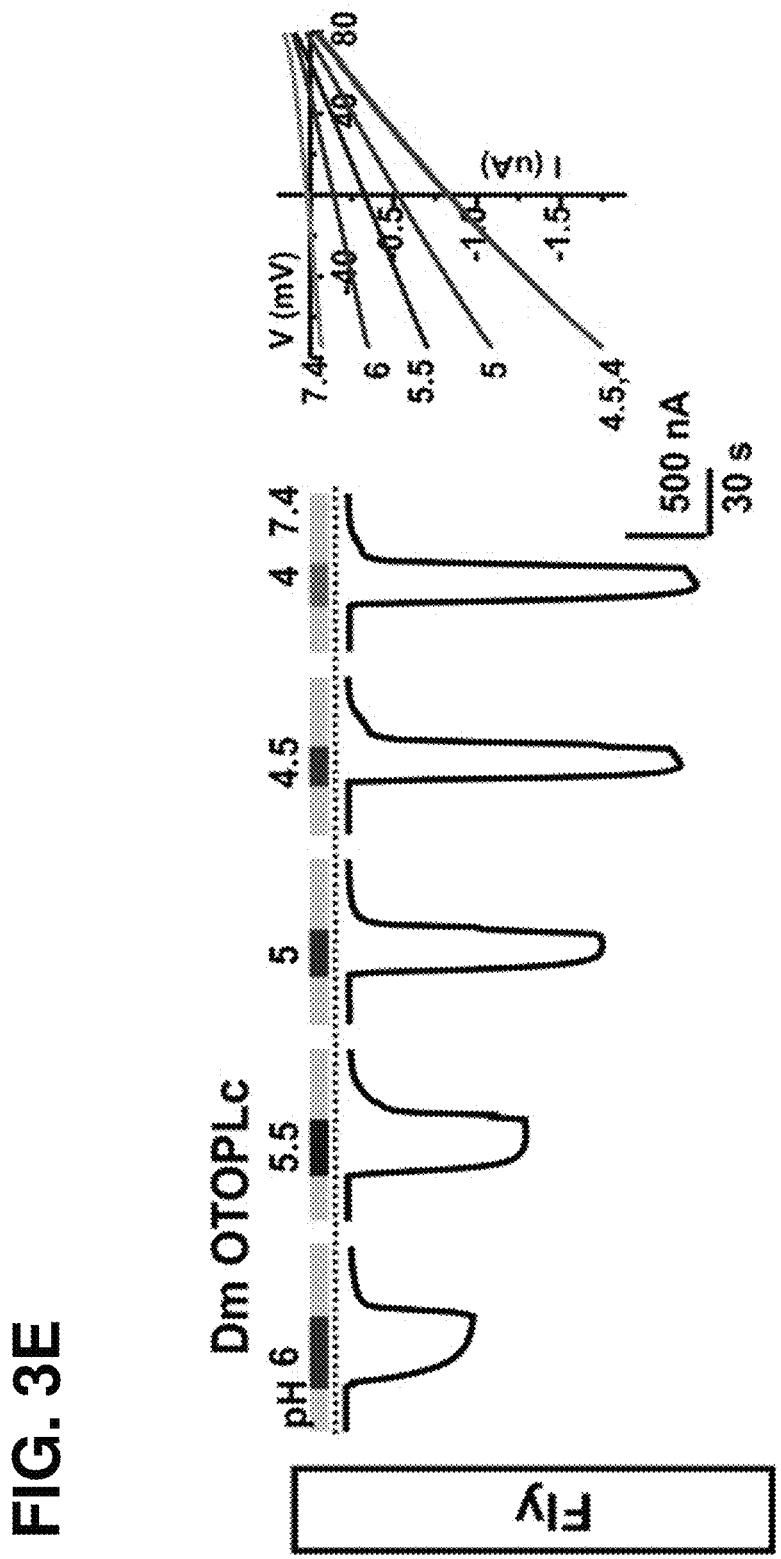
Figure 3F:
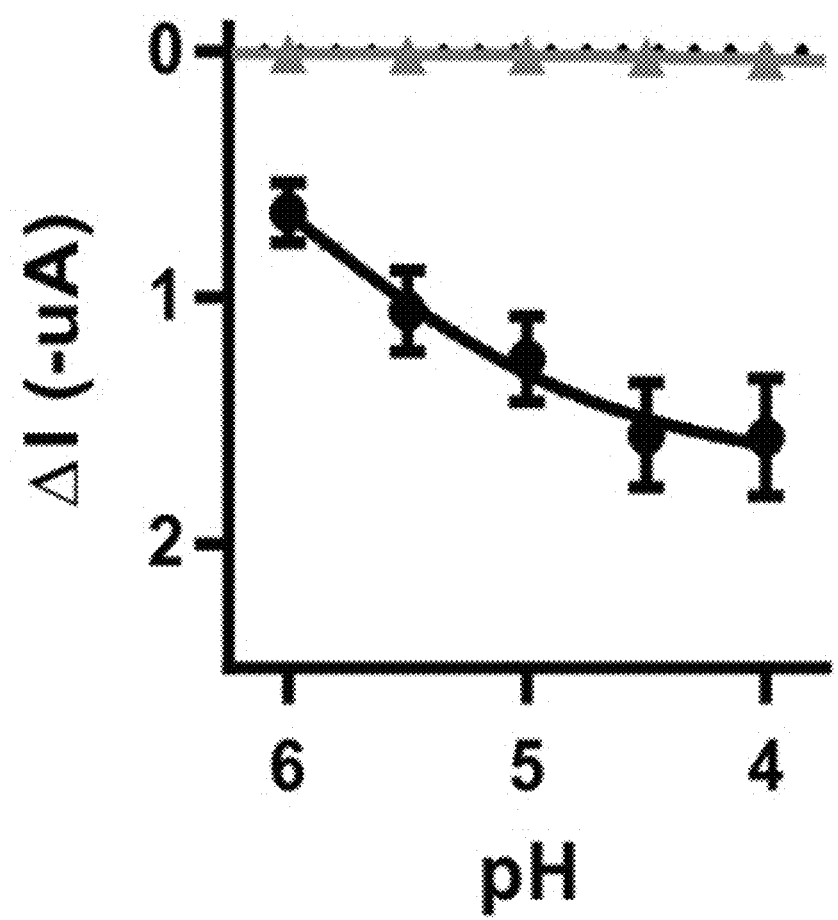
Figure 4A:
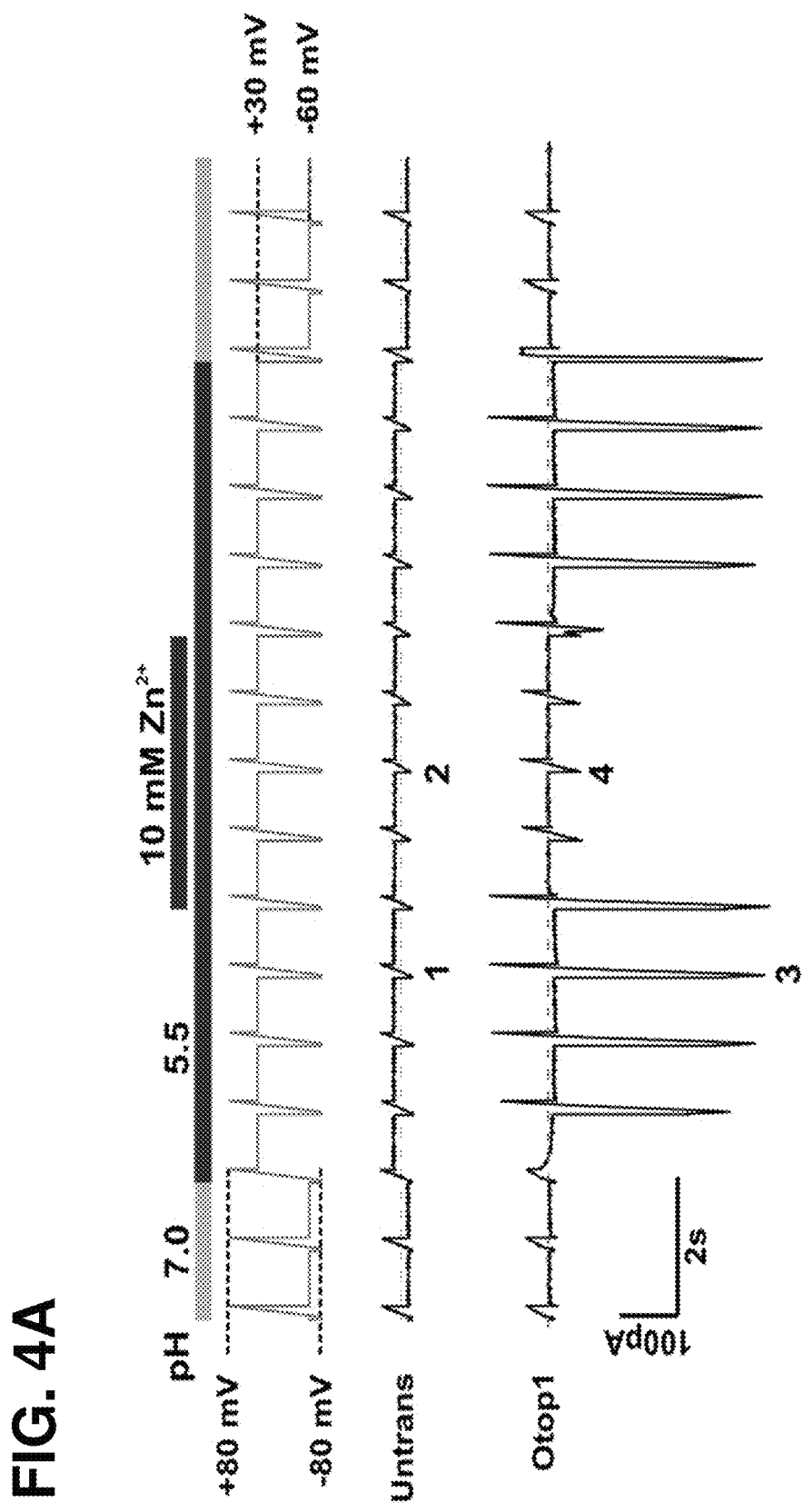
FIGS. 4A-4B—Measurement of $E_{rev}$ under conditions that stabilize the Otop1 currents.
Figure 4B:
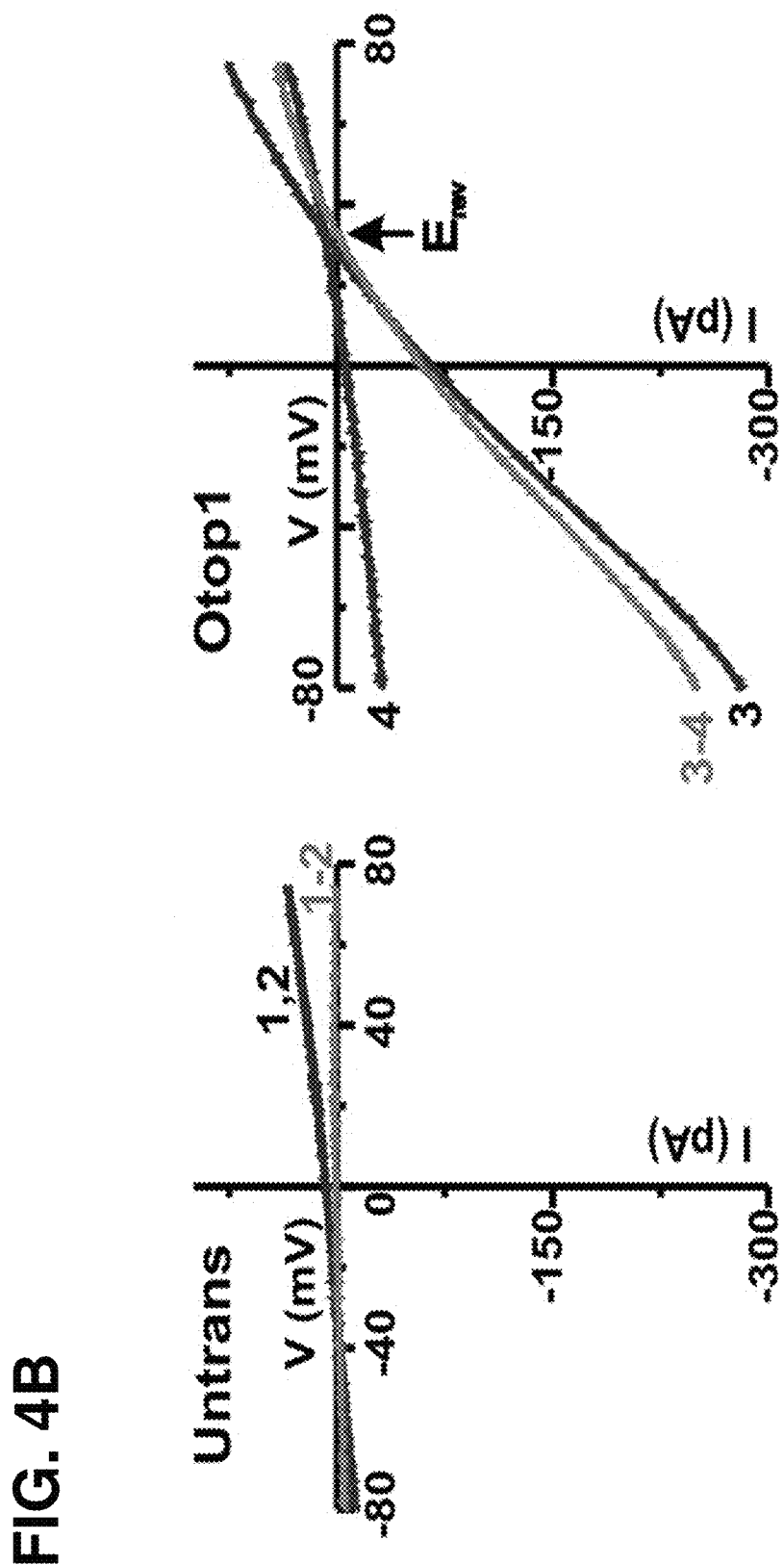

There are three genes in the *drosophila* genome related to mOtop1; they encode the predicted proteins dmOTOPLa, dmOTOPLb, and dmOTOPLc (FIG. 3A), none of which has previously been characterized. dmOTOPLc, a protein of 1576 amino acids, shows 14.1% amino acid identity with Otop1 over the region of homology and >30% amino acid identity in several of its transmembrane domains (FIG. 3B). When expressed in *Xenopus* oocytes dmOTOPLc produced large currents in response to lowering the extracellular pH (FIG. 3E). Like Otop1 and Otop3, dmOTOPLc currents increased as $pH_o$ was lowered and $E_{rev}$ shifted to more positive voltages, indicative of proton selectivity (FIG. 3E AND 3F). Interestingly, dmOTOPLc conducted relatively more current at pH6 than Otop1 or Otop3 and the relationship between the current amplitude and pH (FIG. 3F) was shallower; this may endow the channel with a broader dynamic range.

Together these data show that highly divergent and evolutionarily distant members of the Otopetrin family form channels with distinct functional properties but a common capacity to permeate protons.

Figure 8A:
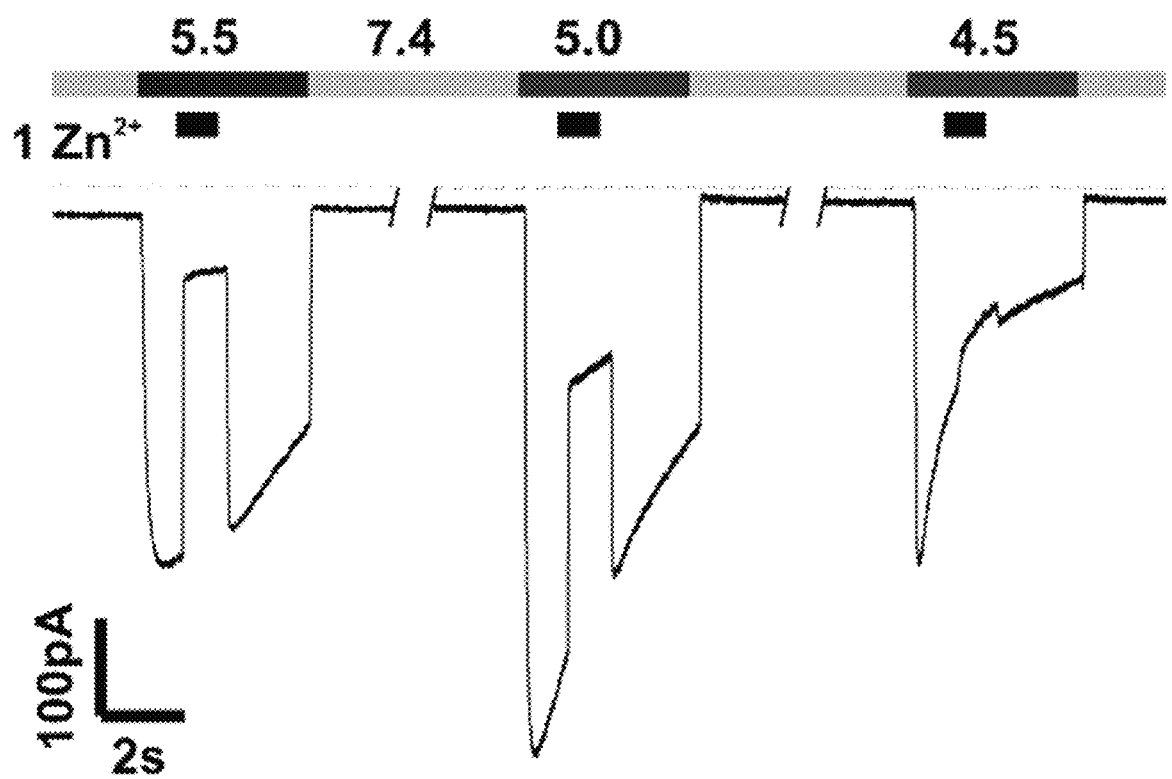
FIGS. 8A-8D—Human Otop1 forms a proton channel.
Figure 8B:
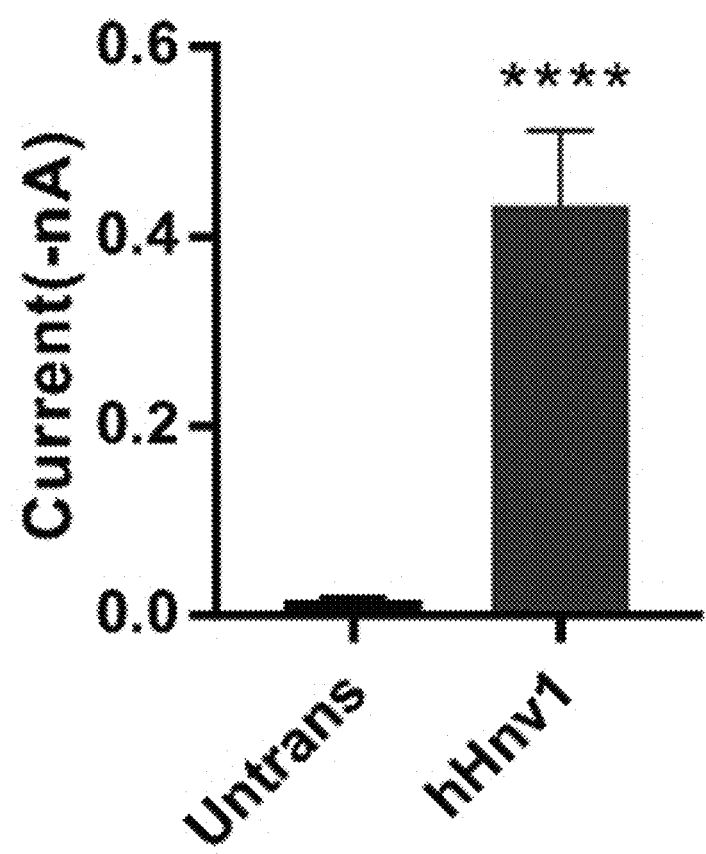
Figure 8C:
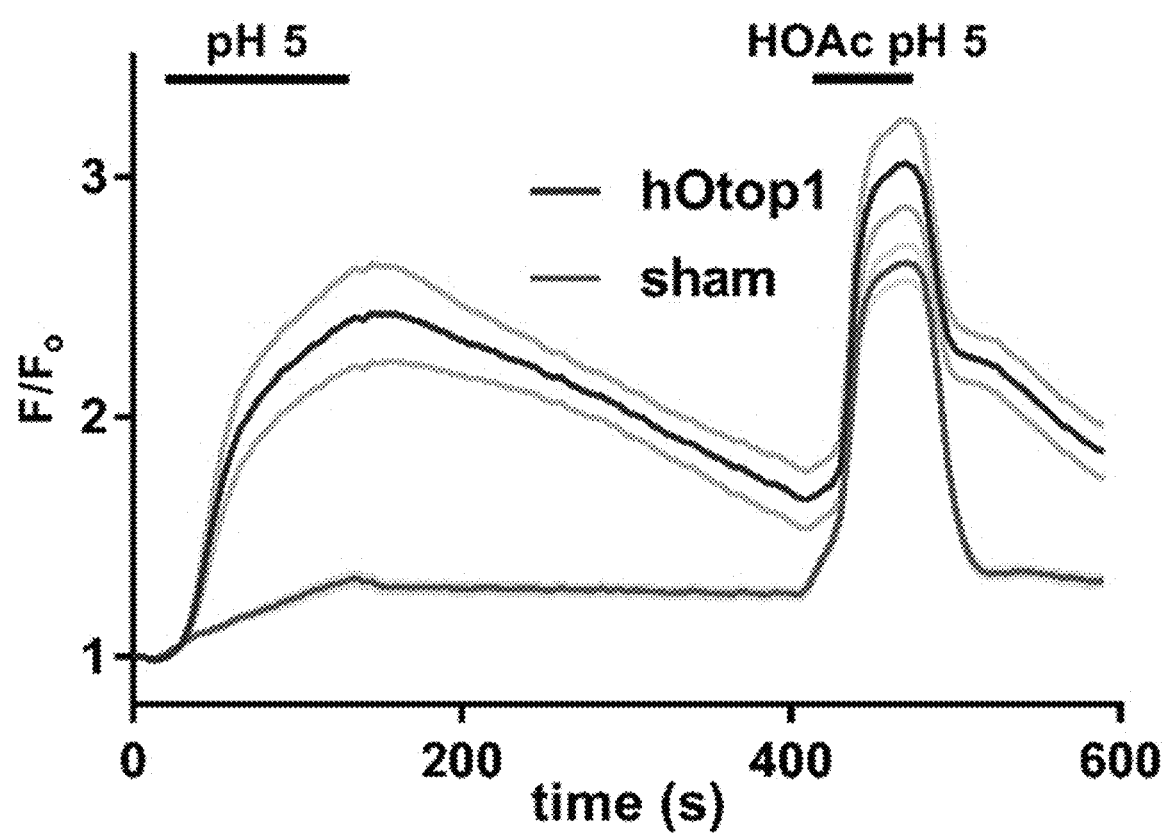
Figure 8D:
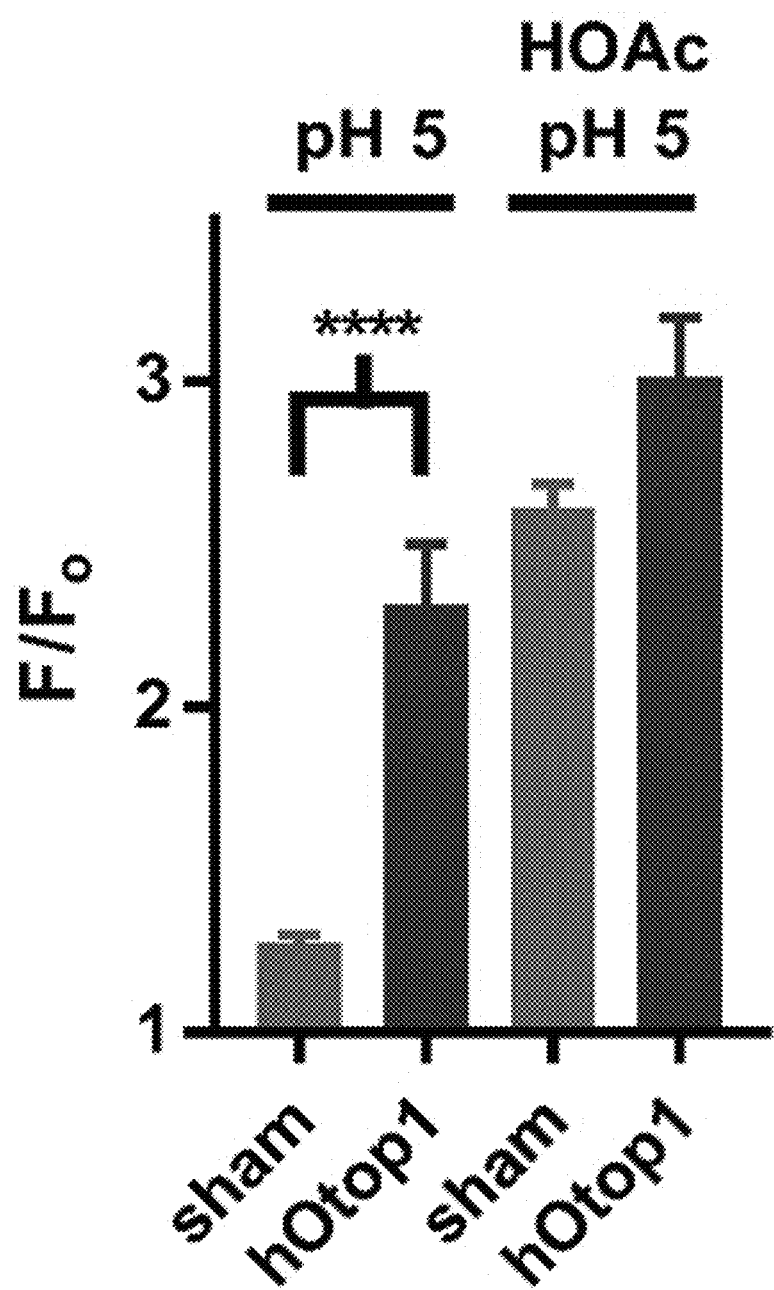

Example 3—Currents Through Otopetrin Channels Cause Changes in Intracellular pH and Calcium that can be Measured with Microfluorimetry To determine if proton influx through otopetrin channels, mOtop1, mOtop2, mOtop3 and hOtop1, could lead to a change in intracellular pH that could be detected with an intracellular pH-sensitive indicator dye, we transiently expressed each channel in HEK-293 cells. Indeed, when we imaged intracellular pH from mOtop1-transfected cells using the membrane permeant pH-sensitive dye pHrodo Red and lowered the extracellular pH from 7.4 to 5.0, we observed a large change in fluorescence indicative of a large change in intracellular pH (FIG. 1h). Similar results were observed (FIG. 8C and FIG. 8D) when monitoring changes in intracellular pH of HEK 293 cells transfected with hOtop1 using the pH indicator pHrodo red (mean+/−SEM), in response to a pH 5 solution. In both cases, a similar response was not observed in mock-transfected cells (FIG. 1H), indicating that the change in intracellular pH is a result of proton entry through Otop1 channels. FIGS. 7A-7C shows that HEK 293 cells transfected with Otop2 or Otop3 and loaded with pHrodo Red showed a large change in fluorescence upon lowering extracellular pH, indicating that both channels conduct protons into the cell cytosol in response to lowering extracellular pH (FIGS. 6C and 6D). Interestingly, the intracellular pH in Otop3 transfected cells failed to recover following return to neutral $pH_o$, while Otop2 exhibited faster recovery as compared with Otop1, pointing to differences in $H^+$ conduction by the channels.

Figure 10A:
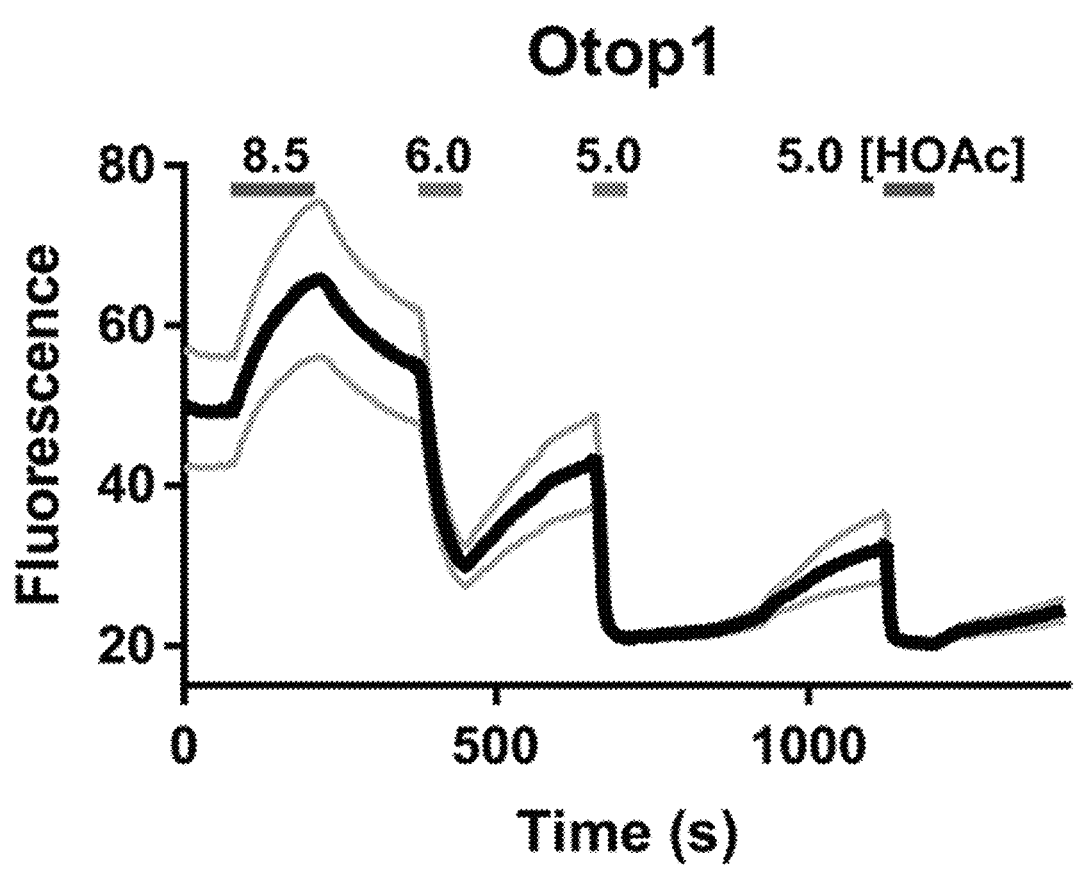
FIGS. 10A-10D—pHluorin imaging of different Otopetrins in response to various pH. HEK-293 cells were co-transfected with pHluorin and one of the indicated otopetrin polypeptides or control (FIG. 10A, transfected with pHluorin alone).
Figure 10B:
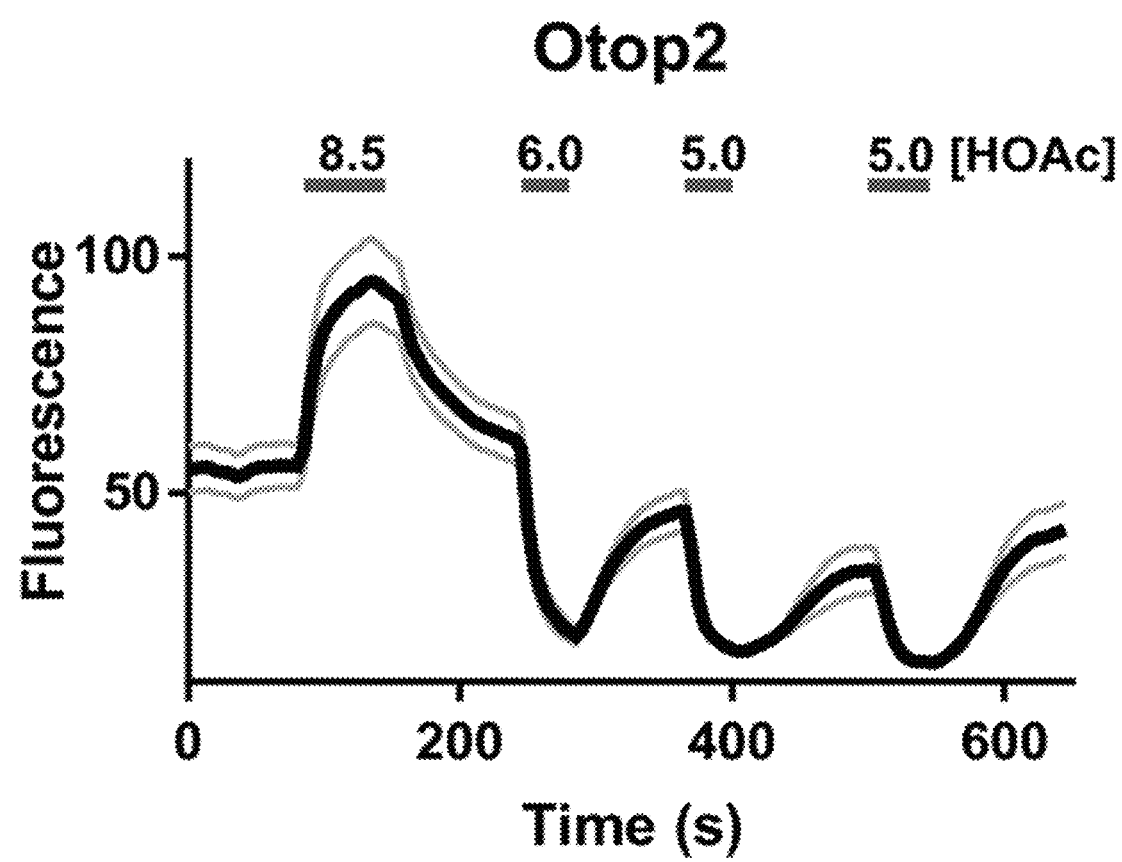
Figure 10C:
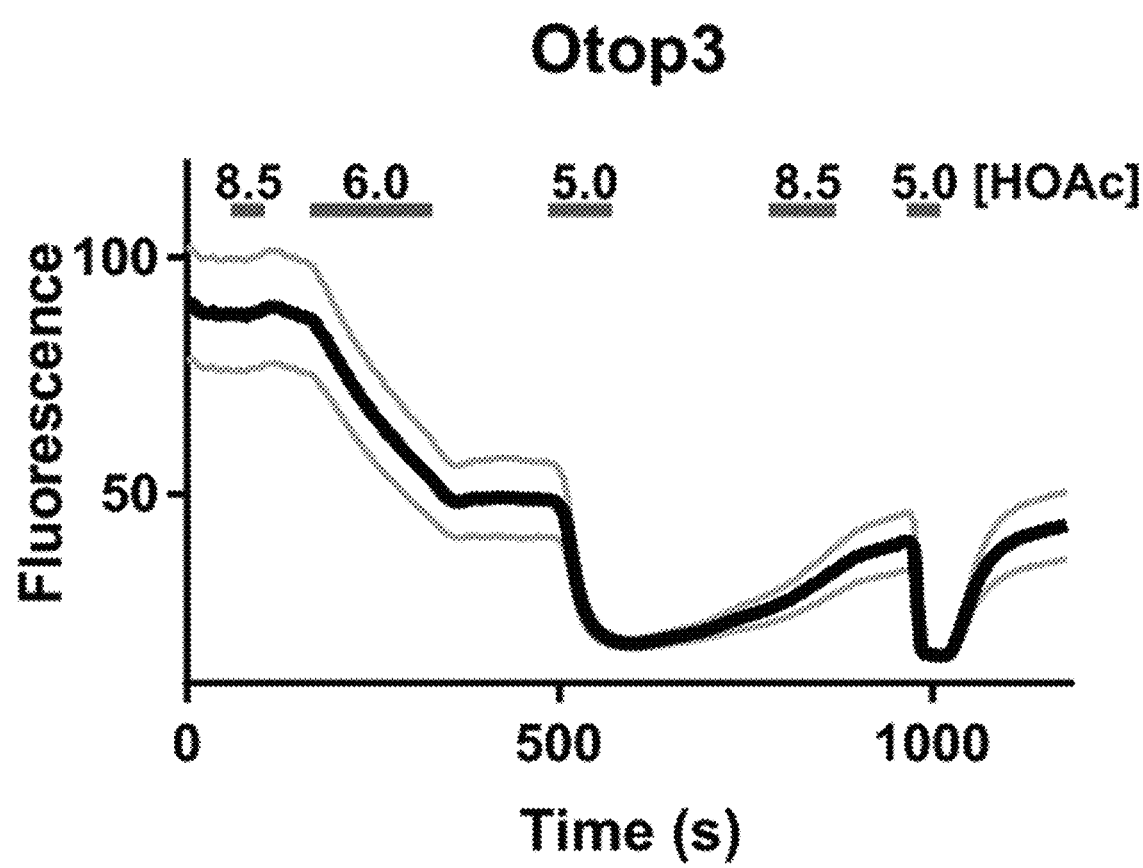
Figure 10D:
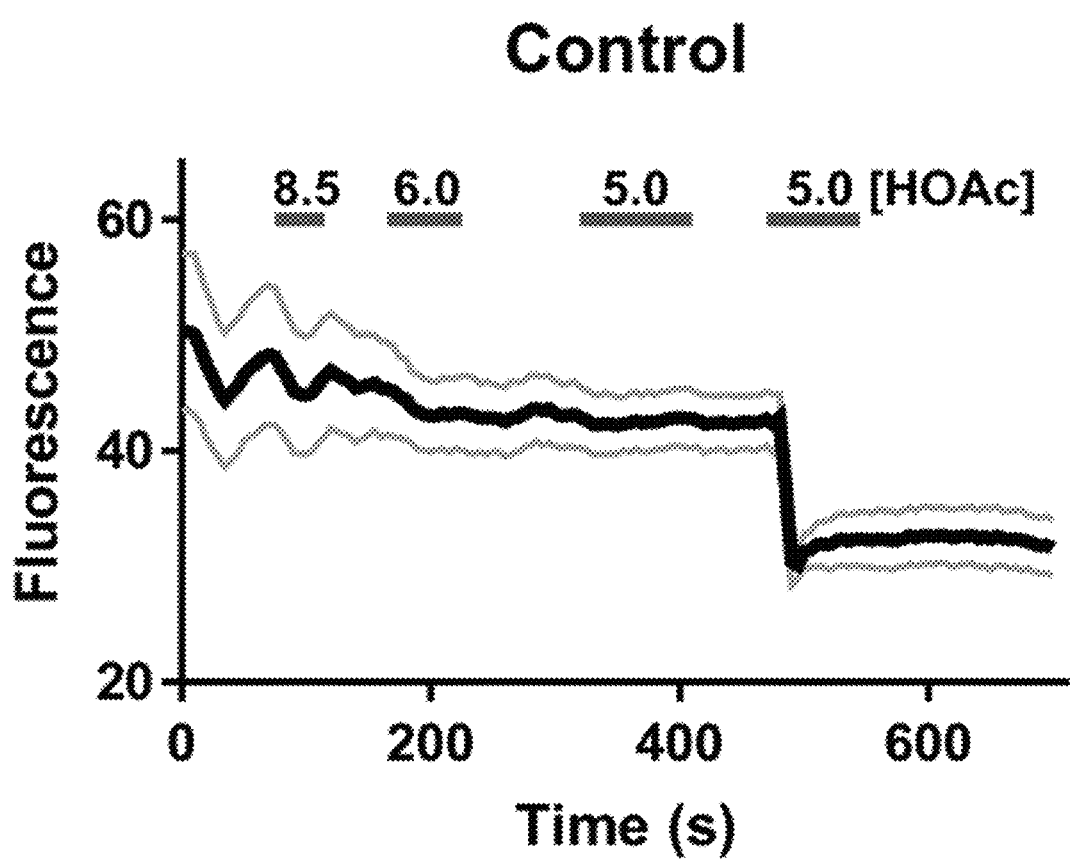

We also tested whether proton transport through Otop1 (FIG. 10A), Otop2 (FIG. 10B), and Otop3 (FIG. 10C) could be monitored with a genetically encoded pH indicator. For this we use pHluorin, which was co-transfected with each of the channels, or transfected alone (as a control). In HEK 293 cells transfected with Otop channels, large changes in fluorescent emission were detected from pHluorin when external pH was lowered (Otop1, Otop2 and Otop3) or external pH was raised (Otop 1 and Otop2). These responses were only observed in cells transfected with one of the three Otops and were not observed in untransfected cells.

Figure 9:
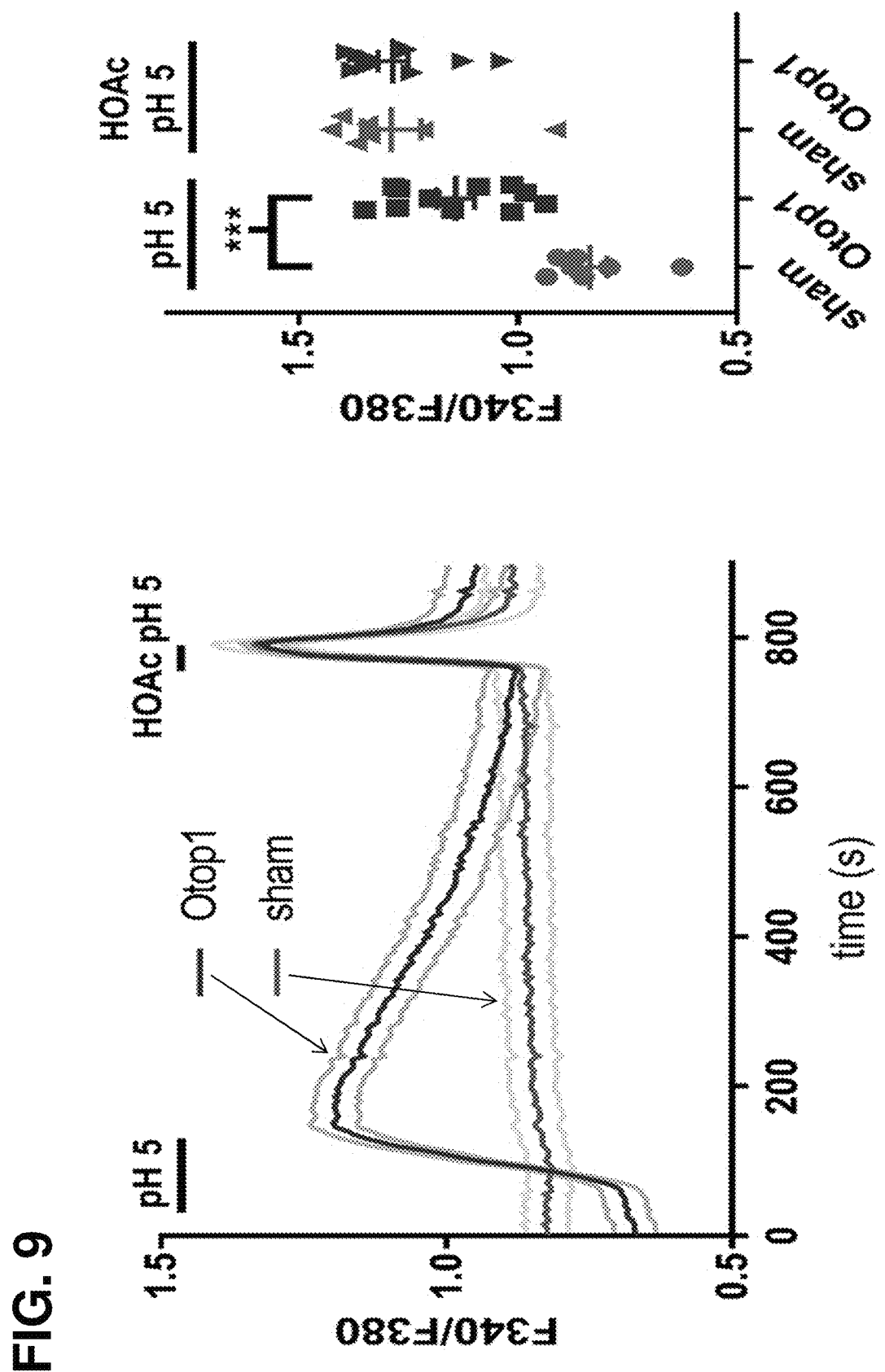
FIG. 9—Elevation of intracellular calcium in an Otop1-transfected HEK-293 cells in response to a change in extracellular pH.

Example 4. Elevation of Intracellular Calcium in an Otop1-Transfected HEK-293 Cells in Response to a Change in Extracellular pH We also tested whether entry of protons through Otop channels could cause a change in intracellular calcium that could be detected by micofluorometry. Transfected cells were loaded with the calcium indicator Fura2 AM and exposed to a change in extracellular pH from 7.4 to 5.0. FIG. 9 (left panel) shows that only the Otop1 transfected cells responded with an elevation of intracellular calcium (n=8 cells). The difference between Otop1 transfected and sham-transfected cells is significant (student's t-test. *** p<0.001). As a control, we showed that both transfected and untransfected cells responded to HOAc, pH 5, which penetrates cell membranes and causes intracellular acidification, thereby elevating intracellular calcium by liberating it from intracellular buffers.

Example 5—Material & Methods

Animals

All experimental procedures were approved by IACUC of University of Southern California. Mice in which expression of eGFP was driven by TRPM5 promoter[22,23] and YFP was driven by the Pkd211 promoter (Pkd211-YFP)[20] were bred to generate mice that were positive for both GFP and YFP (Trpm5-GFP/Pkd211-YFP).

For expression in HEK-293 cells, cDNAs were cloned into pcDNA3 vector with In-Fusion® HD Cloning Kit (Clontech). N-terminal YFP-tagged mOtop1 was generated by eliminating the start codon and subcloning Otop1 in frame to a 5' YFP in pcDNA3. All sequences were verified by Sanger sequencing (Genewiz). In vitro transcription was performed with T7 mMESSAGE mMACHINE kit (Thermo Fisher Scientific). The mRNA were treated with TURBO DNase (37° C. for 15 min), purified with RNA Clean & Concentrator kit (Zymo), and checked for the integrity and concentration with gel electrophoresis and Nanodrop (Thermo Scientific).

*Xenopus* Oocyte Electrophysiology

*Xenopus laevis* oocytes were provided by Ecocyte Bioscience. mRNA (0.2-20 ng, 50 nL) were injected into the oocytes with Nanoject II Auto-Nanoliter Injector (Drummond) and incubated in Standard Barth's solution (SBS, Ecocyte Bioscience) at 18° C. for 1-3 days before recording.

Two-electrode voltage clamp (TEVC) was performed as previously described[42]. The borosilicate glass pipette was pulled with P-97 Flaming/Brown type micropipette puller and its resistance was within the range of 0.5-5 MΩ. The current was measured with GeneClamp 500 amplifier (Axon). Solution exchange was executed by gravity driven perfusion. For most experiments, the membrane potential was held at −80 mV, and voltage ramps were applied every second from −80 mV to +80 mV (1V/s). The oocytes were incubated in the Nat-free extracellular solution with 100 μM DIDS for 2-3 min to inhibit $Ca^{2+}$-activated $Cl^-$ channels[43,44] before the application of acids. Significance was determined by ANOVA.

Oocyte Electrophysiology Solutions

*Xenopus* oocytes were incubated in ND96 solution containing (in mM): 100 NaCl, 2 KCl, 1.8 $CaCl_2$, 2 $MgCl_2$, 10 HEPES, pH adjusted to 7.4 with HCl. For measuring the current change in response to a change in $pH_o$, sodium-free solutions were used, containing 100 N-Methyl-D-glucamine (NMDG), 2 KCl, 1.8 $CaCl_2$, 2 $MgCl_2$, buffered with either 10 mM HEPES pH 6.5-7.4 or with 2-(N-morpholino)ethanesulfonic acid (MES, 10 mM) for pH 4-6. pH was adjusted with HCl. The following chemicals were added to the sodium-free solutions as indicated in figures: 100 μM 4,4'-Diisothiocyano-2,2'-stilbenedisulfonic acid (DIDS), 0.03-10 $ZnCl_2$, 100 μM Amantadine.

Transfection of HEK-293 Cells

Otop and GFP (5:1) were co-transfected into HEK-293 cells (CRL-1573, ATCC) using TransIT-LT1 Transfection Reagent (Mirus Bio Corporation, Madison, Wis.). Patch clamp recording and imaging experiments on GFP-positive cells were performed at room temperature ~24-48 h after transfection.

Patch Clamp Electrophysiology

Whole-cell patch clamp recording was performed as previously described[49]. In brief, recordings were made with an Axopatch 200A or Axopatch 200B amplifier, digitized with a Digidata 1322a 16-bit data acquisition system, acquired with pClamp 8.2, and analyzed with Clampfit 8.2 (Molecular Devices, Palo Alto, Calif.). Records were sampled at 5 kHz and filtered at 1 kHz. Patch pipettes with resistance of 2-4 MΩ were fabricated from borosilicate glass, and only recordings in which a gigaohm seal was achieved were used in the analysis. For most experiments, after the whole cell configuration was achieved, the membrane potential was held at −80 mV, or ramped from −80 mV to +80 mV (1V/s) once per second. For experiments to determine proton selectivity of Otop 1 the membrane potential was held at $E_H$ for the extracellular solution bathing the cell and ramped from −80 mV to +80 mV (1V/s) once per second. Solutions were changed using a linear array of microperfusion pipes (Warner Instruments, Hamden, Conn.).

Patch Clamp Electrophysiology Solutions

Tyrode's solution contained 145 mM NaCl, 5 mM KCl, 1 mM $MgCl_2$, 2 mM $CaCl_2$, 20 mM dextrose, 10 mM HEPES (pH 7.4 with NaOH). Pipette solutions contained 120 mM Cs-aspartate, 15 mM CsCl, 2 mM Mg-ATP, 5 mM EGTA, 2.4 mM $CaCl_2$ (100 nM free $Ca^{2+}$), and 10 mM HEPES (pH 7.3 with CsOH). For experiments in which $pH_o$ was varied (FIGS. 1D-1F), extracellular solutions contained 160 mM NMDG, 2 mM $CaCl_2$, and either 10 mM HEPES (for pH 7.4), 10 mM MES (for pH 6-5.5), or 10 mM HomoPIPES (for pH 5-4), pH adjusted with HCl. For ion substitution experiment (FIG. 2A), solutions contained 160 mM NMDG-Cl was replaced by equimolar concentrations of NaCl, LiCl, or CsCl and 200 μM amiloride was added to block endogenous ENaC channels. For high calcium solutions, 60 mM NMDG was replaced by 40 mM $CaCl_2$ to maintain consistent osmolality. In the experiments shown in FIG. 1D-1F, FIGS. 3F-3G, and FIG. 7, 100 μM DIDS was added to block endogenous $Cl^-$ currents[45]. DIDS was omitted in all other experiments.

For measurement of proton selectivity (FIG. 2B-2E), the pipette solution contained: 130 mM TMA-methane sulfonate, 5 mM TEA-Cl, 2 mM MgATP, 5 mM EGTA, 2.4 mM $CaCl_2$ and 80 mM MES titrated to (6.0) with ~15 mM TMA-OH and adjusted to 305 mOsm with $dH_2O$. NMDG based (Na-free) external solution contained: 130 mM NMDG-methane sulfonate, 2 mM $CaCl_2$, 100 mM HEPES (pH7.0-7.4), or 100 mM MES (pH5.5-6.5), or 100 mM HomoPIPES (pH4.5-5.25), pH adjusted with ~10-15 mM NMDG-OH and adjusted to 305 mOsm with $dH_2O$. Na-containing solution contained: 130 mM Na-methane sulfonate, 2 mM $CaCl_2$, 100 mM HEPES (pH7.0), or 100 mM MES (pH5.5), pH adjusted with NaOH. Where indicated, $ZnCl_2$ (10 mM, final concentration), NMDG-Cl (20 mM), NaCl (20 mM) or $MgCl_2$ (10 mM) were added to the Na-free or Na-containing solution and osmolarity was adjusted with $dH_2O$. The pH of each solution was measured before use and adjusted if necessary. Note that the measurements were limited in accuracy by small variations in pH on the order of +/−0.01 pH units or ~+/−3% change in $[H^+]$ at pH 5.5; this could cause small changes in current magnitude when measuring response in the presences of different ions such as those shown observed in FIG. 2A. Liquid junction potentials of 5 mV were measured between the pipette solution and the bath solution (Tyrode's) and were corrected posthoc. To minimize junction potentials between solutions delivered by sewer pipes and the bath solution, a 1 M KCl agar bridge was utilized and the bath solution was adjusted to contain a similar composition of ions as the sewer pipe in use[46]. Junction potentials of <2 mV were not corrected.

pH Imaging

HEK-293 cells co-transfected with Otop and GFP were mixed with HEK-293 cells transfected with CFP and plated on protamine coated coverslips at 37° C. After at least one hour, cells were loaded with the intracellular pH indicator pHrodo Red AM, using PowerLoad concentrate according to the manufacturer's instructions (Molecular Probes). Cells co-transfected with Otop and GFP were identified using a U-MNIBA2 GFP filter cube (Olympus) while "sham" transfected cells expressing CFP were identified using a U-N31044v2 CFP filter cube (Olympus)—or by absence of fluorescence. pH imaging optics and image acquisition were the same as previously described[23] [21]. pHrodo Red fluorescence intensity for each cell was measured in response to pH 5.0 solutions buffered with MES (150 mM NaCl, 10 mM MES, 2 mM $CaCl_2$) or with acetic acid (150 mM NaCl, 10 mM acetic acid, 2 mM $CaCl_2$). The fluorophore was excited with 560 nm light, and emission at 630 nm was detected by a Hamamatsu digital CCD camera attached to an Olympus IX71 microscope using a U-N31004 Texas Red/Cy3.5 filter cube (Chroma Technologies). The pHrodo Red fluorescence intensity of each cell was normalized to its baseline fluorescence in pH 7.4 solution (150 mM NaCl, 10 mM HEPES, 2 mM $CaCl_2$) before the first acid application.

Data Analysis and Statistics

All data are presented as mean±SEM. unless otherwise noted. Statistical analyses (ANOVA or student's t-test) were performed using Graphpad Prism (Graphpad Software Inc). Sample sizes in the present study are similar to those reported in the literature for similar studies. Representative data shown in the figures was in some cases decimated 10-fold before exporting into the graphics programs Origin (Microcal) and Coreldraw (Corel).

For FIGS. 3A-3F, the maximum-likelihood phylogenetic tree was created from the multi-sequence alignment of 13 otopetrin family proteins using Align-X (Invitrogen) and NJplot[48]. Accession numbers are as follows: Human, NP_819056; Cow, NP_001193713; Mouse, NP_766297; Dog, XP_545943; Chicken, XP_015141351; Frog, XP_012811170; Zebrafish, NP_942098; m_OTOP2, NP_766389; m_OTOP3, NP_081408; dm_OTOPLa, AAF46050; dm_OTOPLb, AAN10385; dm_OTOPLc, ACL82893; ce OTOPL1, CCD61337. See Hughes et al.[28] Transmembrane topology was predicted using the TMHMM server 2.0 (On the internet <URL:http://www.cbs.dtu.dk/services/TMHMM/> accessed Apr. 24, 2017).

Example 6—Elevation of Intracellular Calcium in an Otop1-Transfected HEK-293 Cells in Response to a Change in Extracellular pH Calcium Imaging was used to assay for intracellular calcium changes in HEK-293 cells co-transfected with Otop and GFP, and HEK-293 cells transfected with CFP, that were cultured on protamine coated coverslips at 37° C. (FIG. 9). After at least one hour, cells were loaded with the intracellular calcium indicator fura-2 AM, using PowerLoad concentrate according to the manufacturer's instructions (Molecular Probes). Cells co-transfected with Otop and GFP were identified using a U-MNIBA2 GFP filter cube (Olympus) while "sham" transfected cells expressed either CFP—identified using a U-N31044v2 CFP filter cube (Olympus)—or no fluorescence. Calcium imaging optics and image acquisition were the same as described (Chang et al., 2010). Fura-2 excitation ratios, for each cell was measured in response to pH 5.0 solutions buffered with MES (150 mM NaCl, 10 mM MES, 2 mM $CaCl_2$) or with Acetic acid (150 mM NaCl, 10 mM acetic acid, 2 mM $CaCl_2$.

Example 7—References

The following references are incorporated by reference in their entirety.
1. Hille, B. Ionic channels of excitable membranes (Sinauer Associates Inc., Sunderland, Mass., 2001).
2. Casey, J. R., Grinstein, S. & Orlowski, J. Sensors and regulators of intracellular pH. *Nat Rev Mol Cell Biol* 11, 50-61 (2010).
3. Decoursey, T. E. Voltage-gated proton channels and other proton transfer pathways. *Physiol Rev* 83, 475-579 (2003).
4. Pinto, L. H., Holsinger, L. J. & Lamb, R. A. Influenza virus M2 protein has ion channel activity. *Cell* 69, 517-28 (1992).
5. Mould, J. A. et al. Permeation and activation of the M2 ion channel of influenza A virus. *J Biol Chem* 275, 31038-50 (2000).
6. Takeda, M., Pekosz, A., Shuck, K., Pinto, L. H. & Lamb, R. A. Influenza a virus M2 ion channel activity is essential for efficient replication in tissue culture. *J Virol* 76, 1391-9 (2002).
7. Ramsey, I. S., Moran, M. M., Chong, J. A. & Clapham, D. E. A voltage-gated proton-selective channel lacking the pore domain. *Nature* 440, 1213-6 (2006).
8. Sasaki, M., Takagi, M. & Okamura, Y. A voltage sensor-domain protein is a voltage-gated proton channel. *Science* 312, 589-92 (2006).
9. Thomas, R. C. & Meech, R. W. Hydrogen ion currents and intracellular pH in depolarized voltage-clamped snail neurones. *Nature* 299, 826-8 (1982).
10. Byerly, L., Meech, R. & Moody, W., Jr. Rapidly activating hydrogen ion currents in perfused neurones of the snail, Lymnaea stagnalis. *J Physiol* 351, 199-216 (1984).
11. DeCoursey, T. E. Hydrogen ion currents in rat alveolar epithelial cells. *Biophys J* 60, 1243-53 (1991).
12. Capasso, M., DeCoursey, T. E. & Dyer, M. J. pH regulation and beyond: unanticipated functions for the voltage-gated proton channel, HVCN1. *Trends Cell Biol* 21, 20-8 (2013).
13. Morgan, D. et al. Voltage-gated proton channels maintain pH in human neutrophils during phagocytosis. *Proc Natl Acad Sci USA* 106, 18022-7 (2009).
14. Lishko, P. V., Botchkina, I. L., Fedorenko, A. & Kirichok, Y. Acid extrusion from human spermatozoa is mediated by flagellar voltage-gated proton channel. *Cell* 140, 327-37 (2010).
15. Wu, L. J. et al. The voltage-gated proton channel Hv1 enhances brain damage from ischemic stroke. *Nat Neurosci* 15, 565-73 (2012).
16. DeCoursey, T. E. Voltage-gated proton channels: molecular biology, physiology, and pathophysiology of the H(V) family. *Physiol Rev* 93, 599-652 (2013).
17. Ramsey, I. S., Ruchti, E., Kaczmarek, J. S. & Clapham, D. E. Hv1 proton channels are required for high-level NADPH oxidase-dependent superoxide production during the phagocyte respiratory burst. *Proc Natl Acad Sci USA* 106, 7642-7 (2009).
18. DeCoursey, T. E. & Hosler, J. Philosophy of voltage-gated proton channels. *J R Soc Interface* 11, 20130799 (2014).
19. Smith, S. M. et al. Voltage-gated proton channel in a dinoflagellate. *Proc Natl Acad Sci USA* 108, 18162-7 (2011).
20. Chang, R. B., Waters, H. & Liman, E. R. A proton current drives action potentials in genetically identified sour taste cells. *Proc Natl Acad Sci USA* 107, 22320-5 (2010).
21. Bushman, J. D., Ye, W. & Liman, E. R. A proton current associated with sour taste: distribution and functional properties. *FASEB J* 29, 3014-26 (2015).
22. Clapp, T. R., Medler, K. F., Damak, S., Margolskee, R. F. & Kinnamon, S. C. Mouse taste cells with G protein-coupled taste receptors lack voltage-gated calcium channels and SNAP-25. *BMC Biol* 4, 7 (2006).
23. Zhang, Z., Zhao, Z., Margolskee, R. & Liman, E. The transduction channel TRPM5 is gated by intracellular calcium in taste cells. *J Neurosci* 27, 5777-86 (2007).
24. Tang, F. et al. RNA-Seq analysis to capture the transcriptome landscape of a single cell. *Nat Protoc* 5, 516-35 (2010).
25. Zhou, T., Chien, M. S., Kaleem, S. & Matsunami, H. Single cell transcriptome analysis of mouse carotid body glomus cells. *J Physiol* 594, 4225-51 (2016).
26. Chaudhari, N. & Roper, S. D. The cell biology of taste. *J Cell Biol* 190, 285-96 (2010).
27. Picelli, S. et al. Full-length RNA-seq from single cells using Smart-seq2. *Nat Protoc* 9, 171-81 (2014).
28. Hughes, I. et al. Identification of the Otopetrin Domain, a conserved domain in vertebrate otopetrins and invertebrate otopetrin-like family members. *BMC Evol Biol* 8, 41 (2008).

29. Kim, E. et al. Regulation of cellular calcium in vestibular supporting cells by otopetrin 1. *J Neurophysiol* 104, 3439-50 (2010).
30. Chizhmakov, I. V. et al. Selective proton permeability and pH regulation of the influenza virus M2 channel expressed in mouse erythroleukaemia cells. *J Physiol* 494 (Pt 2), 329-36 (1996).
31. Cherny, V. V. & DeCoursey, T. E. pH-dependent inhibition of voltage-gated H(+) currents in rat alveolar epithelial cells by Zn(2+) and other divalent cations. *J Gen Physiol* 114, 819-38 (1999).
32. Takeshita, K. et al. X-ray crystal structure of voltage-gated proton channel. *Nat Struct Mol Biol* 21, 352-7 (2014).
33. Hurle, B. et al. Non-syndromic vestibular disorder with otoconial agenesis in tilted/mergulhador mice caused by mutations in otopetrin 1. *Hum Mol Genet* 12, 777-89 (2003).
34. Kim, E. et al. Missense mutations in Otopetrin 1 affect subcellular localization and inhibition of purinergic signaling in vestibular supporting cells. *Mol Cell Neurosci* 46, 655-61 (2011).
35. Wu, C. et al. BioGPS: an extensible and customizable portal for querying and organizing gene annotation resources. *Genome Biol* 10, R130 (2009).
36. Wang, G. X. et al. Otopetrin 1 protects mice from obesity-associated metabolic dysfunction through attenuating adipose tissue inflammation. *Diabetes* 63, 1340-52 (2014).
37. Cichy, A. et al. Extracellular pH regulates excitability of vomeronasal sensory neurons. *J Neurosci* 35, 4025-39 (2015).
38. Wang, T. M., Holzhausen, L. C. & Kramer, R. H. Imaging an optogenetic pH sensor reveals that protons mediate lateral inhibition in the retina. *Nat Neurosci* 17, 262-8 (2014).
39. Walther, L. E., Blodow, A., Buder, J. & Kniep, R. Principles of calcite dissolution in human and artificial otoconia. *PLoS One* 9, e102516 (2014).
40. Lundberg, Y. W., Xu, Y., Thiessen, K. D. & Kramer, K. L. Mechanisms of otoconia and otolith development. *Dev Dyn* 244, 239-53 (2015).
41. Graze, R. M. et al. Allelic imbalance in *Drosophila* hybrid heads: exons, isoforms, and evolution. *Mol Biol Evol* 29, 1521-32 (2012).
42. Liman, E. R., Tytgat, J. & Hess, P. Subunit stoichiometry of a mammalian K+ channel determined by construction of multimeric cDNAs. *Neuron* 9, 861-71 (1992).
43. Faria, D. et al. The calcium-activated chloride channel Anoctamin 1 contributes to the regulation of renal function. *Kidney Int* 85, 1369-81 (2014).
44. Schroeder, B. C., Cheng, T., Jan, Y. N. & Jan, L. Y. Expression cloning of TMEM16A as a calcium-activated chloride channel subunit. *Cell* 134, 1019-29 (2008).
45. Zhu, G., Zhang, Y., Xu, H. & Jiang, C. Identification of endogenous outward currents in the human embryonic kidney (HEK 293) cell line. *J Neurosci Methods* 81, 73-83 (1998).
46. Neher, E. Correction for liquid junction potentials in patch clamp experiments. *Methods Enzymol* 207, 123-31 (1992).
47. Ye, W. et al. The K+ channel KIR2.1 functions in tandem with proton influx to mediate sour taste transduction. *Proc Nod Acad Sci USA* 113, E229-38 (2016).
48. Perriere, G. & Gouy, M. WWW-query: an on-line retrieval system for biological sequence banks. *Biochimie* 78, 364-9 (1996).
49. Wang, Y. Y., Chang, R. B., Waters, H. N., McKemy, D. D. & Liman, E. R. The nociceptor ion channel AN OTOPETRIN POLYPEPTIDE is potentiated and inactivated by permeating calcium ions. *J Biol Chem* 283, 32691-703 (2008).

Example 8—Otopetrin Sequences

```
Human-OTOP1 (SEQ ID NO: 1):
MLEGLGSPASPRAAASASVAGSSGPAACSPPSSSAPRSPESPAPRRGGVRASVPQKLAEM

LSSQYGLIVFVAGLLLLLAWAVHAAGVSKSDLLCFLTALMLLQLLWMLWYVGRSSAH

RRLFRLKDTHAGAGWLRGSITLFAVITVILGCLKIGYFIGFSECLSATEGVFPVTHSVHTL

LQVYFLWGHAKDIIQSFKTLERFGVIHSVFTNLLLWANGVLNESKHQLNEHKERLITLGF

GNITTVLDDHTPQCNCTPPTLCTAISHGIYYLYPFNIEYQILASTMLYVLWKNIGRKVDSH

QHQKMQFKSDGVMVGAVLGLTVLAATIAVVVVYLIHIGRSKTKSESALIMFYLYAITLL

MLMGAAGLAGIRIYRIDEKSLDESKNPARKLDSDLLVGTASGSWLISWGSILAILCAEGH

PRYTWYNLPYSILAIVEKYIQNLFIFESIHREPEKLSEDIQTLRVVTVCNGNTMPLASSCPK

SGGVARDVAPQGKDMPPAANGNVCMRESHDKEEEKQEESSWGGSPSPVRLPRFLQGN

AKRKVLRNIAAFLFLCNISLWIPPAFGCRPEYDNGLEEIVFGFEPWIIVVNLAMPFSIFYR

MHAAASLFEVYCKI

Human-OTOP2 (SEQ ID NO: 2):
MSEELAQGPKESPPAPRAGPREVWKKGGRLLSVLLAVNVLLLACTLISGGAFNKVAVY

DTDVFALLTAMMLLATLWILFYLLRTVRCPCAVPYRDAHAGPIWLRGGLVLFGICTLIM

DVFKTGYYSSFFECQSAIKILHPLIQAVFVIIQTYFLWVSAKDCVHVHLDLTWCGLMFTL

TTNLAIWMAAVVDESVHQSHSYSSSHSNASHARLISDQHADNPVGGDSCLCSTAVCQIF

QQGYFYLYPFNIEYSLFASTMLYVMWKNVGRFLASTPGHSHTPTPVSLFRETFFAGPVL
```

-continued

GLLLFVVGLAVFIIYEVQVSGDGSRTRQALVIYYSFNIVCLGLTTLVSLSGSIIYRFDRRA

MDHHKNPTRTLDVALLMGAALGQYAISYYSIVAVVAGTPQDLLAGLNLTHALLMIAQH

TFQNMFIIESLHRGPPGAEPHSTHPKEPCQDLTFTNLDALHTLSACPPNPGLVSPSPSDQR

EAVAIVSTPRSQWRRQCLKDISLFLLLCNVILWIMPAFGARPHFSNTVEVDFYGYSLWA

VIVNICLPFGIFYRMHAVSSLLEVYVLS

Human-OTOP3 (SEQ ID NO: 3):
MGRGARAAAAQSRWGRASRASVSPGRTIRSAPAVGEAQETEAAPEKENRVDVGAEER

AAATRPRQKSWLVRHFSLLLRRDRQAQKAGQLFSGLLALNVVFLGGAFICSMIFNKVA

VTLGDVWILLATLKVLSLLWLLYYVASTTRRPHAVLYQDPHAGPLWVRGSLVLFGSCT

FCLNIFRVGYDVSHIRCKSQLDLVFSVIEMVFIGVQTWVLWKHCKDCVRVQTNFTRCGL

MLTLATNLLLWVLAVTNDSMHREIEAELGILMEKSTGNETNTCLCLNATACEAFRRGFL

MLYPFSTEYCLICCAVLFVMWKNVGRHVAPHMGAHPATAPFHLHGAIFGPLLGLLVLL

AGVCVFVLFQIEASGPAIACQYFTLYYAFYVAVLPTMSLACLAGTAIHGLEERELDTVK

NPTRSLDVVLLMGAALGQMGIAYFSIVAIVAKRPHELLNRLILAYSLLLILQHIAQNLFIIE

GLHRRPLWETVPEGLAGKQEAEPPRRGSLLELGQGLQRASLAYIHSYSHLNWKRRALK

EISLFLILCNITLWMMPAFGIHPEFENGLEKDFYGYQIWFAIVNFGLPLGVFYRMHSVGG

LVEVYLGA

Mouse-OTOP1 (SEQ ID NO: 4):
MPGGPGAPSSPAASSGSSRAAPSGIAACPLSPPPLARGSPQASGPRRGASVPQKLAETLSS

QYGLNVFVAGLLFLLAWAVHATGVGKSDLLCVLTALMLLQLLWMLWYVGRSYMQRR

LIRPKDTHAGARWLRGSITLFAFITVVLGCLKVAYFIGFSECLSATEGVFPVTHAVHTLLQ

VYFLWGHAKDIIMSFKTLERFGVIHSVFTNLLLWANSVLNESKHQLNEHKERLITLGFGN

ITIVLDDHTPQCNCTPPALCSALSHGIYYLYPFNIEYQILASTMLYVLWKNIGRRVDSSQH

QKMQCRFDGVLVGSVLGLTVLAATIAVVVVYMIHIGRSKSKSESALIMFYLYAITVLLL

MGAAGLVGSWIYRVDEKSLDESKNPARKLDVDLLVATASGSWLLSWGSILAIACAETR

PPYTWYNLPYSVLVIVEKYVQNIFIIESVHLEPEGVPEDVRTLRVVTVCSSEAAALAASTL

GSQGMAQDGSPAVNGNLCLQQRCGKEDQESGWEGATGTTRCLDFLQGGMKRRLLRNI

TAFLFLCNISLWIPPAFGCRPEYDNGLEEIVFGFEPWIIVVNLAMPFSIFYRMHAAAALFE

VYCKI

Mouse-OTOP2 (SEQ ID NO: 5):
MSEELVPHPNESLPGPRASPREVWKKGGRLLSVLLAVNVLLLACTLISGGAFNKVAVYD

TDVFALLTTMMLLAALWIVFYLLRTARCPDAVPYRDAHAGPIWLRGGLVLFGICTLVM

DVFKTGYYSSFFECQSAIKILHPIIQAVFVIVQTYFLWISAKDCIHTHLDLTRCGLMFTLAT

NLAIWMAAVVDESVHQAHSYSGSHGNTSHTRLNPDSKRAGGAAEEDPCLCSTAICQIFQ

QGYFYLYPFNIEYSLFASTMLYVMWKNVGRLLASTHGHGHTPSRVSLFRETFFAGPVLG

LLLFVVGLAVFILYEVQVSGERGHTRQALVIYYSFNIVCLGLMTLVSLSGSVIYRFDRRA

MDHHKNPTRTLDVALLMGAALGQYAISYYSIVAVVVGSPRDLQGALNLSHALLMIAQH

TFQNVFIIESLHRGPPGAEPREMPPKEPCQGITFANLDAIRTLPSCPPTPRLVIPNLESPQEA

VAIISAPRCHWRRRCLKDISLFLLLCNVILWIMPAFGARPHFSNTVEVDFYGYSLWAAIV

NICLPFGIFYRMHAVSSLLEVYVLS

Mouse-OTOP3 (SEQ ID NO: 6):
MASQTSAPAEPAPMPSPEAKTTEGASSYDQADMETKHAGSPCPPKQKSWLARHFSLLL

RRDRQAQKAGQLFSGLLALNVVFLGGAFICSMIFNKVSVTLGDVWILLAALKVLSLLWL

-continued

LYYTVGTTRKPHAVLYRDPHAGPIWVRGSLVLFGSCTVCLNIFRMGYDVSHIHCKSEVE

LIFPAIEIVFMIIQTWVLWRHCKDCVQVQTNFTRCGLMLTLATNLLMWVLAVTNDSMH

REIEAELDALMEKFSGNGTNTCMCLNTTVCEVFRKGYLMLYPFSTEYCLICCAVLFVM

WKNVSRSLAAHTGAHPNRSPFRLHGTIFGPLLGLLALVAGVCVFVLFQIEASGPDIARQY

FTLYYAFYVAVLPTMSLACLAGTAIHGLEERELDTLKNPTRSLDVVLLMGAALGQMGI

AYFSIVAIVATQPHELLNQLILAYSLLLILQHITQNLFIIEGLHRRPLWEPAVSGVMEKQD

VELPRRGSLRELGQDLRRASRAYIHSFSHLNWKRRMLKEISLFLILCNITLWMMPAFGIH

PEFENGLEKDFYGYRTWFTIVNFGLPLGVFYRMHSVGGLVEVYLGA

*Drosophila*-OTOP variant D (CG42492), (SEQ ID NO: 7):
MQRCPYIHEMRERLLDQPRETLQLENMERANLLDNRQSASESNQLQGDGYHTSPAHQR

TPLVPHDLGEDFNLDFDDDFPIDARRPKNANDIHPAVLTRPQQRTSLFIVTSLVYAILLIV

VCIAYVISDVTTHRLPVLYYETFFTYLYGVSILFLLYVFCFLLQESSCCNGGNGGSKPKPQ

PKEKKSKKAKNADPADSKDAKGSKDSGKAAKGAAYQHTLAKFLEAPVDAEVAVTPKN

VRKRKTTHSDLTHGSFFLRVGAIAFGLGAMIYIGLEFGSFFEIPFDSPCHHILIGVNPLLQM

IFTFMQMYFIFMNARTRPPFQLNIHRFKVIARFGLMHVVATNICVWIRTLVKESLLEITIY

HQKNEPEAGASSIAHSIRQHALRHAGTVLRTHAGPNSEFEVLDGEDILPKDVYKSDNVL

SKLVRNTVDGISKSLGMGGDQALDSSTTSSSTTTTTRAPFTTPNYQWHSTTMARKLKKF

ITSATTAATTAAGSSSTASSTTTISPTISSTTIPSTTISSTTISSSTTFSPFSPSTTTTTTTAAA

LNLETSGSESPFGGLQRILSSAAPPSLAPVDGFGSASAATPTSGSGAGSFVDSFLASTLSPA

SSTEGSASIMNNLFGQGPMENSFQTYTDLGHEEATGLVSFENLESLDNIYPAALSSNIGTL

NSTACGRIDIMGTIVYDSAPYLYPFIIEYSLIGAVVLYVMWKHIGRYPGRMNDEDLEHRL

EVMLSRRAVAMAQQARSGRVDCVGSSKGLFFGLLLLVGALICLILFFVLVRHQQFSLLA

IYLADASHCILMAFAILAIIVGFIRVKNLKFRCEEQSNLNDILLRISAFGLFTYSVFSIIAGSL

KVLESEPSLLVTTTGGVAVFQVILQLLFIADVSRRRVHLPEHDRSKPGRQIVTFLLICNVA

MFAIYTFEAQKVFANPVSRYVQLEFYGFVPWSIIQRITLPLCIFHRFHSAVTLAEIWKTTY

KARLE

*Drosophila*-OTOP variant A (SEQ ID NO: 8):
MSLINLKSKDMYDEPINLWRTKQRVHYHHDVISKGNDSHRSSDACEYITISAPKKSGSFS

RSPPSSLPTSVPGTPRHSVAATSNQVIRYARTSCDHCGHHSIPVMSPHPISPLAKSQTNLD

LVEHGSQRQALLPLPTVGMHHEDSACTLQVSRRPSLLLQEILTQRPPLFGRRDGNGFLSP

RTAKNGNLQGTASGSTATINFQSGATSARNGSTAFFDNGAKSFQAKQQKDKNRRTGND

AISSALSATYCKLLVLLGVCLPITEVISDQIPTYVYQGFYVYLYVGSILFVIFLYISAFRNRS

LFNALKDYHEKNSNVHLKHKVTHFGSFYLRVGAIAFAIGTMVYSGLEFGQFFELNGHPG

CRDVFVAITPICRMVLCIAQVQFIFLNTTYMDMARHKVTSRFGLMHMVATNLCEWLYV

LVEETKHEIFHISQHEVDPAHDLVIHNSSMSRTDWAAVNESLHQHHHHHALNNTLVAN

VSSVIVNMTITPSPTPAAFSGCSRTTIMGALVQQLSPFLFPCTIEYSLICAVILFEMWKTVK

SIPDIDKTRKNSVKPAAAKPAHHFSVDCSQSHKGLFFGILIIVMTIISMIMYFVLYTQPGYE

LVATQEVTLWETFMYFMCAAAVITGMILMRDLRYIKNTSDEHHSMDLDNLLLIVAQTG

VYLYGMFSILGSYFAKWDTVPDRVEGIIAEVFGVVQTSLQTMFILHSSHRRCRGTNQVR

RKPGREIITFLLVANIAIWFVNTLIKGRAVFRESHLEFFGVWGWTIITHISMPLAIFYRFHS

TICLFEVWKITYKAKAH

-continued

Drosophila-OTOP variant D (CG42265) (SEQ ID NO: 9):
MDSSPDLSLKLRRGSSDSRDNFYMDFAQGIDSDIEEVDNTANNQEAGEVPPPPLPTVSLA

EEVLLLVAPPPPPPSLLGQPLPTLTETDDIPPTPTPPPQQKDDEGDDEDEREEPVPEQDQG

APAAPSPPGSPINSVLELELIPPPPLSPMDDAGLRTDDDGEGEETDDAEEVAAIPPPHEML

DIESNPDEEEEEEEQEQASQEDTPKEEDEEEDDDKSTPPPPLPPLPSNFSYVQGHNLGQVT

PPLTKSPSNSPSPPVTPPPCPELNISRMVSPPAQHISQIPPLTPSDESEGEAESQPNSPPLRLD

AEQPPPDMDQPEPEDQPPEPENEPEPEPEPEPEPEPVSGAREDYSRSLDNEDESTTITTPPS

NGYSASSIIAPPPEHFAELDEDRGFIPPPPLEQEPEEEVEEEEEEEEELTKETDEISVDRES

LQDQGGDSISSPRPASILTGSISTSVGGGAGGSPKPESRGPSRSGSQRSQLRSGSQQGSIAE

SRGGSRIGSRTGSVASAQAAGVLSPQASLKSQTSIRSQGQAGVRSPAGSIKSGSQRMQSP

QAGEGAPAMPSPPLMRSPPPELARQMHSPPRITTPPRVCSPPLVSSPPKLAESAAAAVGV

AATVKEQIGSSSSTAEPLEPSKPEPLKPPIATVSYQDEQKPSPPPTAAAAPAVTTTAATTA

VTSQPRSHFTSSHHHYHLPHQFQHPHHQNHHTHSVRVPTPTVPSSYAPPPPPDSGSSSSPV

DRRRLFMAGVAPPIAAGAGSLMAMPAEPAVAISPGRVSARSGSQHHVTIDESSLPSHKG

NIQETPGPSGLIIGGGDGDGDRDIGGGGGPDSSDPPSSPGGSSSQPALSGSQADGQLALM

YHSHQLTNYPVLPAIKRTHRPSFVYPPMPRVKAGDALATLFSALYGKLLVVMGIAFPMA

EVISTYIPPSFYEVYYLYLYIGSMIFLLFMYATLIWGRPKLPVPIASPSKSATKASGTDSMD

ESDTDSNSVHHRLPPPIPVRRPSLLSPLGRRDAHYGSFYLRMGAVAFGIGSMIYSGLEFG

QYFELNPDTKCHNVLLALTPATRMAFIFIQMYFIFLNNEQIKVYRYKIIARFGLMHMIGT

NLAVWLNVLIQETKHEILTFYNPENRTLRISHRIPGHSRGHAIIQHDPTAHLRVPRGLKGP

YQIFECRRTNIIGTLVQDASPFLFPCTIEYSLICAAILYVMWRSISRPQTPTPQRPDMISSPM

KRSPHHYSVDCARAHKGLFVGILILVLTIISLIIFFVLISRPEFVAMAVTEVTICELLIYGTA

TIATLVGMIQIRHLQYDAYRSFSLDDILLVGAQTGSFLYNIFTVIAGHFTLRSDDMLVPIN

ALASIVQTACQTMFILDASRRQAVSPEHLRKKPGREIVTFMLVVNLAMWAISTLEKSRA

ESHPIQLNFYGLWAWTIITHVSMPLAIFYRFHSTVCLCEIWKRAYKLKPTYMXEFARSRI

QSIAQQQQFCEDLKTNLSYCYCSTTLAGGELETVEEVDSGESNSAEDAGAGAGSGGSRG

SGGGAGAAEAGEAGEEGQQGGDSSCGLKAPIRALSPQSLNTEKAFCPVYVINGE

\* \* \*

The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It will be understood by those of skill in the art that numerous and various modifications can be made without departing from the spirit of the technology. Therefore, it should be clearly understood that the forms of the technology are illustrative only and are not intended to limit the scope of the technology.

All references cited herein are hereby incorporated by reference in their entirety.

What is claimed is:

1. A method of identifying a modulator of otopetrin-mediated proton translocation activity comprising:
   (a) contacting an otopetrin polypeptide, or host cell expressing said polypeptide with a test compound, wherein said otopetrin polypeptide is selected from the group consisting of: a mammalian otopetrin polypeptide; Otop1; Otop2; Otop3; an insect otopetrin polypeptide; and an otopetrin polypeptide that is at least 95% identical, at least 96% identical, at least 97% identical, at least 98% identical, at least 99% identical, or 100% identical to an otopetrin polypeptide sequence of any one of SEQ ID Nos:1-9; and
   (b) determining a proton translocation activity mediated by the otopetrin polypeptide;
   wherein an increase or decrease of at least 1% of the proton translocation activity, compared to an amount of proton translocation activity determined in an absence of the test compound, identifies the test compound as a modulator of the proton translocation activity mediated by the otopetrin polypeptide.

2. The method of claim 1, wherein determining the proton translocation activity comprises:

measuring conductivity, current, resistance, voltage potential across a membrane comprising the otopetrin polypeptide; or measuring intracellular pH or intracellular calcium within a host cell expressing an otopetrin polypeptide.

3. The method of claim 2, wherein the conductivity, voltage potential, current, resistance, intracellular pH, or intracellular calcium, is measured in response to a change in extracellular pH.

4. The method of claim 3, wherein determining the proton translocation activity comprises a patch clamp technique, voltage clamp technique, measurement of whole-cell current, or use of a pH-sensitive indicator or calcium-sensitive indicator.

5. The method of claim 4, wherein:
the pH-sensitive indicator comprises pHluorin, DFFDA, and BCECF;
the calcium-sensitive indicator comprises Fura-2, Fluo-4 or Fluo-3
the change in extracellular pH is an increase in pH;
the change in extracellular pH is a decrease in pH; and/or
the change in extracellular pH is at least 0.1 pH units.

6. The method of claim 1, wherein determining the proton translocation activity comprises expressing the otopetrin polypeptide in a cell, wherein:
the cell is a mammalian cell;
the cell is an oocyte; and/or
the cell is a HEK-293 cell or a CHO cell.

7. The method of claim 1, wherein the test compound is selected from the group consisting of a small organic molecule, small inorganic molecule, electrophile, polysaccharide, peptide, protein, antibody, nucleic acid, and an extract, wherein the extract is from a biological material is selected from a bacteria, plant, fungi, animal cell, and animal tissue.

8. The method of claim 1, wherein:
the test compound has a molecular weight in a range of 50 to 500,000 Daltons;
the test compound is at a concentration in a range of: 1 pM to 100 mM; 1 pM to 10 mM; 1 pM to 1 mM; 10 pM to 100 mM; 10 pM to 10 mM; 10 pM to 1 mM; 100 pM to 100 mM; 100 pM to 10 mM; 100 pM to 1 mM; or about 0.1 µM to about 1000 mM; and/or
the test compound is at a concentration of at least 1 pM.

9. A method of identifying a modulator of otopetrin-mediated proton translocation activity comprising:
(a) measuring a proton translocation activity mediated by an otopetrin polypeptide, (i) in the presence of a test compound, and (ii) in the absence of the test compound, wherein said otopetrin polypeptide is selected from the group consisting of: a mammalian otopetrin polypeptide; Otop1; Otop2; Otop3; an insect otopetrin polypeptide; and an otopetrin polypeptide that is at least 95% identical, at least 96% identical, at least 97% identical, at least 98% identical, at least 99% identical, or 100% identical to an otopetrin polypeptide sequence of any one of SEQ ID Nos:1-9; and
(b) determining a difference between the proton translocation activity measured in (a)(i) compared to the proton translocation activity measured in (a)(ii), thereby identifying the test compound as a modulator of the proton translocation activity mediated by the otopetrin polypeptide.

10. The method of claim 9, wherein:
the difference is at least a difference of 1%;
the proton translocation activity measured in (a)(i) is at least 1% greater than the proton translocation activity measured in (a)(ii) and the test compound is identified in (b) as an agonist of the proton translocation activity mediated by the otopetrin polypeptide; and/or
the proton translocation activity measured in (a)(i) is at least 1% less than the proton translocation activity measured in (a)(ii) and the test compound is identified in (b) as an antagonist of the proton translocation activity mediated by the otopetrin polypeptide.

11. The method of claim 9, wherein measuring the proton translocation activity comprises a patch clamp technique, measurement of whole-cell currents, two-electrode voltage clamping, or a fluorescence assay using a voltage-sensitive dye.

12. The method of claim 9, wherein measuring the proton translocation activity comprises:
measuring conductivity, current, voltage potential or resistance across a membrane comprising the otopetrin polypeptide; or
measuring intracellular pH or intracellular calcium across a membrane comprising the otopetrin polypeptide in response to a change in extracellular pH.

13. The method of claim 12, wherein the change in extracellular pH is induced on one side of the otopetrin polypeptide, and wherein:
the change in extracellular pH is an increase in extracellular pH;
the change in extracellular pH is a decrease in extracellular pH; and/or
the change in extracellular pH is at least 0.1 pH units.

14. The method of claim 9, wherein the method further comprises expressing the otopetrin polypeptide in a homologous cell or a heterologous cell, wherein the homologous cell or the heterologous cell:
is a mammalian cell;
is an oocyte; and/or
is a taste receptor cell.

15. The method of claim 9, wherein the test compound is selected from the group consisting of a small organic molecule, small inorganic molecule, polysaccharide, peptide, protein, antibody, nucleic acid, and an extract, wherein the extract is from a biological material is selected from a bacteria, plant, fungi, animal cell, and animal tissue.

16. The method of claim 9, wherein:
the test compound has a molecular weight in a range of 50 to 500,000 Daltons;
the test compound is at a concentration in a range of: 1 pM to 100 mM; 1 pM to 10 mM; 1 pM to 1 mM; 10 pM to 100 mM; 10 pM to 10 mM; 10 pM to 1 mM; 100 pM to 100 mM; 100 pM to 10 mM; 100 pM to 1 mM; or about 0.1 µM to about 1000 mM; and/or
the test compound is at a concentration of at least 1 pM.

* * * * *

UNITED STATES PATENT AND TRADEMARK OFFICE
CERTIFICATE OF CORRECTION

| | |
|---|---|
| PATENT NO. | : 11,467,168 B2 |
| APPLICATION NO. | : 16/634566 |
| DATED | : October 11, 2022 |
| INVENTOR(S) | : Emily Liman and Yu-Hsiang Tu |

It is certified that error appears in the above-identified patent and that said Letters Patent is hereby corrected as shown below:

In the Specification

In Column 1, Line 16:
Replace "This invention was made, in part, with government support under National Institutes of Health grants R01DC013741 and R21DC012747. The government has certain rights in the invention."
With --This invention was made with government support under R21 DC012747, and R01 DC013741 awarded by the National Institutes of Health. The government has certain rights in the invention.--

Signed and Sealed this
Third Day of January, 2023

*Katherine Kelly Vidal*

Katherine Kelly Vidal
*Director of the United States Patent and Trademark Office*